(12) United States Patent
Madsen et al.

(10) Patent No.: US 9,296,835 B2
(45) Date of Patent: Mar. 29, 2016

(54) POLYMERIC PHOTOINITIATORS AND PHOTOINITIATOR MONOMERS

(71) Applicant: Coloplast A/S, Humlebaek (DK)

(72) Inventors: Niels Joergen Madsen, Alleroed (DK); Petr Sehnal, York (GB); David George Anderson, York (GB); Bo Rud Nielsen, Alleroed (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 14/401,125

(22) PCT Filed: May 14, 2013

(86) PCT No.: PCT/DK2013/050144
§ 371 (c)(1),
(2) Date: Nov. 14, 2014

(87) PCT Pub. No.: WO2013/170858
PCT Pub. Date: Nov. 21, 2013

(65) Prior Publication Data
US 2015/0148441 A1    May 28, 2015

(30) Foreign Application Priority Data
May 16, 2012 (DK) ................................ 2012 70262

(51) Int. Cl.
| | |
|---|---|
| C08F 2/46 | (2006.01) |
| C08F 2/50 | (2006.01) |
| C08G 61/04 | (2006.01) |
| C08G 18/48 | (2006.01) |
| C08G 18/66 | (2006.01) |
| C08G 18/32 | (2006.01) |
| C07C 49/84 | (2006.01) |
| C07C 69/738 | (2006.01) |
| C08G 18/73 | (2006.01) |
| C08G 63/00 | (2006.01) |
| G03F 7/038 | (2006.01) |

(52) U.S. Cl.
CPC . *C08F 2/50* (2013.01); *C07C 49/84* (2013.01); *C07C 69/738* (2013.01); *C08G 18/3215* (2013.01); *C08G 18/4833* (2013.01); *C08G 18/6674* (2013.01); *C08G 18/73* (2013.01); *C08G 63/00* (2013.01); *G03F 7/0384* (2013.01)

(58) Field of Classification Search
CPC ......... C08F 2/50; C07C 69/738; C07C 49/84; C08G 18/73; C08G 63/00; C08G 18/6674; C08G 18/4833; C08G 18/3215; G03F 7/0384
USPC ............. 522/35, 33, 6, 1, 71, 189, 184; 520/1
See application file for complete search history.

(56) References Cited

U.S. PATENT DOCUMENTS

| | | | |
|---|---|---|---|
| 3,931,302 A | 1/1976 | Allais et al. | |
| 4,296,125 A | 10/1981 | Borzatta et al. | |
| 8,742,163 B2 | 6/2014 | Knebel et al. | |
| 2012/0010317 A1* | 1/2012 | Schmitt et al. | 522/35 |
| 2013/0210954 A1* | 8/2013 | Loccufier | 522/53 |

FOREIGN PATENT DOCUMENTS

| | | | |
|---|---|---|---|
| EP | 1676870 A1 | 7/2006 | |
| FR | 2269330 A2 | 11/1975 | |
| WO | 2009147057 A1 | 12/2009 | |
| WO | 2010072479 A1 | 7/2010 | |
| WO | 2012/052288 | * | 4/2012 |

OTHER PUBLICATIONS

Jeffrey W. Leon and David G. Whitten: "Photodegradation of oligomeric polyesters containing anthraquinone and 1,2-diamine units. Single electron transfer induced cation radical bond cleavage in the solid state", The Journal of American Chemical Society, 1995, 117, pp. 2226-2235.
De Mesmaeker et al.: "Amide backbone modifications for antisense oligonucleotides carrying potential intercalating substituents: Influence on the thermodynamic stability of the corresponding duplexes with RNA- and DNA-Complements", Bioorganic & Medical Chemistry Letters, Pergamon, Elsevier Science, GB, vol. 7, No. 14, Jul. 22, 1997, pp. 1869-1874.
"Letters in volume 43", Thin solid films, Elsevier-Sequida S.A. Lausanne, CH, vol. 43, No. 3, Jun. 15, 1977, p. 363.
Ayyangar N R et al.: "(Trichloromethyl)Benzene: A versatile reagent for the preparation of substituted benzophenones", Synthesis, Georg Thieme Verlag, Stuttgart, DE, No. 4, Apr. 1, 1991, pp. 322-324.
Scott K. Christensen et al.: "Gelation of Copolymsers with Pendent Benzophenone Photo-Cross-Linkers", Macromolecules, vol. 45, No. 12, Jun. 26, 2012, pp. 5237-5246.

* cited by examiner

*Primary Examiner* — Ling Choi
*Assistant Examiner* — Jessica E Whiteley
(74) *Attorney, Agent, or Firm* — Coloplast Corp., Coloplast A/S; Nick Baumann

(57) ABSTRACT

The present invention provides polymeric photoinitiators being co-polymers of photoinitiator monomers and at least one further monomer, as well as photoinitiator monomers being intermediates in the preparation of such polymeric photoinitiators. Additionally, there is provided polyacrylate obtained by radical polymerization of at least one acrylate monomer (Ac) in the presence of such polymeric photoinitiators. In the photoinitiator monomers and polymeric photoinitiators, a photoinitiator moiety, a hydrolytic stable linker and two polymerizable functional groups are incorporated into the photoinitiator structure.

42 Claims, 2 Drawing Sheets

POLYMERIC PHOTOINITIATORS AND PHOTOINITIATOR MONOMERS

FIELD OF THE INVENTION

Figure 1:
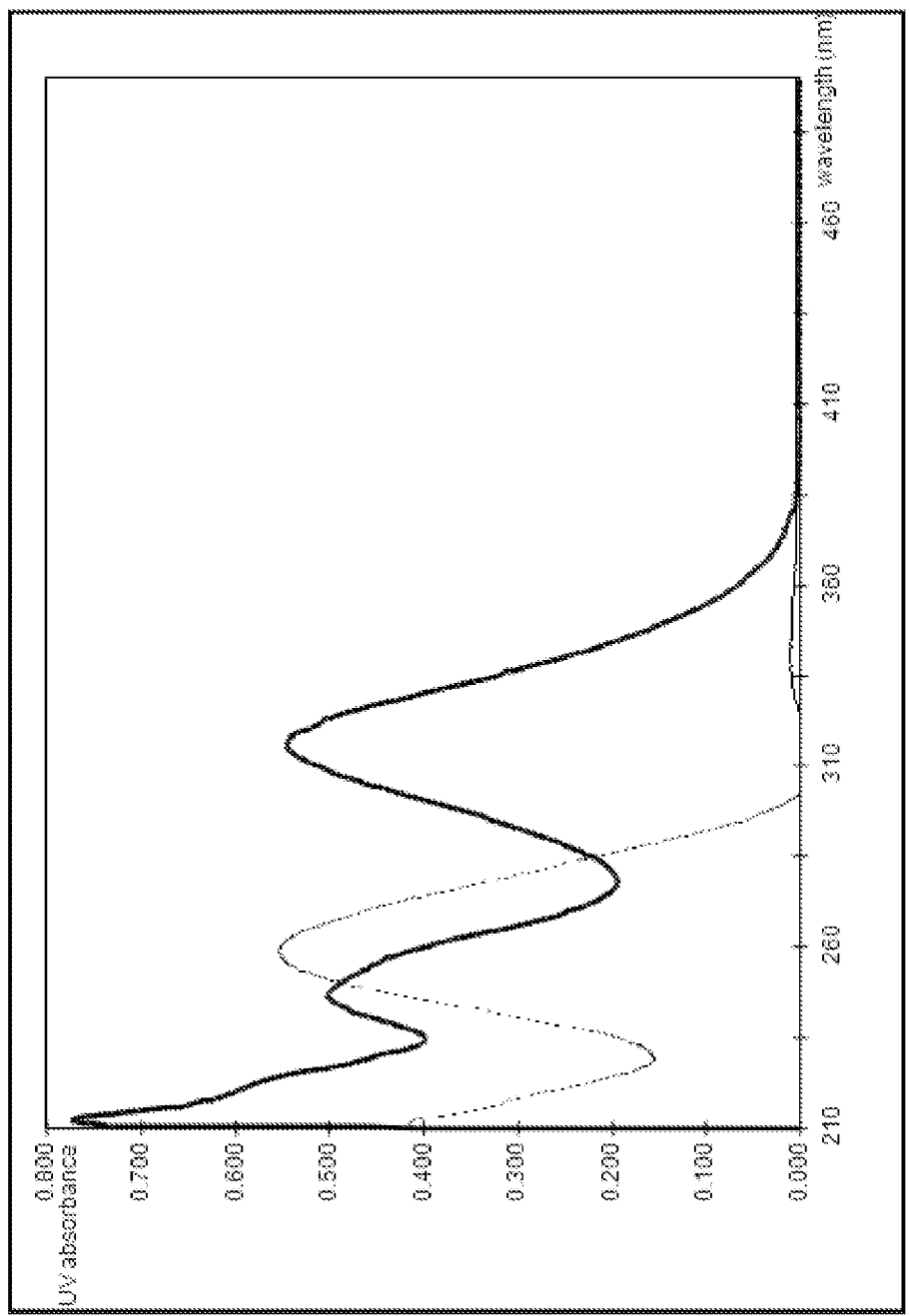

The present invention relates to polymeric photoinitiators where the photoinitiator moieties are incorporated as pendant groups on the polymeric backbone, as well as photoinitiator monomers being intermediates in the preparation of such polymeric photoinitiators. Additionally, the present invention relates to polyacrylates obtained by radical polymerization of at least one acrylate monomer (Ac) in the presence of a polymeric photoinitiator. The intermediate photoinitiator monomers are especially suited for industrial preparation of polyethers and polyesters due to their hydrolytic stability and are designed to allow preparation of linear photoinitiator polymers due to a branching point with two functional groups.

BACKGROUND OF THE INVENTION

Curing of coatings through ultraviolet (UV) radiation requires efficient methods of initiating the chemical reaction responsible for the curing process. Curing of polymeric material through generation of radical species upon irradiation with UV light is widely used to produce coatings for medical devices. The paint and lacquer industry also makes use of UV-initiated curing of acrylates, where photoinitiators in many cases are employed. These two examples illustrate the diversity of UV curable coatings.

In a UV curing process, a photoinitiator moiety (low molecular weight or polymer-bound) absorbs UV light and undergoes transition to an excited state, which undergoes further processes which result in the formation of free radicals. This stage is known as initiation.

A polymer photocrosslinking process starts out with long linear polymer chains, and the initiation stage proceeds as described above. Through hydrogen abstraction, the free radicals can be transferred from the photoinitiator to an existing polymer backbone. Hereby forming new carbon-carbon bonds via radical recombination between the polymer chains providing a cross-linking of the before linear polymer chain. Such photoinitiators can be either of low molecular weight or bound in a polymer backbone.

One advantage of this photocrosslinking method is that a linear polymer has considerably different properties than the same type of polymer being cross-linked. The linear polymer may for example be soluble and can then be used in different production processes; it may be e.g. applied on medical devices by spraying or dip coating. The photocrosslinking process may then be initiated afterwards, cross-linking the polymer attaching it to the surface it is applied upon. It will neither dissolve nor melt.

Alternatively, the free radicals formed in the initiation stage may react with unsaturated monomers. This is then called a radical propagation stage. As the unsaturated moieties are transformed to new carbon-carbon bonds, the molecular weight of the radical grows and a new polymer chain is formed, i.e. the polymer is formed from unsaturated monomers and is cross-linked in the same process.

Until recently, polymers designed for use in coatings have relied on photoinitiators with relatively low molecular weight to initiate the cross-linking. Low molecular weight substances, and their by-products in the polymerization reaction, are generally difficult to remove from the resultant cross-linked polymer, but instead remain within the polymer matrix and diffuse slowly to the surface of the polymer during its lifetime. Over time, low molecular weight substances therefore leach from the polymer into the surrounding environment.

This presents particular problems in the polymers used in the medical field, as patient safety considerations limit the amount and type of substance which can leach from a given polymer. This is especially relevant if the polymer is to be used as a coating or adhesive which is designed to be in contact with the inside or outside of the patient's body.

Higher molecular weight photoinitiators, in particular polymeric photoinitiators, have comparably higher intrinsic viscosities which most likely result in longer diffusion times through a matrix. Migration of the UV active substances to the surface is therefore diminished when polymeric photoinitiators are used as opposed to lower molecular weight photoinitiators. Scarce literature within the field of polymeric photoinitiators suggests that development of such polymers could lead to novel applications and present solutions for existing needs, such as providing a material with negligent migration of substances to the surface/patient.

The majority of commercial polymeric initiators are based on a linear polymer backbone structure where a photoinitiator species is attached by a linking group to one (WO 96/33156) or both (U.S. Pat. No. 4,602,097) ends of a polymeric chain. While this type of structure provides a cost effective route to production of non-migratable photoinitiators, the linear structures tend to give rise to viscous oils and resinous materials. More problematic, the active photoinitiator weight fraction of the molecule is significantly reduced compared to the parent monomer and therefore a reduction in photoactivity by 50% or more is typically observed.

WO 2009/016083 reports a method for improving the degradation of natural or synthetic polymers by incorporating degradation accelerators into polymers composition prior to forming any products. Among the described degradation accelerators are oligomeric benzophenone compounds having amide linkers and ester bonds. It is described that such polymer products are degradable triggered by light, heat or humidity.

WO 2008/070737 relates to benzophenone and thioxanthone derivatives and their use in UV curable compositions. The examples therein show how sulphur containing benzophenone derivatives are reacted with acrylate formulations. The derivatives all have at least three ester linkers in each structure.

Polymeric photoinitiators based on a polyurethane main chain have been reported by Wei et al. (Macromolecules 2009, 42, 5486-5491). However, all materials prepared are linear polymeric structures with initiator species within the chain itself. While synthetically available, the present inventors find that 'in-chain' polymeric photoinitiators tend to suffer from intrinsically lower photoactivity compared to the photoinitiator monomers. Moreover, linear polymers with in-chain aromatic moieties are prone to give materials with higher degree of crystallinity and much lower solubility compared to other polymer architectures.

Accordingly, it is an object of the present invention to provide polymeric photoinitiators having better photoactivity, in order to efficiently substitute low weight photoinitiators, where migration from the final products are critical. Additionally, it is desirable that such polymeric photoinitiators have good processing properties in the linear polymer state, for use in e.g. coating processes.

It is furthermore an object of the present invention to provide photoinitiators monomers that are stable under the chemical reaction conditions used during handling and polymerisation. This in order to additionally minimise the number of degradation products and by-products that may be present in the final polymeric matrix, and hence the above described migration from the matrix.

A photoinitiator comprising a photoinitiator moiety, an ester linker and two functional groups used in polymerisation of a polyester have been described by Whitten et al. The polymers prepared are photodegraded by means of UV light with λ>340 nm. The fragmentation reaction relies on inter- or intramolecular single electron transfer (SET) between 1,2-diamine donor units and anthraquinone acceptor units followed by photooxidative C—C bond cleavage. The polymerisation reaction disclosed is a reaction between two hydroxy groups and a diacid chloride carried out in dichloroethane with hexanedioyl dichloride and pyridine base (J. Am. Chem. Soc. vol 117, No. 8, 2226-2235, 1995). WO2009016083 describes synthesis of a similar photoactive polyester from 2-benzoyl-N,N-bis(2-hydroxyethyl)benzamide and terephthaloyl chloride with triethylamine base in refluxing THF. The present inventors find that these fairly mild esterification conditions are generally not suitable for large scale industrial production of polyester polymers. This due to both high cost and toxicity of base co-reagents, such as pyridine and triethylamine, and environmental concerns regarding chlorinated solvents. Industrial production of polyesters relies on more robust, albeit slower reactions starting from e.g. diols, dicarboxylic acids, diesters or hydroxyacids, rather than expensive diacid chlorides. This requires photoinititiators compatible and stable under typical harsh transesterification conditions: Reaction temperatures in direct esterification or transesterification processes can exceed 200° C., and strong acid catalysts are used such as mineral acids, titanium alkoxides or dialkyltin oxides.

A further object of the present invention is to provide polymers with even higher backbone stability than polyesters, particularly when these are to be applied as coatings in various melt and coextrusion processes. Polyetherification reactions are typically carried out at temperatures that may exceed 150° C. in the presence of strong bases such as alkali metal hydroxides or carbonates. Reaction conditions used in such large scale polyetherification processes are generally incompatible with the presence of ester or amide linkages in the co-monomer molecules, when degradation products are to be avoided.

For example, the previously known photoinitiator molecules in which a linker with two reactive groups is tethered to a photoinitiator moiety through an ester linkage would be hydrolysed, and polyether polymers with pendant photoinitiator groups could not be obtained. For this reason, the photoinitiator diol discussed above described by Whitten et al. would not be suitable for large scale production of neither polyethers nor polyesters.

Accordingly, there has been an unmet need for photoinitiator monomers capable of being incorporated into polymeric photoinitiators in industrial scale production where costs and environmental load of toxic solvents plays a role. This is especially relevant in the production of polyethers or polyesters.

The present invention provides polymer photoinitiators in which the photoinitiator moiety itself becomes an integral part of the polymer, and remains so, during and after the polymerization process. Leaching of photoinitiator and photoinitiator by-products is therefore reduced or even eliminated. Polymers likely to improve medical safety are thereby obtained.

The photoinitiators of the present invention additionally allow for production on industrial scale under strongly acidic or strongly basic conditions which can lead to hydrolysis of moieties such as esters and amides.

SUMMARY OF THE INVENTION

In a first aspect, the present invention provides polymeric photoinitiators, being co-polymers of at least one monomer (A) with at least one monomer (B), wherein:
monomer (A) is a photoinitiator monomer (A) of the formula (I):

wherein:
Pi is a photoinitiator moiety;
Z is a linker moiety selected from a single bond, $C_1$-$C_{12}$ alkylene, $C_2$-$C_{12}$ alkenylene, $C_3$-$C_8$ cycloalkyl, aryl, heterocyclyl, —($C_1$-$C_{12}$ alkylene)-aryl-, -aryl-($C_1$-$C_{12}$ alkylene)-, —($C_1$-$C_{12}$ alkylene)-heterocyclyl-, -heterocyclyl-($C_1$-$C_{12}$ alkylene)-, —[O—($C_1$-$C_{12}$ alkylene)]$_m$-, —[S—($C_1$-$C_{12}$ alkylene)]$_m$-, —[($C_1$-$C_{12}$ alkylene)-O]$_m$—, —[($C_1$-$C_{12}$ alkylene)-S—]$_m$—, —[O—($C_1$-$C_{12}$ alkylene)]$_m$-O—, —[S—($C_1$-$C_{12}$ alkylene)]$_m$-S—, —[O—($C_1$-$C_{12}$ alkylene)]$_m$-S—, —[S—($C_1$-$C_{12}$ alkylene)]$_m$-O—; —C(=O)—, —[C(=O)—($C_1$-$C_{12}$ alkylene)]$_m$-, [C(=O)-aryl]$_m$-, and —[C(=O)-heterocyclyl]$_m$-;
$R^1$ is selected from H, $C_1$-$C_{12}$ alkyl, $C_2$-$C_{12}$ alkenyl, $C_3$-$C_8$ cycloalkyl, aryl, heterocyclyl, —[O—($C_1$-$C_{12}$ alkylene)]$_m$-H, —[S—($C_1$-$C_{12}$ alkylene)]$_m$-H, —C(=O)—H, —[C(=O)—($C_1$-$C_{12}$ alkylene)]$_m$-H, —[C(=O)-aryl]$_m$-H and —[C(=O)-heterocyclyl]$_m$-H;
$X_1$ and $X_2$ are each independently selected from single bond, $C_1$-$C_{12}$ alkylene, $C_2$-$C_{12}$ alkenylene, $C_3$-$C_8$ cycloalkyl, aryl, heterocyclyl, —[O—($C_1$-$C_{12}$ alkylene)]$_p$, and —[S—($C_1$-$C_{12}$ alkylene)]$_p$;
wherein $X_1$, $X_2$, $R^1$ or Z each independently may be linked to one another to form one or more ring structures;
$W_1$ and $W_2$ are each independently selected from —OH, —CH$_2$OH, —COOH, —COOR$^2$, —COO-aryl, —SH, —CH$_2$SH, —NH$_2$, —NHR$^2$, —NCO, —NCS, —C(=O)—Cl, and —O—C(=O)—Cl;
$R^2$ is selected from optionally substituted $C_1$-$C_{12}$ alkyl and aryl;
m is an integer from 1-10;
n is an integer of 1 or 2, with the proviso that when n is 2, $R^1$ is absent;
p is an integer from 1-10; and
wherein any Pi, alkyl, alkenyl, alkylene, alkenylene, cycloalkyl, aryl, or heterocyclyl moiety each independently is optionally substituted with one or more substituents selected from —F, —Cl, —Br, —I, —CN, —NO$_2$, —C$_1$-C$_6$ alkyl, aryl, —O—(C$_1$-C$_6$ alkyl), —S—(C$_1$-C$_6$ alkyl), —S(O)—(C$_1$-C$_6$ alkyl), and —SO$_2$—(C$_1$-C$_6$ alkyl); and monomer (B) comprises at least two functional groups $W_3$ and $W_4$, said $W_3$ and $W_4$ being independently selected from —F, —Cl, —Br, —I, —OSO$_2$R$^4$, —OSO$_2$—Ar$^3$, —OH, —CH$_2$OH, —COOH, —COOR$^4$, —COO-aryl, —SH, —CH$_2$SH, —NH$_2$, —NHR$^4$, —NCO, —NCS, —C(=O)—Cl, and —O—C(=O)—Cl, wherein R$^4$ is selected from optionally substituted C$_1$-C$_{12}$ alkyl; or $W_3$ and $W_4$ are linked to each other forming a cyclic lactone or thiolactone;

wherein $W_1$, $W_2$, $W_3$ and $W_4$ are selected such that—in the co-polymerization of monomers (A) and (B)—$W_1$ reacts with $W_3$ to form a urethane, urea, amide, thiourethane, thiourea, dithiourethane, ester, ether, carbonate, phosphonite, phosphonate, phosphate, allophanate or biuret moiety, and $W_2$ reacts with $W_4$ to form a urethane, urea, amide, thiourethane, thiourea, dithiourethane, ester, ether, carbonate, phosphonite, phosphonate, phosphate, allophanate or biuret moiety.

The physical and chemical properties of the polymeric photoinitiators of the present invention can be tailored as required, e.g. by varying the relative amounts and the nature of each monomer (A) or (B). The Z linker confers increased stability to the final polymeric photoinitiators prepared from the monomer as it is stable towards hydrolysis e.g. during storage of water containing products like hydrogels.

In a second aspect, the present invention provides intermediates to be used in preparation of the polymeric photoinitiators: photoinitiator monomers of the general formula (Ia):

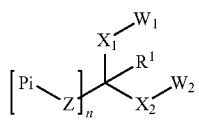

(Ia)

wherein:
Pi is a photoinitiator moiety;
Z is a linker moiety selected from a single bond, C$_1$-C$_{12}$ alkylene, C$_2$-C$_{12}$ alkenylene, C$_3$-C$_8$ cycloalkyl, aryl, heterocyclyl, —(C$_1$-C$_{12}$ alkylene)-aryl-, -aryl-(C$_1$-C$_{12}$ alkylene)-, —(C$_1$-C$_{12}$ alkylene)-heterocyclyl-, -heterocyclyl-(C$_1$-C$_{12}$ alkylene)-, —[O—(C$_1$-C$_{12}$ alkylene)]$_m$-, —[S—(C$_1$-C$_{12}$ alkylene)]$_m$-, —[(C$_1$-C$_{12}$ alkylene)-O]$_m$—, —[(C$_1$-C$_{12}$ alkylene)-S—]$_m$—, —[O—(C$_1$-C$_{12}$ alkylene)]$_m$-O—, —[S—(C$_1$-C$_{12}$ alkylene)]$_m$-S—, —[O—(C$_1$-C$_{12}$ alkylene)]$_m$-S—, —[S—(C$_1$-C$_{12}$ alkylene)]$_m$-O—; —C(=O)—, —[C(=O)—(C$_1$-C$_{12}$ alkylene)]$_m$-, —[C(=O)-aryl]$_m$-, and —[C(=O)-heterocyclyl]$_m$-;
R$^1$ is selected from H, C$_1$-C$_{12}$ alkyl, C$_2$-C$_{12}$ alkenyl, C$_3$-C$_8$ cycloalkyl, aryl, heterocyclyl, —[O—(C$_1$-C$_{12}$ alkylene)]$_m$-H, —[S—(C$_1$-C$_{12}$ alkylene)]$_m$-H, —C(=O)—H, —[C(=O)—(C$_1$-C$_{12}$ alkylene)]$_m$-H, —[C(=O)-aryl]$_m$-H and —[C(=O)-heterocyclyl]$_m$-H;
$X_1$ and $X_2$ are the same and are selected from single bond, C$_1$-C$_{12}$ alkylene, C$_2$-C$_{12}$ alkenylene, C$_3$-C$_8$ cycloalkyl, aryl, heterocyclyl, —[O—(C$_1$-C$_{12}$ alkylene)]$_p$, and —[S—(C$_1$-C$_{12}$ alkylene)]$_p$;
wherein $X_1$, $X_2$, R$^1$ or Z each independently may be linked to one another to form one or more ring structures;
$W_1$ and $W_2$ are the same and are selected from —OH, —CH$_2$OH, —COOH, —COOR$^2$, —COO-aryl, —NH$_2$, —NHR$^2$, —NCO, —NCS, —C(=O)—Cl, and —O—C(=O)—Cl;

R$^2$ is selected from optionally substituted C$_1$-C$_{12}$ alkyl and aryl;
m is an integer from 1-10;
n is an integer of 1 or 2, with the proviso that when n is 2, R$^1$ is absent;
p is an integer from 1-10; and
wherein any Pi, alkyl, alkenyl, alkylene, alkenylene, cycloalkyl, aryl, or heterocyclyl moiety each independently is optionally substituted with one or more substituents selected from —F, —Cl, —Br, —I, —CN, —NO$_2$, —C$_1$-C$_6$ alkyl, aryl, —O—(C$_1$-C$_6$ alkyl), —S—(C$_1$-C$_6$ alkyl), —S(O)—(C$_1$-C$_6$ alkyl), and —SO$_2$—(C$_1$-C$_6$ alkyl);
with the proviso that the photoinitiator monomer is not
1,3-diethyl 2-[(3-benzoylphenyl)methyl]propanedioate,
1,3-diethyl 2-({3-[(4-chlorophenyl)carbonyl]phenyl}methyl)propanedioate,
1,3-diethyl 2-[(3-benzoyl-2-methoxyphenyl)methyl]propanedioate,
2-[(3-benzoyl-2-methoxyphenyl)methyl]propanedioic acid, or
1,3-dimethyl 2-[(9,10-dioxo-9,10-dihydroanthracen-2-yl)methyl]propanedioate.

The particular structure of the photoinitiator monomer with two functional groups allows it to be incorporated as a monomer into a linear polymer chain. Therefore, the monomers of formulas (I) are intermediates in the formation of the corresponding polymers. The photoinitiator monomers of formula (Ia)—these being a subgroup of formula (I)—are especially preferred as they are symmetrically around the two functional groups providing good control of the polymerization reaction as each functional group has the same degree of reactivity.

Furthermore, the applied Z linkers (formula (I) and (Ia)) confer good hydrolytic stability and allow for industrial preparation of polymers without hydrolysing linker or other moieties in the photoinitiator compounds of the invention. The Z linker furthermore confers increased stability of polymeric photoinitiators prepared from the monomer as it is stable towards hydrolysis e.g. during storage of water containing products like hydrogels. Thereby, aid minimizing undesirable degradation products.

In a third aspect, the present invention provides a polyacrylate obtained by radical polymerization of at least one acrylate monomer (Ac) in the presence of a polymeric photoinitiator. The polymeric photoinitiator is a co-polymer of at least one monomer (A) with at least one monomer (B), wherein:
monomer (A) is a photoinitiator monomer (A) of the formula (I):

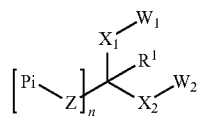

(I)

wherein formula (I) is as defined herein for photoinitiator monomers of general formula (I), according to the first aspect of the invention; and
monomer (B) is as defined herein for polymeric photoinitiators of the first aspect of the invention.

Polymerization of acrylate monomers in the presence of the polymeric photoinitiators of the invention is rapid, and— as the polymeric photoinitiator remains bound in the polyacrylate—leaching of photoinitiator is reduced or even completely eliminated.

The invention furthermore provides methods for producing the polymeric photoinitiator, of cross-linking the polymeric photoinitiator by means of UV radiation and/or heat, and for producing a polyacrylate using the polymeric photoinitiator as described.

Additionally, the invention provides the use of the polymeric photoinitiator as a photoinitiator of radical polymerization, the use of a polymeric photoinitiator as a photoinitiator of radical polymerization of acrylate monomers, and the use of a photoinitiator of formula (I) or (Ia) for preparation of a polymeric photoinitiator.

Further details of the above aspects of the invention are presented in the section "detailed disclosure of the invention" and in the dependent claims.

FIGURES

FIG. 1: shows the UV absorption spectra of Speedcure BMS (4-[(4-methylphenyl)sulfanyl]-benzophenone; 0.001% w/v in methanol, 1 cm path length; bold black line) and of Speedcure MBP (4-methylbenzophenone; 0.001% w/v in methanol, 1 cm path length; thin dotted line). Illustrating the advantage of having a heteroatom, here —S—, in the para-position adjacent of a photoinitiator moiety.

Figure 2:
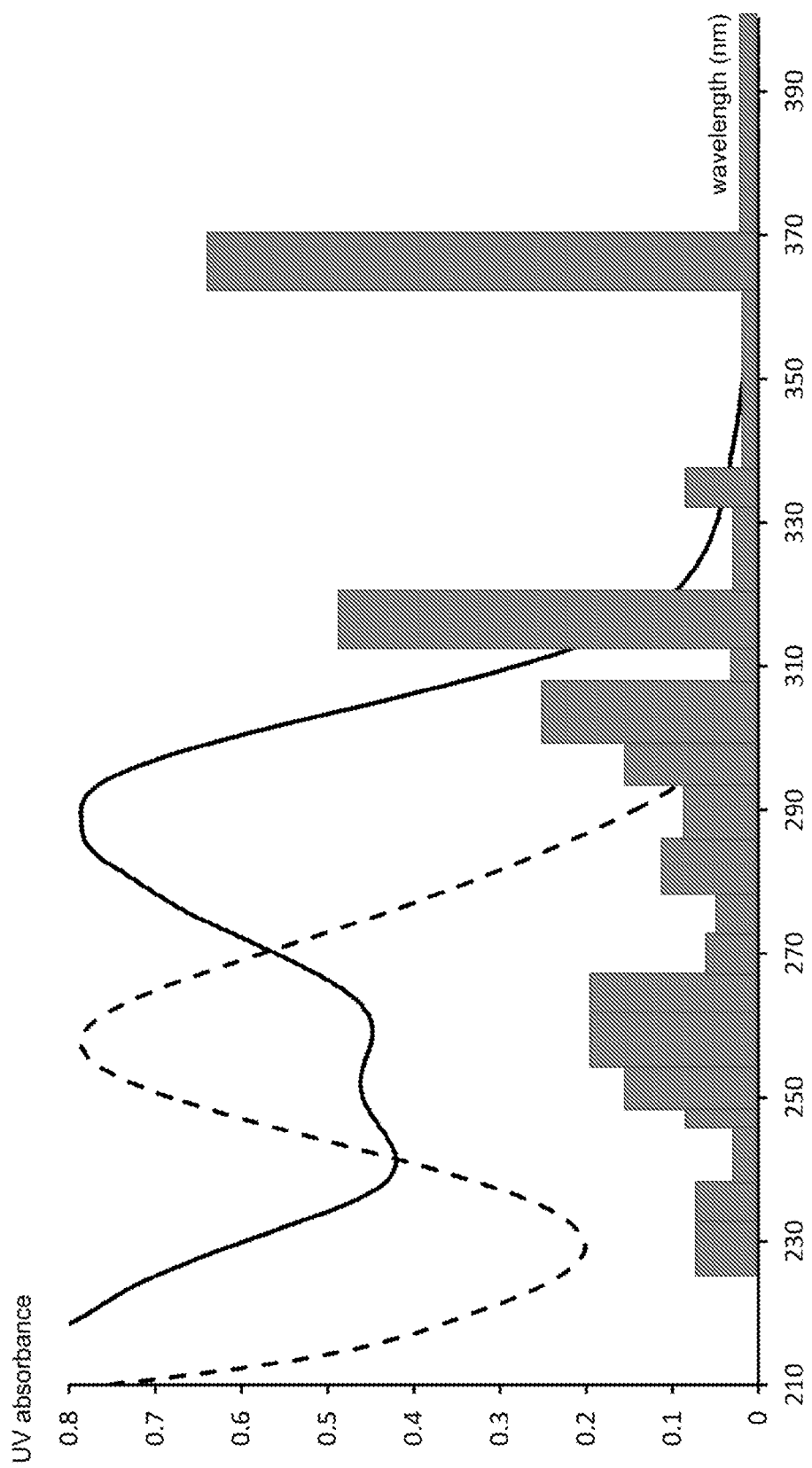

FIG. 2: shows the UV absorption spectra of 3-(4-benzoylphenoxy)propane-1,2-diol, Example 7, (bold black line) and of 1,3-diethyl 2-[(4-benzoylphenyl)methyl]propanedioate, Example 8, (dashed line). The UV spectra output lines of a standard medium-pressure mercury H lamp are shown as a grey bar chart. Larger overall overlap of the mercury lamp spectral output with the absorption spectrum of 3-(4-benzoylphenoxy)propane-1,2-diol illustrates the advantage of having a heteroatom, here —O—, in the para-position adjacent of a photoinitiator moiety.

DETAILED DISCLOSURE OF THE INVENTION

Polymeric photoinitiators being copolymers of monomer (A) of formula (I) provide the means for efficient curing of polymeric materials, such as for example coatings on, or materials in, medical devices, paints, or lacquers. The photoinitiator monomers of the present invention by their two functional groups, allow for incorporation by covalent bonds into the polymeric materials, hereby limiting or even preventing the migration of the photoinitiator itself. The photoinitiator monomers and polymeric photoinitiators of the present invention additionally provide the means for limiting the migration of by-products as they are especially stable, both in the incorporated linker and in the functional group moieties that take part in polymerisation reactions. In this manner any moisture or water initiated hydrolysis otherwise observed during storage of a final polymer or a product having incorporated the final polymer may be limited.

The present photoinitiator monomers and polymeric photoinitiators are hereby specially suited for medical purposes where special considerations in this regard are to be made, both in relation to patient health and regulatory approvals.

The photoinitiator monomers and polymeric photoinitiators of the present invention are useful in connection with a wide variety of polymers, such as for example polyurethanes, polyureas, polythiourethanes, polythioureas, polydithiourethanes, polyesters, polyethers, polycarbonates, polyphosphonites, polyphosphonates and polyphosphates.

The present inventors have found that it is especially preferred to use the photoinitiator monomers of the invention in polyesters and polyethers. The relevant monomers having e.g. primary or secondary alcohols, carboxylic acids or carboxylic acid esters as the functional group allow for polymerisation reactions under harsh chemical conditions typically used in industrial scale production. Strong acids like mineral acids, titanium alkoxides or dialkyltin oxides are typically used in preparation of polymeric polyesters, and strong base like alkali metal hydroxides or carbonates are typically used in preparation of polyethers, in both cases under high temperatures. This would lead to hydrolysis of a wide range of compounds. Additionally, the absence of primary, secondary or tertiary amines avoids neutralisation of the necessary acids for such polymerisation reactions.

The photoinitiator monomers of the present invention having two functional groups provide an advantage when used in polymerization into the above polymers, as two or more different types of monomers may be used in forming a linear polymer chain. Hereby allowing for fine tuning and variation of the physical and chemical properties of the obtained polymers when, for example, more hydrophobic or more hydrophilic polymers may be desired. The later may be obtained by inserting linkers or varying the polymer chain with co-monomers, which e.g. enhance and stabilize hydrogen bonding giving better adhesion of the polymer to polar surfaces. This is especially of relevance when a polymeric polyurethane is to be used as a coating on top of another polyurethane material, hereby giving good adhesion and subsequent good cross-linking, binding the two materials together.

As an example of such a polymeric polyurethane photoinitiator can be mentioned a polyurethane having incorporated polyalkylether chain segments. In the definition of the polymeric photoinitiators of the invention, such a polymer may correspond to a monomer (A) being of formula (I), a monomer (B) being a diisocyanate and one or more additional monomers (C) being a polyalkylether macromonomer, e.g. a polypropylene glycol or a polyethylene glycol (PEG), such as PEG 400, PEG 2000, PEG 4000 etc. Further details about suitable monomer (C) are described herein elsewhere. Two examples of polymeric polyurethane photoinitiators of the present invention incorporating three different monomers can be seen from Scheme 1. In these non-limiting examples every unit of monomer (A) bearing a photoinitiator moiety is flanked by two diisocyanate monomer units (B). Similarly, every unit of monomer (C) in the polymer chain is flanked by two diisocyanate monomer units (B). Thus, the polymer chain is built from randomly interspersed -A-B— and —C—B— units. For example, the polymer chain may contain the following sequence of monomer units -A-B—C—B—C—B-A-B—C—B-A-B-A-B—C—B—C—B—C—B-A-B—. In this manner bonds between monomeric units A and B; C and B are formed by the urethane (carbamate) links —NH—(C=O)—O—.

In Scheme 1, x may be an integer equal to 1 or greater, preferably, x is between 1 and 100; independently, y may be zero or an integer equal to 1 or greater, preferably, y is between 1 and 100; independently, z may be an integer equal to 1 or greater, preferably, z is between 2 and 10000.

Scheme 1

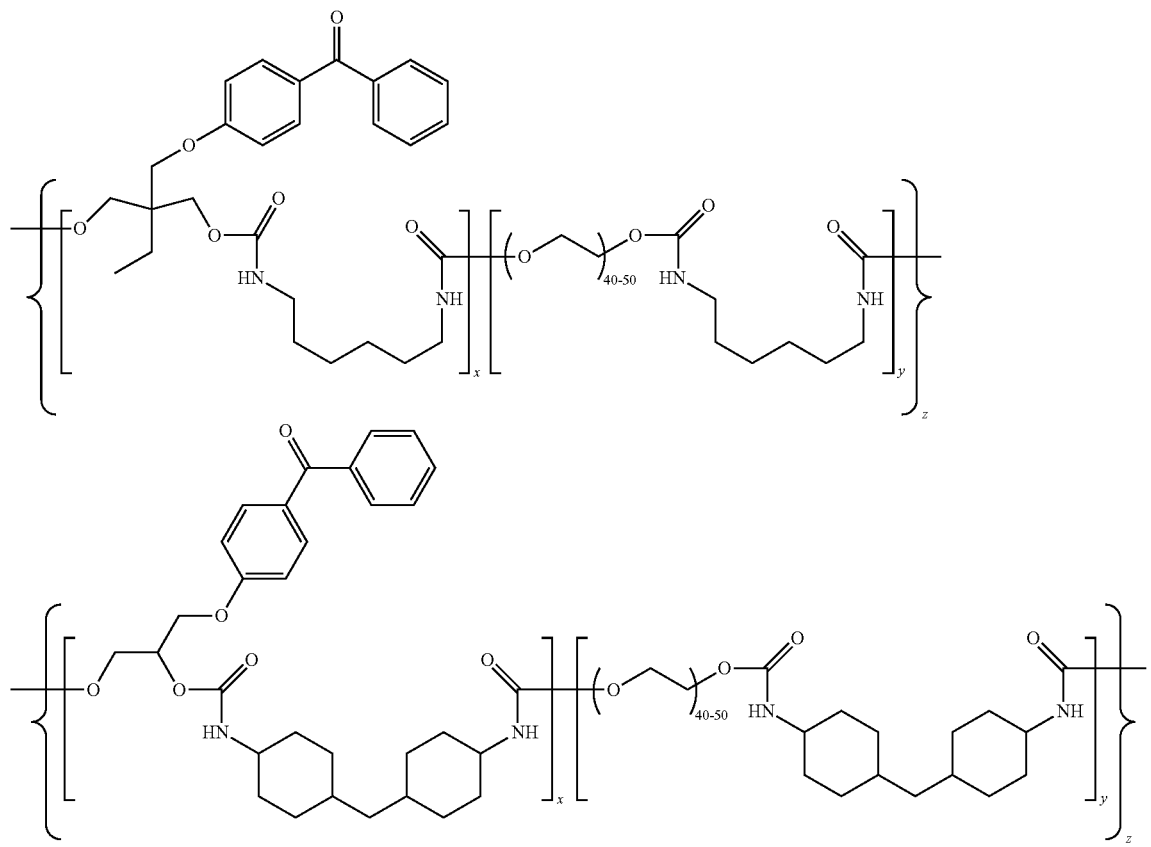

This possibility of variation is in contrast to known copolymerisable unsaturated photoinitiator monomers having e.g. one vinylic functional group. Such variety of properties of polymeric photoinitiators may be difficult to achieve when these are constructed from polymer backbones containing only carbon-carbon bonds (e.g. polyacrylates). Despite the fact that many examples of polymeric photoinitiators based on radical co-polymerisation of acrylic monomers (Macromolecules 2012, 45(12), 5237-5246) have been reported in the literature, such approach suffers from disadvantages. Often, radical co-polymerisation of different monomers mixed in a particular ratio does not provide a polymeric chain in which all the co-monomers are randomly interspersed in the same ratio. This is due to variations in the propagation rate for the different co-monomers. As a result, one of the co-monomers may be left largely unreacted at the end of the polymerisation reaction, or a block co-polymer is obtained, in which the less reactive co-monomer units are concentrated around the polymer end rather than randomly distributed throughout the whole polymer chain A further example of a polymeric photoinitiator of the invention having incorporated a polyalkylether chain segment, is a polymeric polyether photoinitiator. In the definition of the polymeric photoinitiators of the invention such a polymer may correspond to a monomer (A) being of formula (I) and a monomer (B) being a polyalkylether macromonomer e.g. a polypropylene glycol or a polyethylene glycol (PEG), such as PEG 400, PEG 2000, PEG 4000 etc., wherein the macromonomer for instance may be functionalised as a dimesylate or diiodide for incorporation. Further details about suitable monomer (C) are described herein elsewhere. Two examples of a polymeric polyether photoinitiator of the invention can be seen from Scheme 2.

Scheme 2

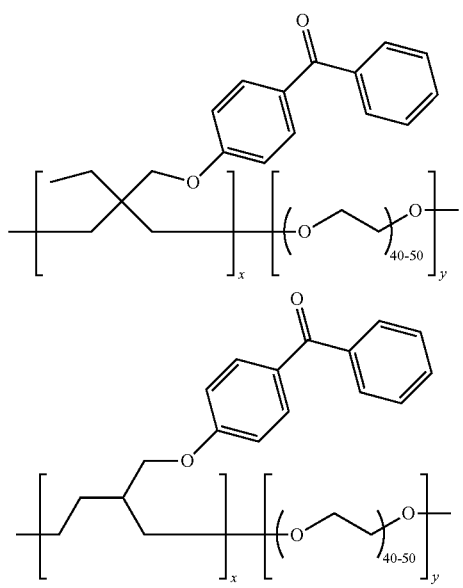

Polyurethanes

A polyurethane (PU) is a polymer consisting of a chain of organic units joined by urethane (carbamate) links —NH—(C=O)—O—. Polyurethanes are formed by the reaction between one monomer having at least two isocyanate functional groups (—NCO), and another monomer or macromonomer (e.g. a PEG) having at least two alcohol (—OH) groups. In their simplest form, due to the nature of the monomers from which they are prepared, polyurethanes comprise alternating A and B monomers (ABABABABA . . . ). In the first aspect of the present invention, monomer A may contain at least two —OH groups or two —NCO groups and hence participate in the formation of a polyurethane polymer.

A polyurethane according to the present invention may in this manner also be a polymer having such urethane links in the chain in between macromonomer moieties of e.g. polyether (see e.g. Scheme 1), polyester or polycarbonate. This may for example be the case when a polyurethane comprises A and B monomers and a C macromonomer, where A has two alcohol groups, B has two isocyanate groups, and C is a macromonomer having two terminal alcohol functional groups or two terminal isocyanate functional groups (giving e.g. ABCBABCBCBA when C has two alcohol groups). C could here for instance be a polyalkylether (e.g. PEG) or polyester having two terminal alcohol groups. In a preferred embodiment of the first aspect of the invention, the polymeric photoinitiator is a polyurethane.

Polythiourethanes

A polythiourethane is a generic name for polymers consisting of a chain of organic units joined by —NH—(C=O)—S— or —NH—(C=S)—O— links. The former type of polythiourethanes is formed by the reaction between one monomer having at least two isocyanate functional groups (—NCO), and another monomer having at least two thiol (—SH) groups. The latter type of polythiourethanes is formed by the reaction between one monomer having at least two isothiocyanate functional groups (—NCS), and another monomer having at least two alcohol (—OH) groups.

A polythiourethanes according to the present invention may in this manner also be a polymer having such —NH—(C=O)—S— or —NH—(C=S)—O— links in the chain in between macromonomer moieties of e.g. polyether or polydisulfide. This may for example be the case when a polythiourethane comprises monomers A, B and C, where A has two thiol (—SH) groups, B has two isocyanate groups, and C is a poly(ethylene glycol) dithiol pre-polymer having two free terminal thiol groups (giving e.g. ABCBABCBCBA) or C is an polyalkylether pre-polymer containing disulfide linkages (—S—S—) such as Thiokol® LP-32 or Thiokol® LP-33 two terminal thiol (—SH) functional groups (giving e.g. ABCBCBABCBCBA). The first case providing a polythiourethane polymer having both polythiourea moieties and polyalkylether moieties in the chain, and the later case providing a polymer having both polythiourea, polyalkylether and disulfide moieties in the chain.

Polythioureas

A polythiourea is a polymer consisting of a chain of organic units joined by thiourea (thiocarbamide) moieties —NH—(C=S)—NH—. Polyureas are typically formed by the reaction between one monomer having at least two isothiocyanate functional groups (—NCS), and another monomer having at least two amine (—NH$_2$) groups. Alternatively, polyureas can be formed by the reaction between one monomer having at least two amine (—NH$_2$) groups, and thiophosgene (S=CCl$_2$).

A polythiourea according to the present invention may in this manner also be a polymer having such thiourea moieties in the chain in between macromonomer moieties of e.g. polyether, polyester or polycarbonate. This may for example be the case when a polythiourea comprises A, B and C monomers, where A has two amine groups, B has two isothiocyanate groups, and C is a polyamine macromonomer having two free terminal amine groups (giving e.g. ABCBABCBCBA) or C is a polyalkylether macromer having two free functional hydroxyl groups (giving e.g. ABCBCBABCBCBA). The first case providing a polyurea polymer having both thiourea moieties and amine moieties in the chain, and the later case providing a polymer having both polythiourea, polyalkylether and polythiourethane moieties in the chain. For example, polyether macromonomer moieties are introduced into the main polymer chain when polyetheramines such as Jeffamine D-400, Jeffamine D-2000 or Jeffamine D-4000 etc. are used as macromonomers with two amine (—NH$_2$) groups. Polyester macromonomer moieties may be introduced into the main polymer chain when amine-terminated polyesters such as those disclosed in U.S. Pat. No. 5,525,683 are used.

Polydithiourethanes

A polydithiourethane is a polymer consisting of a chain of organic units joined by dithiourethane links —NH—(C=S)—S—. Polydithiolurethanes are typically formed by the reaction between one monomer having at least two isothiocyanate functional groups (—NCS), and another monomer having at least two thiol (—SH) groups.

A polydithiourethane according to the present invention may in this manner also be a polymer having such dithiourethane links in the chain in between macromonomer moieties of e.g. polyether or polydisulfide. This may for example be the case when a polydithiourethane comprises monomers A, B and C, where A has two thiol (—SH) groups, B has two isothiocyanate groups, and C is a poly(ethylene glycol) dithiol pre-polymer having two free terminal thiol groups (giving e.g. ABCBABCBCBA) or C is a polyalkylether prepolymer containing disulfide linkages (—S—S—) such as Thiokol® LP-32 or Thiokol® LP-33 two terminal thiol (—SH) functional groups (giving e.g. ABCBCBABCBCBA). The first example case providing a polydithiourethane polymer having both polydithiourea moieties and polyalkylether moieties in the chain, and the later case providing a polymer having both polydithiourea, polyalkylether and disulfide moieties in the chain.

Due to the characteristic sulphur smell that may be present in polythiourethanes or polydithiourethanes made from especially monomers with thiol groups, photoinitiator monomers with —SH or —CH$_2$SH are less desirable to use. Thus, one embodiment of the invention relates to polymeric photoinitiators from monomers (A) of formula (I) having no —SH or —CH$_2$SH moieties as the W$_1$ and/or W$_2$. Moreover, thiol moieties in such monomers are prone to aerial oxidation to disulfides and therefore have shorter shelf lives than analogous monomers with alcohol groups.

Polyesters

A polyester is a polymer consisting of a chain of organic units joined by ester moieties —(C=O)—O—. Polyesters are typically formed by the reaction between one monomer having at least two carboxylic functional groups which are either unactivated (i.e. —COOH or —COOR, where R is alkyl or aryl), or activated (—COO—X, where X is, e.g., a chloride or bromide), and another monomer having at least two alcohol (—OH) groups. The first reaction is an esterification reaction that proceeds in the presence of a Brønsted or Lewis acid catalyst with concomitant removal of water formed during the reaction. The second reaction is a transesterification reaction that proceeds in the presence of a Brønsted or Lewis acid catalyst with concomitant removal a volatile alcohol by-product formed during the reaction. The third reaction proceeds in the presence of a catalytic or stoichiometric quantity of a base such as trialkylamine. Alternatively, polyesters are prepared from monomers having one hydroxy and one —COOH (or —COOR) group. Polyesters can also be prepared by ring-opening polyesterification of cyclic lactones.

A polyester according to the present invention may in this manner also be a polymer having such ester moieties in the chain in between macromonomer moieties of e.g. a polyether. This may for example be the case when a polyester comprises A, B and C monomers, where A has two alcohol groups, B has two carboxylic acid groups, and C is a polyalkyl ether macromonomer having two terminal hydroxy groups (giving e.g. ABCBABCBCBA). This provides a polyester polymer having both ester moieties and polyether moieties in the chain. For example, polyether macromonomer moieties are introduced into the main polymer chain when polyalkylether, e.g. a polypropylene glycol or a polyethylene glycol (PEG), such as PEG 400, PEG 2000, PEG 4000 etc. are used as monomer C.

Polyethers

A polyether is a polymer consisting of a chain of organic units joined by ether moieties —O—. Polyethers are typically formed by reaction between one monomer having at least two alcohol or phenol —OH groups, and another monomer having at least two leaving groups (-LG) in the presence of a base.

A polyether according to the present invention may in this manner also be a polymer having such ether moieties incorporating the photoinitiator monomer in the chain in between macromonomer moieties of e.g. a polyether. This may for example be the case when a polyether comprises A and B monomers, where A has two alcohol —OH groups and B is a polyalkyl ether macromonomer having two terminal leaving groups. This provides a polyether polymer having two types of ether moieties in the chain. For example, polyether macromonomer moieties are introduced into the main polymer chain when polyalkylether with two terminal leaving groups, e.g. a polyethylene glycol (PEG) dibromide or dimesylate is used as monomer B.

Polycarbonate

A polycarbonate is a polymer consisting of a chain of organic units joined by carbonate moieties —O—(C=O)—O—. Polycarbonates are typically formed by the reaction between one monomer having at least two hydroxy functional groups (—OH), and another monomer having at least two chloroformate (—O—(C=O)—Cl) groups. Alternatively, polycarbonates can be formed by the reaction between one monomer having at least two hydroxy functional groups (—OH), and phosgene ($COCl_2$) or diphenyl carbonate (($PhO)_2CO$).

A polycarbonate according to the present invention may in this manner also be a polymer having such carbonate moieties in the chain in between macromonomer moieties of e.g. a polyester or polyamide. This may for example be the case when a polycarbonate comprises monomers A, B and C, where A has two alcohol (—OH) groups, B is ethylenebis(chloroformate), and C is a linear hydroxyl-terminated polyester macromonomer, such as Desmophen 850, (giving e.g. ABCBABCBCBA) or C is a hydroxyl-terminated linear polyamide macromonomer containing amide linkages (—C(O)—NH—) such as those disclosed in patent EPO449419 (giving e.g. ABCBCBABCBCBA). The first case providing a polycarbonate polymer having both carbonate moieties and polyester moieties in the chain, and the later case providing a polymer having both carbonate and amide moieties in the chain.

Polyphosphonites

A polyphosphonite is a polymer consisting of a chain of organic units joined by phosphonite links —O—P(R)—O—, where R is typically methyl or phenyl. Polyphosphonites are typically formed by the reaction between one monomer having at least one dichlorophosphine functional group (—$PCl_2$), or bis(diethylamino)phosphine group (—$P(NEt_2)_2$), and another monomer having at least two alcohol (—OH) groups.

Polyphosphonates

A polyphosphonate is a polymer consisting of a chain of organic units joined by phosphonate links —O—P(=O)(R)—O—, where R is typically methyl or phenyl. Polyphosphonates are typically formed by the reaction between one monomer having at least one phosphonoyl dichloride functional group (—P(=O)$Cl_2$), and another monomer having at least two alcohol (—OH) groups.

Polyphosphates

A polyphosphate is a polymer consisting of a chain of organic units joined by phosphate links —O—P(=O)(OR)—O—, where R is typically methyl or phenyl. Polyphosphates are typically formed by the reaction between one monomer having at least one phosphorodichloridate functional group (—O—P(=O)$Cl_2$), and another monomer having at least two alcohol (—OH) groups.

Curing

When using photoinitiator monomers or polymeric photoinitiators according to the present invention, curing is primarily initiated by exposing the photopolymerizable system containing the polymeric photoinitiators to high energy irradiation, preferably UV light. The photoinitiated process takes place by methods which are known per se, through irradiation with light or UV irradiation in the wavelength range from 100 to 800 nm, and more usually from 280-800 nm. Irradiation sources which may be used are sunlight or artificial lamps, lasers, or vacuum corona processes. Mercury high-pressure, medium pressure or low-pressure lamps and xenon and tungsten lamps, for example, are advantageous. Similarly, excimer, solid-state and diode-based lasers are advantageous. Diode-based light sources in general are advantageous for initiating the chemical reactions.

The ultraviolet spectrum is divided into A, B and C segments where UV A extend from 400 nm down to 315 nm, UV B from 315 to 280 nm, and UV C from 280 to 100 nm. By using a light source that generates light with wavelengths in the visible region (400 to 800 nm) some advantages are obtained with respect to the depth of the curing, provided that the photoinitiator can successfully cure the material at these wavelength. In particular, scattering phenomena are less pronounced at longer wavelength, thus giving a larger penetration depth in the material. Thus, photoinitiator moieties which absorb, and can induce curing, at longer wavelength are of interest. By judicially choosing substituents on the phenone moieties, the absorption spectrum of the photoinitiator can to some extent be red-shifted, which would then facilitate curing at comparatively greater depths.

Photoinitiator Monomers and Photoinitiator Moieties

The present invention provides photoinitiator monomers of general formula (Ia) together with polymeric photoinitiators being a co-polymer of at least one monomer (A) with at least one monomer (B). Said monomer (A) is a photoinitiator monomer of general formula (I):

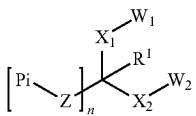
(I)

wherein:
Pi is a photoinitiator moiety;
Z is a linker moiety selected from a single bond, $C_1$-$C_{12}$ alkylene, $C_2$-$C_{12}$ alkenylene, $C_3$-$C_8$ cycloalkyl, aryl, heterocyclyl, —($C_1$-$C_{12}$ alkylene)-aryl-, -aryl-($C_1$-$C_{12}$ alkylene)-, —($C_1$-$C_{12}$ alkylene)-heterocyclyl-, -heterocyclyl-($C_1$-$C_{12}$ alkylene)-, —[O—($C_1$-$C_{12}$ alkylene)]$_m$-, —[S—($C_1$-$C_{12}$ alkylene)]$_m$-, —[($C_1$-$C_{12}$ alkylene)-O]$_m$—, —[($C_1$-$C_{12}$ alkylene)-S—]$_m$—, —[O—($C_1$-$C_{12}$ alkylene)]$_m$-O—, —[S—($C_1$-$C_{12}$ alkylene)]$_m$-S—, —[O—($C_1$-$C_{12}$ alkylene)]$_m$-S—, —[S—($C_1$-$C_{12}$ alkylene)]$_m$-O—; —C(=O)—, —[C(=O)—($C_1$-$C_{12}$ alkylene)]$_m$-, —[C(=O)-aryl]$_m$-, and —[C(=O)-heterocyclyl]$_m$-;
$R^1$ is selected from H, $C_1$-$C_{12}$ alkyl, $C_2$-$C_{12}$ alkenyl, $C_3$-$C_8$ cycloalkyl, aryl, heterocyclyl, —[O—($C_1$-$C_{12}$ alkylene)]$_m$-H, —[S—($C_1$-$C_{12}$ alkylene)]$_m$-H, —C(=O)—H, —[C(=O)—($C_1$-$C_{12}$ alkylene)]$_m$-H, —[C(=O)-aryl]$_m$-H and —[C(=O)-heterocyclyl]$_m$-H;
$X_1$ and $X_2$ are each independently selected from single bond, $C_1$-$C_{12}$ alkylene, $C_2$-$C_{12}$ alkenylene, $C_3$-$C_8$ cycloalkyl, aryl, heterocyclyl, —[O—($C_1$-$C_{12}$ alkylene)]$_p$, and —[S—($C_1$-$C_{12}$ alkylene)]$_p$;
wherein $X_1$, $X_2$, $R^1$ or Z each independently may be linked to one another to form one or more ring structures;
$W_1$ and $W_2$ are each independently selected from —OH, —CH$_2$OH, —COOH, —COOR$^2$, —COO-aryl, —SH, —CH$_2$SH, —NH$_2$, —NHR$^2$, —NCO, —NCS, —C(=O)—Cl, and —O—C(=O)—Cl;
$R^2$ is selected from optionally substituted $C_1$-$C_{12}$ alkyl and aryl;
m is an integer from 1-10;
n is an integer of 1 or 2, with the proviso that when n is 2, $R^1$ is absent;
p is an integer from 1-10; and
wherein any Pi, alkyl, alkenyl, alkylene, alkenylene, cycloalkyl, aryl, or heterocyclyl moiety each independently is optionally substituted with one or more substituents selected from —F, —Cl, —Br, —I, —CN, —NO$_2$, —$C_1$-$C_6$ alkyl, aryl, —O—($C_1$-$C_6$ alkyl), —S—($C_1$-$C_6$ alkyl), —S(O)—($C_1$-$C_6$ alkyl), and —SO$_2$—($C_1$-$C_6$ alkyl).

A preferred group of photoinitiator monomers that may be used in the polymeric photoinitiators of the invention is of general formula (Ia):

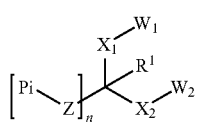
(Ia)

wherein:
Pi is a photoinitiator moiety;
Z is a linker moiety selected from a single bond, $C_1$-$C_{12}$ alkylene, $C_2$-$C_{12}$ alkenylene, $C_3$-$C_8$ cycloalkyl, aryl, heterocyclyl, —($C_1$-$C_{12}$ alkylene)-aryl-, -aryl-($C_1$-$C_{12}$ alkylene)-, —($C_1$-$C_{12}$ alkylene)-heterocyclyl-, -heterocyclyl-($C_1$-$C_{12}$ alkylene)-, —[O—($C_1$-$C_{12}$ alkylene)]$_m$-, —[S—($C_1$-$C_{12}$ alkylene)]$_m$-, —[($C_1$-$C_{12}$ alkylene)-O]$_m$—, —[($C_1$-$C_{12}$ alkylene)-S—]$_m$—, —[O—($C_1$-$C_{12}$ alkylene)]$_m$-O—, —[S—($C_1$-$C_{12}$ alkylene)]$_m$-S—, —[O—($C_1$-$C_{12}$ alkylene)]$_m$-S—, —[S—($C_1$-$C_{12}$ alkylene)]$_m$-O—; —C(=O)—, —[C(=O)—($C_1$-$C_{12}$ alkylene)]$_m$-, —[C(=O)-aryl]$_m$-, and —[C(=O)-heterocyclyl]$_m$-;
$R^1$ is selected from H, $C_1$-$C_{12}$ alkyl, $C_2$-$C_{12}$ alkenyl, $C_3$-$C_8$ cycloalkyl, aryl, heterocyclyl, —[O—($C_1$-$C_{12}$ alkylene)]$_m$-H, —[S—($C_1$-$C_{12}$ alkylene)]$_m$-H, —C(=O)—H, —[C(=O)—($C_1$-$C_{12}$ alkylene)]$_m$-H, —[C(=O)-aryl]$_m$-H and —[C(=O)-heterocyclyl]$_m$-H;
$X_1$ and $X_2$ are the same and are selected from single bond, $C_1$-$C_{12}$ alkylene, $C_2$-$C_{12}$ alkenylene, $C_3$-$C_8$ cycloalkyl, aryl, heterocyclyl, —[O—($C_1$-$C_{12}$ alkylene)]$_p$, and —[S—($C_1$-$C_{12}$ alkylene)]$_p$;
wherein $X_1$, $X_2$, $R^1$ or Z each independently may be linked to one another to form one or more ring structures;
$W_1$ and $W_2$ are the same and are selected from —OH, —CH$_2$OH, —COOH, —COOR$^2$, —COO-aryl, —NH$_2$, —NHR$^2$, —NCO, —NCS, —C(=O)—Cl, and —O—C(=O)—Cl;
$R^2$ is selected from optionally substituted $C_1$-$C_{12}$ alkyl and aryl;
m is an integer from 1-10;
n is an integer of 1 or 2, with the proviso that when n is 2, $R^1$ is absent;
p is an integer from 1-10; and
wherein any Pi, alkyl, alkenyl, alkylene, alkenylene, cycloalkyl, aryl, or heterocyclyl moiety each independently is optionally substituted with one or more substituents selected from —F, —Cl, —Br, —I, —CN, —NO$_2$, —$C_1$-$C_6$ alkyl, aryl, —O—($C_1$-$C_6$ alkyl), —S—($C_1$-$C_6$ alkyl), —S(O)—($C_1$-$C_6$ alkyl), and —SO$_2$—($C_1$-$C_6$ alkyl);
with the proviso that the photoinitiator monomer is not
1,3-diethyl 2-[(3-benzoylphenyl)methyl]propanedioate,
1,3-diethyl 2-({3-[(4-chlorophenyl)carbonyl]phenyl}methyl)propanedioate,
1,3-diethyl 2-[(3-benzoyl-2-methoxyphenyl)methyl]propanedioate,
2-[(3-benzoyl-2-methoxyphenyl)methyl]propanedioic acid, or
1,3-dimethyl 2-[(9,10-dioxo-9,10-dihydoanthracen-2-yl)methyl]propanedioate.

In formula (I) and formula (Ia)—the latter being a subformula of formula (I)—it is to be understood that the linker moiety Z is attached to Pi at one end and to the branching carbon atom of formula (I) or (Ia) at the other end. The direction of Z between Pi and said branching carbon atom, is as it is written, i.e. the left side of the indicated linker moiety is attached to Pi and the right hand side is attached to the branching carbon atom. Additionally, it is to be understood, that when n is 2, the then two groups Pi-Z— are both attached to the branching carbon atom (i.e. connecting Z with —$X_1$—$W_1$ and —$X_2$—$W_2$, the C-atom is not written in formula (I)), and the $R^1$ groups is then absent.

U.S. Pat. No. 3,931,302 relates to compounds having anti-inflammatory and analgesic activity. Disclosed therein are Example I, Step a: 1,3-diethyl 2-[(3-benzoylphenyl)methyl]propanedioate, Example XIII, Step a: 1,3-diethyl 2-({3-[(4-chlorophenyl)carbonyl]phenyl}methyl)propanedioate, Example XXVI, Step c: 1,3-diethyl 2-[(3-benzoyl-2-methoxyphenyl)methyl]propanedioate, and Example XXVI, Step d: 2-[(3-benzoyl-2-methoxyphenyl)methyl]propanedioic acid which by chance resembles photoinitiator monomers of the present invention, and which are disclaimed from the scope of the photoinitiator monomers of formula (Ia). Further disclosed therein are Example XVI, Step e: ethyl 4-(3-benzoylphenyl)-3-hydroxybutanoate, Example XVII: 4-(3-benzoylphenyl)-3-hydroxybutanoic acid, Example XIX, Step f: ethyl 4-(3-benzoylphenyl)-3-hydroxypentanoate, and Example XX: 4-(3-benzoylphenyl)-3-hydroxypentanoic acid having two different functional groups. There are not mentioned or suggested any use of any of the described compounds in co-polymerisation of polymeric photoinitiators. The compounds by chance resembles photoinitiator monomers of formula (I), and thus in one embodiment of the polymeric photoinitiators of the invention, photoinitiator monomer (A) of formula (I) is not 1,3-diethyl 2-[(3-benzoylphenyl)methyl]propanedioate, 1,3-diethyl 2-({3-[(4-chlorophenyl)carbonyl]phenyl}methyl)propanedioate, 1,3-diethyl 2-[(3-benzoyl-2-methoxyphenyl)methyl]propanedioate, 2-[(3-benzoyl-2-methoxyphenyl)methyl]propanedioic acid, ethyl 4-(3-benzoylphenyl)-3-hydroxybutanoate, 4-(3-benzoylphenyl)-3-hydroxybutanoic acid, ethyl 4-(3-benzoylphenyl)-3-hydroxypentanoate, or 4-(3-benzoylphenyl)-3-hydroxypentanoic acid.

An article by Mesmaeker et al. (Bioorganic and Med. Chem. Letters, vol. 7, No. 14, pp. 1869-1874, 1997) has disclosed amide modified oligonucleotides with anti-lipaemic and anti-cholesterolemic pharmacological activity. The synthetic route to the modified oligonucleotides goes via a compound 11, 1,3-dimethyl 2-[(9,10-dioxo-9,10-dihydoanthracen-2-yl)methyl]propanedioate, which is disclaimed from the scope of the photoinitiator monomers of formula (Ia). There are not mentioned or suggested any use of this intermediate in co-polymerisation of polymeric photoinitiators. The compound by chance resembles photoinitiator monomers of formula (I), and thus in one embodiment of the polymeric photoinitiators of the invention, photoinitiator monomer (A) of formula (I) is not 1,3-dimethyl 2-[(9,10-dioxo-9,10-dihydoanthracen-2-yl)methyl]propanedioate.

An article by Hatsuda et al. (Arg. Biol. Chem., Vol. 33, No. 1, p. 131-133, 1969) has previously disclosed four new metabolites from *Aspergillus versicolor*. There are not mentioned or suggested any use of these in, or in relation to polymeric photoinitiators. Compound I: 2-(1,4-dihydroxybutan-2-yl)-1,3,6,8-tetrahydroxy-9,10-dihydroxyanthracene-9,10-dione could be considered as having the 9,10-dihydroxyanthracene-9,10-dione resembling a Pi, Z being a single bond attached at the para position, one of $—X_1W_1$ or $—X_2W_2$ being $—CH_2OH$, the other being $—CH_2CH_2OH$, and it is therefore disclaimed from the present invention. The ortho and para hydroxy substituents on the anthracene of compound I actually prevent it from acting as a photoinitiator. Compound III by chance resembles photoinitiator monomers of formula (I), and thus in one embodiment of the polymeric photoinitiators of the invention, photoinitiator monomer (A) of formula (I) is not 2-(1,4-dihydroxybutan-2-yl)-1,3,6,8-tetramethoxy-9,10-dihydroxyanthracene-9,10-dione.

U.S. Pat. No. 4,296,125 relates to compounds having an anti-lipaemic and anti-cholesterolemic pharmacological activity. There are not mentioned or suggested any relation to polymeric photoinitiators. Disclosed therein are Examples 25 and 28 which by chance resembles photoinitiator monomers of formula (I), each having one hydroxyl and one ester or acid functional group, respectively. In one embodiment of the polymeric photoinitiators of the invention, photoinitiator monomer (A) of formula (I) is not ethyl 2-[4-(4-chlorobenzoyl)phenoxy]-3-hydroxy-2-methylpropanoate or 2-[4-(4-chlorobenzoyl)phenoxy]-3-hydroxy-2-methylpropanoic acid.

A photoinitiator is defined as a substance which, on absorption of light, generates reactive species (ions or radicals) and initiates one or several chemical reactions or transformation. One preferred property of the photoinitiator is good overlap between the emission spectrum of the UV light source and the absorption spectrum of the photoinitiator. Another desired property is a minor or no overlap between the photoinitiator absorption spectrum and the intrinsic combined absorption spectrum of the other components in the polymer matrix. Good compatibility of the photoinitiator with the matrix consisting of material to be cured is also a property of interest.

The photoinitiator monomers with the general formula (I), and subformula thereof, comprise a photoinitiator moiety, Pi, which provides the photoinitiators with the required response to UV radiation.

The photoinitiator moieties of the invention are efficient in transforming light from the UV or visible light source to reactive radicals which can abstract hydrogen atoms and other labile atoms from polymers and hence effect polymerization and cross-linking.

Radical photoinitiator moieties can be classified as either cleavable (Norrish type I reaction) or non-cleavable (of which the Norrish type II reaction is a special case, see e.g. A. Gilbert, J. Baggott: "Essentials of Molecular Photochemistry", Blackwell, London, 1991). Upon excitation, cleavable photoinitiator moieties spontaneously break down into two radicals, at least one of which is reactive enough to abstract a hydrogen atom from most substrates. Benzoin ethers (including benzil dialkyl ketals), phenyl hydroxyalkyl ketones and phenyl aminoalkyl ketones are important examples of cleavable photoinitiator moieties. Addition of electron donors is not required but may enhance the overall efficiency of cleavable photoinitiator moieties.

Excited non-cleavable photoinitiator moieties do not break down to radicals but abstract a hydrogen atom from an organic molecule or, more efficiently, abstract an electron from an electron donor (such as an amine or a thiol). The electron transfer produces a radical anion on the photo-initiator and a radical cation on the electron donor. This is followed by proton transfer from the radical cation to the radical anion to produce two uncharged radicals; of these the radical on the electron donor is sufficiently reactive to abstract a hydrogen atom from most substrates. When a non-cleavable photoinitiator moiety is covalently attached as a pendant group via a linker to a polymer chain, there are, in principle, three pathways to form new carbon-carbon bond cross-links as a result of UV irradiation: 1) Coupling of ketyl and aliphatic radicals, 2) dimerisation of ketyl radicals to form a benzopinacol, 3) dimerisation of aliphatic radicals. In cases where the polymeric photoinitiator is a polyurethane with in-chain polyether macromonomer moieties, the hydrogen atom could for instance be abstracted from a $—CH_2—O—$ group within the main polymer chain (forming a reactive $—CH—O—$ radical).

Benzophenones and related ketones such as thioxanthones, xanthones, anthraquinones, fluorenones, dibenzosuberones, benzils, and phenyl ketocoumarins are important examples of non-cleavable photoinitiators, and fall within the definition of photoinitiator moieties according to the present invention. Most amines with a C—H bond in α-position to the nitrogen atom and many thiols will work as electron donors. In a preferred embodiment of the invention, Pi of general formula (I) is a non-cleavable photoinitiator, more preferably a Norrish type II photoinitiator. This due to the goal of the present invention to provide photoinitiator monomers of formula (I) where the migration of by-products from the final polymer product is avoided or at least considerably decreased.

Another self-initiating system based on maleimides has also been identified by C. K. Nguyen, W. Kuang, and C. A. Brady from Albemarle Corporation and Brady Associates LLC, both USA (2003): "Maleimide Reactive Oligomers", Proceedings from RadTech Europe 03, Berlin, Germany, Nov. 3-5, 2003, vol. 1, p. 589-94, Vincentz. Maleimides initiate radical polymerization mainly by acting as non-cleavable photo-initiators and at the same time spontaneously polymerize by radical addition across the maleimide double bond. In addition, the strong UV absorption of the maleimide disappears in the polymer, i.e. maleimide is a photobleaching photoinitiator moiety; this could make it possible to cure thick layers. However, as the maleimides in themselves are very reactive, undesired side-reactions may occur and therefore in some embodiments of the present invention the Pi of formula (I) does not include maleimides either alone or when mentioned herein in groups of Pi.

A blend of several photoinitiator moieties may exhibit synergistic properties, as is e.g. described by J. P. Fouassier: "Excited-State Reactivity in Radical Polymerization Photoinitiators", Ch. 1, pp. 1-61, in "Radiation curing in Polymer Science and technology", Vol. II ("Photo-initiating Systems"), ed. by J. P. Fouassier and J. F. Rabek, Elsevier, London, 1993. Briefly, efficient energy transfer or electron transfer takes place from one photoinitiator moiety to the other in the pairs [4,4'-bis(dimethylamino)benzophenone+benzophenone], [benzophenone+2,4,6-trimethyl-benzophenone], [thioxanthone+methylthiophenyl morpholinoalkyl ketone]. However, many other beneficial combinations may be envisaged. So, in an embodiment of the invention, the photoinitiator moiety Pi includes at least two different types of photoinitiator moieties. In one embodiment of the invention, the polymeric photoinitiator comprises at least two different types of photoinitiator moieties, these may be attached to the same or different monomers (A), preferably these may be attached to two different monomer (A) molecules. Preferably, the absorbance peaks of the different photoinitiator moieties are at different wavelengths, so the total amount of light absorbed by the system increases. The different photoinitiator moieties may be all cleavable, all non-cleavable, or a mixture of cleavable and non-cleavable. Preferably, however, the photoinitiator Pi comprises only one photoinitiator moiety.

UV self-crosslinkable terpolymers based on acrylonitrile, methyl acrylate and a UV sensitive comonomer, acryloyl benzophenone (ABP), have also been reported (A. K. Naskar et al. Carbon 43 (2005) 1065-1072; T. Mukundan et al. Polymer 47 (2006) 4163-4171). The free radicals generated during UV irradiation of the terpolymer have been shown to enhance crosslinking and cyclization of nitrile units within the polymer.

Furthermore, it has recently been found that covalently linked 2-hydroxy-1-(4-(2-hydroxyethoxy)phenyl)-2-methylpropan-1-one, which is commercially available with the trade name Irgacure 2959, and benzophenone in the molecule 4-(4-benzoylphenoxy ethoxy)phenyl 2-hydroxy-2-propyl ketone gives considerably higher initiation efficiency of radical polymerization than a simple mixture of the two separate compounds, see S. Kopeinig and R. Liska from Vienna University of Technology, Austria (2005): "Further Covalently Bonded Photoinitiators", Proceedings from RadTech Europe 05, Barcelona, Spain, Oct. 18-20 2005, vol. 2, p. 375-81, Vincentz. This shows that different photoinitiator moieties may show significant synergistic effects when they are present in the same oligomer or polymer. Such covalently linked photoinitiator moieties are also within the scope of the present invention.

Photoinitiator moieties (Pi) in Formula (I) may be selected from, but not exclusively restricted to, the group consisting of benzoin ethers, phenyl hydroxyalkyl ketones, phenyl aminoalkyl ketones, benzophenones, thioxanthones, xanthones, acridones, anthraquinones, fluorenones, dibenzosuberones, benzils, benzil ketals, α-dialkoxy-acetophenones, α-hydroxy-alkyl-phenones, α-amino-alkyl-phenones, acyl-phosphine oxides, phenyl ketocoumarins, camphorquinones, silane and derivatives thereof, and maleimides. Of these, preferred photoinitiator moieties may be selected from benzophenones, thioxanthones, benzilketals and phenyl hydroxyalkyl ketones, such as 2-hydroxy-2-methyl-1-phenylpropan-1-ones. More preferred photoinitiator moieties may be selected from benzophenones and thioxanthones.

In particular the photoinitiator monomers of the invention may have the general formula (II):

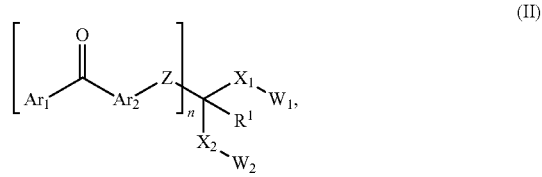

wherein $Ar_1$ and $Ar_2$ are independently selected from the same or different aryl, where Z may be present at any position on $Ar_2$, i.e. ortho-, meta- or para-position, where each aromatic ring is independently optionally substituted with one or more substituents selected from —F, —Cl, —Br, —I, —CN, —$NO_2$, —$C_1$-$C_6$ alkyl, —$C_2$-$C_6$ alkenyl, —$C_3$-$C_6$ cycloalkyl, aryl, heterocyclyl, —O—($C_1$-$C_6$ alkyl), —O—$C_3$-$C_8$ cycloalkyl, —O-aryl, —C(O)—($R^3$), —C(O)-aryl, —N($C_1$-$C_6$ alkyl)$_2$, —N($C_1$-$C_6$ alkyl)($C_3$-$C_6$ cycloalkyl), —N($C_1$-$C_6$ alkyl)(aryl), —N(aryl)$_2$, —S(O)—($C_1$-$C_6$ alkyl), —S(O)-aryl, —$SO_2$—($C_1$-$C_6$ alkyl), —$SO_2$-aryl, —S—($C_1$-$C_6$ alkyl), and —S-aryl; wherein $R^3$ is H or $C_1$-$C_6$ alkyl.

In a preferred embodiment of the invention the one or more optional substituents are independently selected from the group consisting of —F, —Cl, —Br, —I, —CN, —$NO_2$, —$C_1$-$C_6$ alkyl, aryl, —O—($C_1$-$C_6$ alkyl), —S—($C_1$-$C_6$ alkyl), —S(O)—($C_1$-$C_6$ alkyl), and —$SO_2$—($C_1$-$C_6$ alkyl).

Structures like those of formula (II) wherein either or both of $Ar_1$ and $Ar_2$ are substituted in the ortho- or para-position with —OH or —$NH_2$ are known as UV absorbers, giving too low triplet quantum yields ($\Phi_T$), for use as photoinitiators for practical purposes. Additionally, secondary amines (—NH—R) in the ortho- or para-position gives low triplet quantum yields in polar solvents, being less efficient photoinitiators (see Singh et al. J. Phys. Chem. A 104, 2000, 7002; Suppan et al. J. Photochem. Photobiol. A 94, 1996, 145). Accordingly, Pi in general formula (I) herein does not include compounds of formula (II) having one or more —OH or —$NH_2$ groups in the ortho- or para-position of the aryl rings. Additionally, in one embodiment of the invention photoinitiator monomers of formula (II) does not have a secondary amine (—NHR, where R e.g. is an alkyl group) in the ortho- or para-position of the aryl rings.

Suitably, $Ar_1$ and $Ar_2$ are the same. Preferably $Ar_1$ and $Ar_2$ each independently may be optionally substituted phenyl, where the phenyl each independently may be optionally substituted with one or more substituents selected from the herein immediately above specified group of substituents; and even more preferably both phenyl (i.e. unsubstituted).

In one preferred embodiment of the invention, Z is attached at the para-position on $Ar_2$, as this provides the maximum opportunity for electron interaction with the carbonyl group, and hence maximum stabilisation of the radical formed. In another preferred embodiment of the invention, Z is attached at the ortho-position on $Ar_2$.

Benzophenones are well-studied, commercially-available photoinitiator moieties, and their UV absorption can be tailored according to the substitution pattern of the aryl groups. Preferred substituents on $Ar_1$ and $Ar_2$ are electron-donating groups or atoms such as N, O and S. Such substituents provide UV absorption at a longer wavelength, meaning that LED lamps can be used as a UV source. LED lamps provide advantages such as low energy consumption and generate less heat; thus the substrate temperature can be controlled more accurately. Accordingly, in a preferred embodiment of the invention $Ar_1$ and $Ar_2$ may each independently optionally be substituted with one or more electron-donating groups or atoms; more preferably such one or more substituents, e.g. one, two, three or four substituents, may be selected from the group consisting of —$CH_3$, —$CH_2CH_3$, —$CH_2CH_2CH_3$, —$CH(CH_3)_2$, —$C_6H_5$, —$OCH_3$, —$OCH_2CH_3$, —$OCH_2CH_2CH_3$, —$OCH(CH_3)_2$, —$OC_6H_5$, —$SCH_3$, —$SCH_2CH_3$, —$SCH_2CH_2CH_3$, —$SCH(CH_3)_2$, —$SC_6H_5$, —$N(CH_3)_2$, —$N(CH_2CH_3)_2$, and —$N(CH_2CH_2OCH_2CH_2)_2$. Even more preferably such one or more substituents may be selected from the group consisting of —$CH_3$, —$CH_2CH_3$, —$CH_2CH_2CH_3$, —$CH(CH_3)_2$, —$C_6H_5$, —$OCH_3$, —$OCH_2CH_3$, —$OCH_2CH_2CH_3$, —$OCH(CH_3)_2$, —$OC_6H_5$, —$SCH_3$, —$SCH_2CH_3$, —$SCH_2CH_2CH_3$, —$SCH(CH_3)_2$, and —$SC_6H_5$. By not having any amines in the photoinitiator it may be used in polymerisation reactions requiring strong acids, such as sulphuric acid or arenesulfonic acids to be used. The presence of amines would otherwise neutralise the acid reagent.

A sub-structure which describes photoinitiator monomers of Formula (I) has the general formula (III), wherein $Ar_1$ and $Ar_2$ together form a benzophenone:

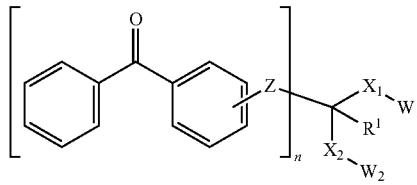

(III)

wherein Z may be attached at any position on the phenyl rings, and Z, n, $R^1$, $X_1$, $X_2$, $W_1$ and $W_2$, and preferred options for these groups, are as defined herein, and the phenyl rings are each independently optionally substituted.

Another sub-structure which describes photoinitiator monomers of Formula (I), has the general formula (IIIa):

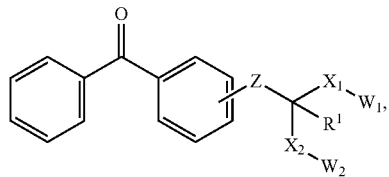

(IIIa)

wherein Z may be attached at any position on the phenyl ring, and Z, $R^1$, $X_1$, $X_2$, $W_1$ and $W_2$, and preferred options for these groups, are as defined herein, and the phenyl rings are each independently optionally substituted.

A further sub-structure which describes photoinitiator monomers of Formula (I) has the general formula (IIIb):

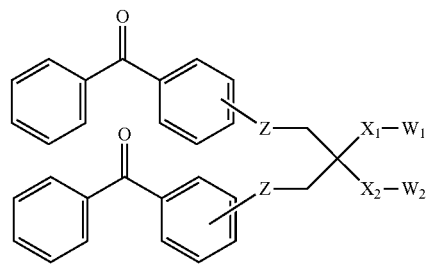

(IIIb)

wherein Z may be attached at any position on the phenyl ring, and Z, $R^1$, $X_1$, $X_2$, $W_1$ and $W_2$, and preferred options of these, are as defined herein, and the phenyl rings are each independently optionally substituted.

A sub-structure which describes photoinititiators of Formula (I) has the general formula (IV), wherein $Ar_1$ and $Ar_2$ together form a thioxanthone:

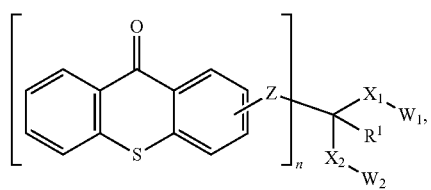

(IV)

wherein Z may be attached at any position on the aryl ring, and Z, n, $R^1$, $X_1$, $X_2$, $W_1$ and $W_2$, and preferred options of these, are as defined herein, and the aryl rings each independently are optionally substituted.

Another sub-structure which describes photoinitiator monomers of Formula (I) has the general formula (IVa):

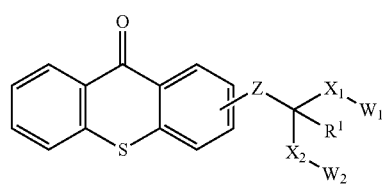

(IVa)

wherein Z may be attached at any position on the aryl ring, and Z, $R^1$, $X_1$, $X_2$, $W_1$ and $W_2$, are as defined herein, and the aryl rings each independently are optionally substituted.

A further sub-structure which describes photoinitiator monomers of Formula (I) has the general formula (IVb):

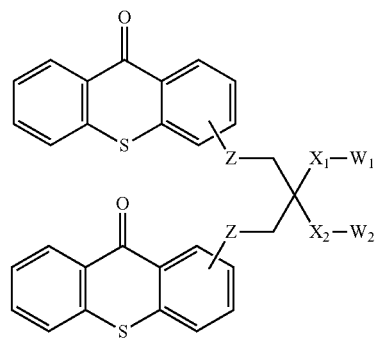

(IVb)

wherein Z may be attached at any position on the phenyl ring, and Z, $R^1$, $X_1$, $X_2$, $W_1$ and $W_2$, and preferred options of these, are as defined herein, and the aryl rings are each independently optionally substituted.

In formulas (III), (IIIa), (IIIb), (IV), (IVa), and (IVb), Z may be attached at any position, i.e. ortho-, meta- or para-position to the carbonyl group (the attachment point is indicated in the formulas by the unattached bond of Z), and where each aromatic ring independently may be optionally substituted with one or more substituents selected from the group specified herein above for formula (II). Preferably Z may be present at the para-position to the carbonyl group.

Another sub-structure which describes photoinitiator monomers of Formula (I) has the general formula (IIIc):

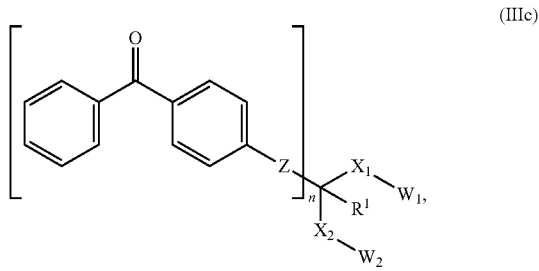

(IIIc)

wherein Z, n, $X_1$, $X_2$, $W_1$ and $W_2$, and preferred options for these groups, are as defined herein, and the phenyl rings are each independently optionally substituted.

Judicious selection of functional groups can be used to obtain absorption maxima in a desired wavelength region (e.g. impart positive mesomeric effect within the photoinitiator). The ketones described in the present invention are inherent electron accepting groups, so careful selection of electron-donating groups as substituents on aromatic rings within the photoinitiator can lead to absorption profiles matching the light source best suited for the desired curing application. Mechanistically, the efficiency of photoinitiators relies on their ability to intersystem cross from an electronic excited (singlet) state to a triplet state. Some literature has described that such intersystem crossing is less efficient when a higher degree of charge transfer is present within the system. Thus, the absorption profile of a photoinitiator can be controlled to some extent but not without altering the efficiency of radical formation. (see N. J. Turro, *Modern Molecular Photochemistry*, University Science Books: Sausalito, 1991).

In one preferred embodiment of the present invention, Z is designed so that it is attached via a heteroatom, —O— or —S—, to Pi, i.e. to the $Ar_2$ of formula (II). This particular functionality of Z confers greater hydrolytic stability at the same time as increasing the absorption in the 383-387 nm band region. An example of this effect is the comparison of the UV spectrum of chlorothioxanthone which has an absorption at 385 nm with a $E_1^1$ of 159 whereas its close relative which has a propoxy substituent on the aromatic ring, 1-chloro-4-propoxy thioxanthone has an absorption at 387 nm and an $E_1^1$ of 175. This enhanced extinction coefficient of absorption allows for faster curing. Accordingly, in one preferred embodiment of the invention Z is selected from —[O—($C_1$-$C_{12}$ alkylene)]$_m$-, —[S—($C_1$-$C_{12}$ alkylene)]$_m$-, —[O—($C_1$-$C_{12}$ alkylene)]$_m$-O—, —[S—($C_1$-$C_{12}$ alkylene)]$_m$-S—, —[O—($C_1$-$C_{12}$ alkylene)]$_m$-S—, and —[S—($C_1$-$C_{12}$ alkylene)]$_m$-O—. More preferably Z may be attached via a —O— moiety to Pi, hence in this case Z is —[O—($C_1$-$C_{12}$ alkylene)]$_n$-.

The particular advantage of linker —Z— being attached via a heteroatom, —O— or —S—, to Pi is that it confers greater hydrolytic stability at the same time as changing the absorption spectra, for an added —S— atom, an increased absorption in the 350-400 nm band region is seen. An example of this is effect is the comparison of the UV spectrum of 2-chlorothioxanthone which has an absorption maximum at 385 nm with a $E_1^1$ of 159 whereas its close relative with a propoxy substituent on the aromatic ring, 1-chloro-4-propoxy thioxanthone has an absorption maximum at 387 nm and an $E_1^1$ of 175. This enhanced extinction coefficient of absorption allows for faster curing.

A similar effect can be seen in comparing the UV spectra of 4-[(4-methylphenyl)sulfanyl]-benzophenone (Speedcure BMS) with 4-methylbenzophenone (Speedcure MBP). The absorption maximum of Speedcure BMS at 316 nm is extremely important in increasing the speed of cure of Speedcure BMS over Speedcure MBP. This band is non-existent in Speedcure MBP. FIG. 1 shows the UV spectra of BMS (0.001% w/v in methanol, 1 cm path length; bold black line) and MBP (0.001% w/v in methanol, 1 cm path length, thin dotted line).

More importantly, a similar effect is also observed for photoinitiator monomers of the invention. Comparing the UV spectra of 3-(4-benzoylphenoxyl)propane-1,2-diol with 1,3-diethyl 2-[(4-benzoylphenyl)methyl]propanedioate, it can be seen that these two photoinitiator monomers differ significantly in the extent of overlap between their absorption spectra and the emission spectrum of a standard mercury lamp. While the UV absorption of the former photoinitiator monomer extends to about 330 nm, the latter monomer only absorbs below 290 nm. This due to an increased extent of pi-electron conjugation in the former monomer which has an —O— group attached in the para-position of the benzophenone moiety. This means that the strong emission bands of a standard medium-pressure mercury lamp between 300-320 nm cannot be utilised to any significant extend by the latter monomer and its overall UV photo-crosslinking efficiency is therefore lower. FIG. 2: shows the UV absorption spectra of 3-(4-benzoylphenoxyl)propane-1,2-diol (Diol monomer prepared in Example 7; bold black line) and of 1,3-diethyl 2-[(4-benzoylphenyl)methyl]propanedioate (Diester monomer prepared in Example 8; dashed line). The UV spectral output lines of a standard medium-pressure mercury H lamp are shown as a grey bar chart.

The herein above described sub-formulas of photoinitiator monomers of general formula (I), applies for the second and third aspect of the invention in addition to the first aspect of the invention, mutatis mutandis. By way of example, the second aspect of the invention defined by formula (Ia) may be limited to the photoinitiator monomers defined by any of sub-formulas (II), (III), (IIIa), (IIIb), (IIIc), (IV), (IVa), or (IVb), where Z, $X_1$, $X_2$, $W_1$, $W_2$, $R^1$, and n is as defined for formula (Ia) or any further embodiments of these as described herein.

DEFINITIONS

The term "alkyl", as used herein, unless otherwise indicated, includes saturated monovalent hydrocarbon radicals having straight or branched moieties. Examples of alkyl moieties include, but are not limited to, methyl, ethyl, propyl, isopropyl, n-butyl, iso-butyl, sec-butyl, tert-butyl and neopentyl. Alkyl may preferably be $C_1$-$C_6$ alkyl, i.e. groups containing from 1 to 6 carbon atoms, and for some embodiments of the present invention more preferably $C_1$-$C_4$ alkyl.

The term "alkylene" as used herein specifies moieties derived from alkanes in which two H atoms have been removed to form a diradical species. The simplest alkylene is methylene, —$CH_2$—, and other alkylenes include ethylene —$CH_2$—$CH_2$—, propylene —$C_3H_6$— and butylene —$C_4H_8$—. The term "alkylene" includes branched and linear alkylenes, with linear alkylenes being most preferred. An alkylene which is a $C_1$-$C_{12}$ alkylene is one which contains between 1 and 12 carbon atoms. Preferred alkylenes contain between 1 and 6 carbon atoms (i.e. $C_1$-$C_6$ alkylenes).

The term "cycloalkyl" as used herein, unless otherwise indicated, includes non-aromatic saturated cyclic alkylene moieties, where alkylene is as defined above, or cyclic alkyl moieties, where alkyl is as defined above. The first applies where the cycloalkyl is used in a linker moiety being attached at two points to the remaining part of the photoinitiator monomers of formula (I). The skilled person will be able to identify in each case what applies. Examples of cycloalkyl include, but are not limited to, cyclopropyl, cyclobutyl, cyclopentyl, cyclohexyl, cycloheptyl, cyclooctyl. Cycloalkyl is preferably $C_3$-$C_8$ cycloalkyl, i.e. cycloalkyl groups containing from 3 to 8 carbon atoms, and more preferably $C_3$-$C_6$ cycloalkyl.

The term "alkenylene" as used herein specifies moieties derived from alkenes in which two H atoms have been removed to form a diradical species. Examples include ethenylene —CH=CH— and propenylene —$C_3H_4$— moieties. The term "alkenylene" includes branched, linear and cyclic alkenylene, with linear alkenylene being most preferred. Preferred alkenylenes contain between 2 and 6 carbon atoms (i.e. $C_2$-$C_6$ alkenylenes).

The term "aryl" as used herein defines an unsaturated cyclic system which contains a delocalised π-electron system about the ring. Aryl groups may comprise from 4-12 atoms, suitably from 6-8 atoms, most suitably 6 atoms. "Aryl" may preferably comprise carbocyclic rings, and may preferably be phenyl (—$C_6H_5$).

The term "aryl" is also used to include aromatic heterocycles—rings in which one or more atoms in the ring (e.g. 1-3 atoms) are N, S, P or O. Aromatic heterocycles include pyrrole, furan, thiophene, imidazole, imidazoline, pyrazole, pyrazoline, oxazole, oxazoline, isoxazole, isoxazoline, thiazole, thiazoline, isothiazole, isothiazoline (5-membered rings), pyridine, pyran, thiopyran (6-membered rings). The term "aryl" also includes fused ring systems.

When referring to a linker moiety (e.g. Z, $X_1$, $X_2$, Q, T), the term "aryl" is used to define moieties derived from arenes in which two H atoms have been removed to form a diradical species (i.e. arylene). Examples include 1,2-phenylene, 1,3-phenylene and 1,4-phenylene.

The term "heterocyclyl" as used herein means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. Preferred heterocyclyls contain about 5 to about 6 ring atoms. The prefix aza, oxa or thia before the heterocyclyl root name means that at least a nitrogen, oxygen or sulfur atom, respectively, is present as a ring atom. The heterocyclyl can be optionally substituted as described above. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

The term "acrylate monomer" is used to describe substances containing the functional group C=C—C(=O)—O—, which are able to polymerize via the alkene C=C moiety. The carbon atoms of the alkene may be substituted.

The term "leaving group", abbreviated "LG", is used to describe a reactive moiety bound to a carbon atom that can be displaced by another moiety in a substitution reaction thus forming a new carbon-carbon or carbon-heteroatom bond. Typically a leaving group LG is —F, —Cl, —Br, —I, —$OSO_2CH_3$, —$OSO_2$-(p-$C_6H_4$)—$CH_3$, —$OSO_2CF_3$.

The term "macromonomers" is used herein to describe a polymer or oligomer, that has two reactive groups, often at the ends, which enables it to act as a monomer in further polymerisation reactions becoming attached to the main backbone of the final polymer. Macromonomers may also be referred to as "pre-polymers". Non-limiting examples of suitable macromonomers or pre-polymers are polyalkylethers, polyesters, polydisulfides, polyamines, or polycarbonates having two free reactive groups, such as —OH groups, —$NH_2$ groups, —COOH groups, or —SH groups. Suitable macromers or pre-polymers to be used in polymeric photoinitiators of the present invention are described further in relation to monomer C.

When photoinitiator monomers of formula (I), comprise only two end groups $W_1$ and $W_2$ capable of taking part in a particular polymerisation reaction, the monomer of formula (I) will be incorporated in the polymer backbone with the photoinitiator as a pendant group via the linker Z. The linker is branched via the "branching carbon atom" and further branching of the polymer backbone is avoided. It is therefore to be avoided that other functional groups being capable of participating in the desired polymer reaction are present in the photoinitiator monomers of the present invention. This therefore also applies to any optional substituents being present on photoinitiator monomers of formula (I). Accordingly, in the following, when a part of a molecule, or a moiety, is described as "optionally substituted" or "is optionally substituted with one or more substituents" it refers to the optional possibility that one or more hydrogen atoms of a moiety, such as e.g. alkyl, alkylene, alkenyl, alkenylene, cycloalkyl, aryl, and heterocyclyl moieties (all referring to $C_1$-$C_{12}$ alkyl, $C_1$-$C_6$ alkyl, $C_3$-$C_8$ cycloalkyl etc. as appropriate in the context), may or may not be substituted by one or more substituents. For example 1 to 4 substituents, preferably 1 to 3 substituents, more preferably 1 or 2 substituents. Such one or more substituents, unless otherwise specifically stated, may independently be selected from the group consisting of —F, —Cl, —Br, —I, —CN, —$NO_2$, —$C_1$-$C_6$ alkyl, —$C_2$-$C_6$ alkenyl, —$C_3$-$C_6$ cycloalkyl, aryl, heterocyclyl, —O—($C_1$-$C_6$ alkyl), —O—$C_3$-$C_8$ cycloalkyl, —O-aryl, —C(O)—($R^3$), —C(O)-aryl, —N($C_1$-$C_6$ alkyl)$_2$, —N($C_1$-$C_6$ alkyl)($C_3$-$C_6$ cycloalkyl), —N($C_1$-$C_6$ alkyl)(aryl), —N(aryl)$_2$, —S(O)—($C_1$-$C_6$ alkyl), —S(O)-aryl, —$SO_2$—($C_1$-$C_6$ alkyl), —$SO_2$-aryl, —S—($C_1$-$C_6$ alkyl), and —S-aryl; wherein $R^3$ is H or $C_1$-$C_6$ alkyl.

In a preferred embodiment of the invention, the one or more optional substituents are independently selected from the group consisting of —F, —Cl, —Br, —I, —CN, —$NO_2$, —$C_1$-$C_6$ alkyl, aryl, —O—($C_1$-$C_6$ alkyl), —S—($C_1$-$C_6$ alkyl), —S(O)—($C_1$-$C_6$ alkyl), and —$SO_2$—($C_1$-$C_6$ alkyl).

Photoinitiator monomers of general formula (I) or (Ia) may contain chiral centers and therefore may exist in different enantiomeric or diastereomeric forms. This invention relates to all optical isomers and all stereoisomers of general formula (I), both as racemic mixtures and as individual enantiomers and diastereomers ((+)- and (−)-optically active forms) of such monomers and mixtures thereof. Individual isomers, if desired, can be obtained by known methods, such as optical resolution, optically selective reactions or chromatographic separation in the preparation steps or for the final products.

It will be apparent to one skilled in the art when a photoinitiator of the invention can exist as a salt or solvate form, especially as an acid addition salt or a base addition salt. When a photoinitiator can exist in a salt or solvate form, such forms are included within the scope of the invention. Examples of acid addition salts are fluorides, chlorides, bromides, iodides, sulfates, carbonates, phosphates, tetrafluoroborates, tetraarylborates (e.g. tetraphenylborates), hexafluorophosphates, alkyl carboxylates (e.g. acetates), aryl carboxylates (e.g. benzoates), alkyl sulfonates (e.g. mesylates) and aryl sulfonates (e.g. tosylates). Examples of base addition salts are lithium, sodium, potassium, calcium, ammonium and phosphonium salts.

The photoinitiator monomers of general formula (I) or (Ia) may contain a protecting group. The protective group is a group that protects the functional groups of the monomers prior to use in polymerization reactions, such protecting group may be covalently bound independently to $W_1$ and $W_2$ through a labile bond that can be broken before or during polymerisation. Photoinitiator monomers of formula (I) incorporating such protecting groups, are within the scope of the invention. The term "protecting group" or "protective group" as used herein, refers to e.g. silyl protecting group for —OH, —CH$_2$OH, —NH$_2$ or —NHR$^2$, which is selected from typical —Si(CH$_3$)$_3$, —Si(CH$_2$CH$_3$)$_3$, —Si(CH(CH$_3$)$_2$)$_3$, —Si(C$_6$H$_5$)$_3$ and —Si(CH$_3$)$_2$(C(CH$_3$)$_3$) groups. The term "protecting group" as used herein, also refers to e.g. thermally labile protecting group for —NCO or —NCS of $W_3$ or $W_4$ of monomer (B), which is selected from typical diethyl malonate (—CH(COOCH$_2$CH$_3$)$_2$ or 3,5-dimethylpyrazole (—N(—C(CH$_3$)=CH—C(CH$_3$)=N—)) as described in e.g. Protective Groups in Organic Synthesis edited by T. W. Greene et al. (John Wiley & Sons, 1991).

Linker Z and R$^1$

The portion of the photoinitiator monomer of general Formula (I) (Ia) indicated by Z represents a linker moiety. The linker Z therefore has two ends: at one end it is joined to the photoinitiator moiety, at the other end, it is joined to the "branching carbon atom". Simultaneously it serves to hold the photoinitiator moiety at a certain distance from the polymer backbone, when the photoinitiator monomer is incorporated into a polymeric photoinitiator.

The size of the linker Z is selected according to the desired properties of the photoinitiator. A short linker will provide close interaction between the polymer backbone and the photoinitiator moiety. On the other hand, a long linker will provide freer movement of the photoinitiator moiety in the polymerization process, which also provides advantages. A rigid structure may lower the possibility that radicals formed at one site propagate to polymer chains in the vicinity of the photoinitiator, whereas a "loose" structure could facilitate dispersion of radical functionalities over a wider area. Suitably, the linker has a molecular weight of less than 10000 Da, suitably less than 5000 Da, most suitably less than 1000 Da. The linker preferably comprises no more than 50 atoms, preferably no more than 30 atoms.

In formula (I) of the present invention, Z is a linker moiety selected from a single bond, $C_1$-$C_{12}$ alkylene, $C_2$-$C_{12}$ alkenylene, $C_3$-$C_8$ cycloalkyl, aryl, heterocyclyl, —($C_1$-$C_{12}$ alkylene)-aryl-, -aryl-($C_1$-$C_{12}$ alkylene)-, —($C_1$-$C_{12}$ alkylene)-heterocyclyl-, -heterocyclyl-($C_1$-$C_{12}$ alkylene)-, —[O—($C_1$-$C_{12}$ alkylene)]$_m$-, —[S—($C_1$-$C_{12}$ alkylene)]$_m$-, —[($C_1$-$C_{12}$ alkylene)-O]$_m$—, —[($C_1$-$C_{12}$ alkylene)]$_m$-O—, —[S—($C_1$-$C_{12}$ alkylene)]$_m$-S—, —[O—($C_1$-$C_{12}$ alkylene)]$_m$-S—, —[S—($C_1$-$C_{12}$ alkylene)]$_m$-O—; —C(=O)—, —[C(=O)—($C_1$-$C_{12}$ alkylene)]$_m$-, —[C(=O)-aryl]$_m$-, and —[C(=O)-heterocyclyl]$_m$-, wherein any alkylene, alkenylene, cycloalkyl, aryl, or heterocyclyl moiety independently is optionally substituted with one or more substituents selected from —F, —Cl, —Br, —I, —CN, —NO$_2$, —C$_1$-C$_6$ alkyl, aryl, —O—(C$_1$-C$_6$ alkyl), —S—(C$_1$-C$_6$ alkyl), —S(O)—(C$_1$-C$_6$ alkyl), and —SO$_2$—(C$_1$-C$_6$ alkyl).

By excluding amines from Z, the linker will not participate in the polymer reaction. i.e. if for example secondary amines where present these could form allophanate bonds, during a polyurethane polymerisation reaction leading to undesirable cross-linking, when a linear polymer chain is desirable.

Additionally, by excluding amines in the Z linker, photoinitiator monomers of formula (I) are useful in polymerization reactions where acids like sulphuric acid or arenesulfonic acids are used. If amines where present, they would neutralise the acids otherwise meant to be used in the polymerisation reaction.

In one embodiment of the invention, Z is selected from $C_1$-$C_{12}$ alkylene, $C_2$-$C_{12}$ alkenylene, $C_3$-$C_8$ cycloalkyl, aryl, heterocyclyl, —[O—($C_1$-$C_{12}$ alkylene)]$_m$-, —[S—($C_1$-$C_{12}$ alkylene)]$_m$-, —[($C_1$-$C_{12}$ alkylene)-O]$_m$—, —[($C_1$-$C_{12}$ alkylene)-S—]$_m$—, —[O—($C_1$-$C_{12}$ alkylene)]$_m$-O—, —[S—($C_1$-$C_{12}$ alkylene)]$_m$-S—, —C(=O)—, —[C(=O)—($C_1$-$C_{12}$ alkylene)]$_m$-, —[C(=O)-aryl]$_m$-, and —[C(=O)-heterocyclyl]$_m$-, where any of these moieties independently is optionally substituted with one or more substituents.

In another embodiment of the invention, Z is selected from $C_1$-$C_{12}$ alkylene, $C_2$-$C_{12}$ alkenylene, —[O—($C_1$-$C_{12}$ alkylene)]$_m$-, —[S—($C_1$-$C_{12}$ alkylene)]$_m$-, —[($C_1$-$C_{12}$ alkylene)-O]$_m$—, —[($C_1$-$C_{12}$ alkylene)-S—]$_m$—, —C(=O)—, and —[C(=O)—($C_1$-$C_{12}$ alkylene)]$_m$-, where any of these moieties independently is optionally substituted with one or more substituents.

In one preferred embodiment of the invention, Z is selected from $C_1$-$C_6$ alkylene, $C_2$-$C_6$ alkenylene, $C_3$-$C_8$ cycloalkyl, aryl, heterocyclyl, —($C_1$-$C_6$ alkylene)-aryl-, -aryl-($C_1$-$C_6$ alkylene)-, —($C_1$-$C_6$ alkylene)-heterocyclyl-, -heterocyclyl-($C_1$-$C_6$ alkylene)-, —[O—($C_1$-$C_6$ alkylene)]$_m$-, —[S—($C_1$-$C_6$ alkylene)]$_m$-, —[($C_1$-$C_6$ alkylene)-O]$_m$—, —[($C_1$-$C_6$ alkylene)-S—]$_m$—, —[O—($C_1$-$C_6$ alkylene)]$_m$-O—, —[S—($C_1$-$C_6$ alkylene)]$_m$-S—, —[O—($C_1$-$C_6$ alkylene)]$_m$-S—, and —[S—($C_1$-$C_6$ alkylene)]$_m$-O—], wherein any alkylene, alkenylene, cycloalkyl, aryl, or heterocyclyl moiety independently is optionally substituted with one or more substituents.

In another preferred embodiment of the invention, Z is selected from —[O—($C_1$-$C_{12}$ alkylene)]$_m$-, —[S—($C_1$-$C_{12}$ alkylene)]$_m$-, —[O—($C_1$-$C_{12}$ alkylene)]$_m$-O—, —[S—($C_1$-$C_{12}$ alkylene)]$_m$-S—, —[O—($C_1$-$C_{12}$ alkylene)]$_m$-O—, and —[S—($C_1$-$C_{12}$ alkylene)]$_m$-S—, where any alkylene moiety independently is optionally substituted with one or more substituents In a more preferred embodiment of the invention, Z is selected from —[O—($C_1$-$C_{12}$ alkylene)]$_m$- and —[S—($C_1$-$C_{12}$ alkylene)]$_m$-, where any alkylene moiety is independently optionally substituted with one or more substituents. As described herein above, by having a heteroatom, O or S, in the linker adjacent to the photoinitiator moiety, an enhanced photoinitiation is obtained. In a even more preferred embodiment of the invention, Z is —[O—($C_1$-$C_{12}$ alkylene)]$_m$-, where any alkylene moiety is independently optionally substituted with one or more substituents.

In the definitions of Z, m is an integer from 1-10; preferably m may be an integer from 1-5, such as e.g. 1, 2, 3, 4 or 5, more preferably from 1-2, and specifically 1.

In formula (I) there is a "branching carbon atom" connecting the linker Z with the two functional groups —$X_1$—$W_1$ and —$X_2$—$W_2$. In addition the branching carbon atom has attached a $R^1$ moiety, which is selected from H, $C_1$-$C_{12}$ alkyl, $C_2$-$C_{12}$ alkenyl, $C_3$-$C_8$ cycloalkyl, aryl, heterocyclyl, —[O—($C_1$-$C_{12}$ alkylene)]$_m$-H, —[S—($C_1$-$C_{12}$ alkylene)]$_m$-H, —C(=O)—H, —[C(=O)—($C_1$-$C_{12}$ alkylene)]$_m$-H, —[C(=O)-aryl]$_m$-H, and —[C(=O)-heterocyclyl]$_m$-H, wherein any alkyl, alkenyl, alkylene, cycloalkyl, aryl, or heterocyclyl moiety independently is optionally substituted with one or more substituents, as defined herein.

In a preferred embodiment of the invention, $R^1$ is selected from H, $C_1$-$C_{12}$ alkyl, $C_2$-$C_{12}$ alkenyl, —[O—($C_1$-$C_{12}$ alkylene)]$_m$-H, —[S—($C_1$-$C_{12}$ alkylene)]$_m$-H, —C(=O)—H, and —[C(=O)—($C_1$-$C_{12}$ alkylene)]$_m$-H, where any alkyl, alkylene, or alkenyl moiety independently is optionally substituted with one or more substituents.

In another preferred embodiment of the invention, $R^1$ is selected from H, $C_1$-$C_6$ alkyl, $C_2$-$C_6$ alkenyl, —[O—($C_1$-$C_6$ alkylene)]$_m$-H, —[S—($C_1$-$C_6$ alkylene)]$_m$-H, —C(=O)—H, and —[C(=O)—($C_1$-$C_6$ alkylene)]$_m$-H, where any alkyl, alkylene, or alkenyl moiety independently is optionally substituted with one or more substituents.

In a specific embodiment of the invention, $R^1$ is methyl, ethyl, n-propyl, sec-propyl, n-butyl, sec-butyl, n-pentyl, sec-pentyl, n-hexyl, benzyl, 2-methoxyethyl or 2-ethoxyethyl.

In formula (I) n is an integer of 1 or 2, with the proviso that when n is 2, $R^1$ is absent. In other words, when n of formula (I) is 2, then two Pi-Z— moieties are attached to the branching carbon atom, and then $R^1$ is absent. In one embodiment of the invention n is 1. In another embodiment of the invention n is 2.

$X_1$ and $X_2$

The groups $X_1$ and $X_2$ serve to connect the branching carbon atom with the end groups $W_1$ and $W_2$. The size and form of these groups can be varied to adjust the properties of the photoinitiator polymer.

In formula (I) $X_1$ and $X_2$ are each independently selected from a single bond, $C_1$-$C_{12}$ alkylene, $C_2$-$C_{12}$ alkenylene, $C_3$-$C_8$ cycloalkyl, aryl, heterocyclyl, —[O—($C_1$-$C_{12}$ alkylene)]$_p$, and —[S—($C_1$-$C_{12}$ alkylene)]$_p$, wherein p is an integer from 1-10, and wherein any alkylene, alkenylene, cycloalkyl, aryl, or heterocyclyl moiety independently is substituted with one or more substituents; and wherein $X_1$, $X_2$, $R^1$ or Z each independently may be linked to one another to form one or more ring structures.

Additionally, $X_1$, $X_2$, $R^1$ or Z each independently may be linked to one another to form one or more ring structures. In one embodiment of the invention, $X_1$, $X_2$, $R^1$ or Z are not linked to one another to form one or more ring structures.

$X_1$ and $X_2$ may be the same or different, and are preferably the same, for ease of chemical synthesis.

In the preferred photoinitiator monomers of formula (Ia) $X_1$ and $X_2$ are the same and otherwise selected from the moieties described here above or from any of the embodiments described herein below.

In one embodiment of the invention, $X_1$ and $X_2$ each independently are selected from $C_1$-$C_{12}$ alkylene, $C_2$-$C_{12}$ alkenylene, —[O—($C_1$-$C_{12}$ alkylene)]$_m$, and —[S—($C_1$-$C_{12}$ alkylene)]$_m$, where any alkylene or alkenylene moiety independently is optionally substituted with one or more substituents.

In a preferred embodiment of the invention, $X_1$ and $X_2$ each independently are selected from $C_1$-$C_{12}$ alkylene, —[O—($C_1$-$C_{12}$ alkylene)]$_m$, and —[S—($C_1$-$C_{12}$ alkylene)]$_m$, where any alkylene moiety is independently optionally substituted with one or more substituents.

In a more preferred embodiment of the invention. $X_1$ and $X_2$ each independently are selected from $C_1$-$C_6$ alkylene, —[O—($C_1$-$C_6$ alkylene)]$_m$, and —[S—($C_1$-$C_6$ alkylene)]$_m$, where any alkylene moiety independently is optionally substituted with one or more substituents. Specifically $X_1$ and $X_2$ may each independently be selected from methylene, ethylene, propylene, isopropylene, butylene, isobutylene, sec-butylene, pentyl, isopentyl, and sec-pentylene, preferably ethylene and propylene.

In the above definitions $X_1$ and $X_2$ m is an integer from 1-10; preferably m may be an integer from 1-5, such as e.g. 1, 2, 3, 4 or 5, more preferably from 1-2, and specifically 1.

End Groups, $W_1$, $W_2$

The end groups $W_1$ and $W_2$ in Formula (I) allow the photoinitiator to be incorporated into a growing polymer chain, such as e.g. a polyester chain. $W_1$ and $W_2$ are therefore selected from those functional groups which are reactive in polymerization reactions and which then are able to bond to other monomers. When the intended polymer is e.g. a polyester the monomers may therefore have $W_1$ and $W_2$ groups independently selected from e.g. —OH, —$CH_2OH$, —COOH, or —$COOR^2$. These are able to bond to other polyester monomers to thus form the polymer.

In formula (I) $W_1$ and $W_2$ are each independently selected from —OH (forming a secondary alcohol), —$CH_2OH$, —COOH, —$COOR^2$, —COO-aryl, —SH, —$CH_2SH$, —$NH_2$, —$NHR^2$, —NCO, —NCS, —C(=O)—Cl, and —O—C(=O)—Cl, wherein $R^2$ is selected from optionally substituted $C_1$-$C_{12}$ alkyl and aryl. In a specific embodiment of formula (I), $W_1$ and $W_2$ are each independently selected from —OH, —$CH_2OH$, —COOH, —$COOR^2$, —COO-aryl, —SH, —$CH_2SH$, —NCO, —NCS, —C(=O)—Cl, and —O—C(=O)—Cl; by having no amine groups as the functional groups polymerisation reactions may be performed in presence of acid.

In one preferred embodiment of formula (I), $W_1$ and $W_2$ each independently is selected from —$CH_2OH$, —COOH, —$COOR^2$ and —$CH_2SH$, these functional groups are especially valuable in preparation of polyesters and polyethers.

In the preferred photoinitiator monomers of formula (Ia) $W_1$ and $W_2$ are the same and are selected from —OH, —$CH_2OH$, —COOH, —$COOR^2$, —COO-aryl, —$NH_2$, —$NHR^2$, —NCO, —NCS, —C(=O)—Cl, and —O—C(=O)—Cl, wherein $R^2$ is selected from optionally substituted $C_1$-$C_{12}$ alkyl and aryl. In one preferred embodiment of formula (Ia), $W_1$ and $W_2$ are the same and are selected from —$CH_2OH$, —COOH, and —$COOR^2$, these functional groups are especially valuable in preparation of polyesters and polyethers. Further details and preferred embodiments of $W_1$ and $W_2$ are described below.

When preparing polyester or polyethers the reaction conditions used industrial scale processing typically rely on high temperature and/or acids. The photoinitiator monomers of the present invention are especially suited to withstand these conditions. Neither the linker Z or $W_1$ and $W_2$ contain hydrolytically unstable bonds.

In the definitions of $W_1$ and $W_2$, —$NH_2$ denotes a primary amines, and —$NHR^2$, where $R^2$ is selected from optionally substituted $C_1$-$C_{12}$ alkyl, denotes a secondary amine.

In the definitions of $W_1$ and $W_2$, —$CH_2OH$ denotes primary alcohol attached onto $X_1$ or $X_2$. For instance, if $W_1$ is —$CH_2OH$ and $X_1$ is methylene then the moiety —$X_1$—$W_1$ is —$CH_2CH_2OH$; and if $W_1$ is —$CH_2OH$ and $X_1$ is a single bond then the moiety —$X_1$—$W_1$ is —$CH_2OH$. In the same manner in the definitions of $W_1$ and $W_2$, —OH is to be understood as a forming a secondary alcohol with $X_1$ or $X_2$. For instance, if $W_1$ is —OH and $X_1$ is a branched ethane, i.e.

ethane-1,1-diyl —CH(CH$_3$)—, then the moiety —X$_1$—W$_1$ may be —CH(OH)CH$_3$; and if W$_1$ is —OH and X$_1$ is a single bond then the moiety —X$_1$—W$_1$ is —OH attached directly to the carbon branching atom. Due to the lower reactivity of tertiary alcohols these are undesirable as W$_1$ and W$_2$ groups.

R$^2$ may preferably be optionally substituted C$_1$-C$_6$ alkyl, such as e.g. methyl, ethyl, propyl, butyl, pentyl or hexyl; more preferably R$^2$ may be C$_1$-C$_4$ alkyl, such as e.g. methyl, ethyl, or propyl.

In another preferred embodiment of the invention, W$_1$ and W$_2$ are independently —OH or —CH$_2$OH. When W$_1$ and W$_2$ are a two alcohol groups, it is preferred that these are attached at X$_1$ and X$_2$ so as both form a primary alcohol (i.e. —CH$_2$OH), or both form a secondary alcohol (i.e. —OH in the definition of W$_1$ and W$_2$). Hereby allowing for symmetric growth of the polymer chain. In the same manner, it is preferred that when W$_1$ and W$_2$ are two amine groups, i.e. —NH$_2$ or —NHR$^2$, they are either two primary amine groups or two secondary amine groups. Primary alcohols (—CH$_2$OH) are additionally preferred due to their higher reaction rates in reactions with —COOH or —COOR$^2$ moieties (i.e. esterification or transesterification reactions). Moreover, primary alcohol are preferred over e.g. secondary and tertiary alcohols since they are less prone to side reactions such as dehydration in reactions catalysed by strong acids.

Furthermore, in one embodiment of the invention, in formula (I), one of W$_1$ and W$_2$ is —CH$_2$OH and the other is —COOH. This is for instance the case where a photoinitiator of formula (I) is to be reacted in an esterification reaction with another monomer having one hydroxy (—OH, or —CH$_2$OH) and one —COOH reactive group such as lactic acid.

In a preferred embodiment of the invention, W$_1$ and W$_2$ are the same.

In a specific and preferred embodiment of the invention, X$_1$ and X$_2$ both are optionally substituted C$_1$-C$_{12}$ alkylene, being same or different, and W$_1$ and W$_2$ both are —CH$_2$OH.

In that only two end groups W$_1$ and W$_2$ are present, the photoinitiator does not promote branching of a polymeric photoinitiator. Instead, the photoinitiator monomers of Formula (I) are incorporated partly into the polymer chain, while the photoinitiator moieties are pendant from the chain.

Specific Photoinitiator Monomers

Suitable photoinitiator monomers of formula (I) include:
4-[2,2-bis(hydroxymethyl)butan-1-yloxy]benzophenone;
4-[2,2-bis(hydroxymethyl)butan-1-yloxymethyl]benzophenone;
4-[5,5-bis(hydroxymethyl)-1,3-dioxan-2-yl]benzophenone;
1-benzoyl-3-[2,2-bis(hydroxymethyl)butan-1-yloxymethyl]-2,4,6-trimethylbenzene;
4-[1,3-dihydroxypropan-2-yloxy]benzophenone;
4-[2,2-bis(hydroxymethyl)butan-1-yloxyethoxy]benzophenone;
2,2-bis(4-benzoylphenoxymethyl)propane-1,3-diol;
2,2-bis(1-chloro-9-oxo-9H-thioxanthen-4-yloxymethyl)propane-1,3-diol;
2,2-bis(4-benzoylphenoxymethyl)propane-1,3-diamine;
2,2-bis(4-benzoylphenoxymethyl)propane-1,3-dithiol;
[4-(phenylcarbonyl)benzyl]propanedioic acid;
[4-(phenylcarbonyl)benzyl]propanedioyl dichloride;
dimethyl [4-(phenylcarbonyl)benzyl]propanedioate;
4-[3-hydroxy-2-(hydroxymethyl)propan-1-yloxy]benzophenone;
4-[4-hydroxy-3-(hydroxymethyl)butyl]benzophenone;
4-[3-hydroxy-2-(hydroxymethyl)-2-methylpropan-1-yloxy]benzophenone;
4-[4-hydroxy-3-(hydroxymethyl)-3-methylbutyl]benzophenone; or
dimethyl 2-[4-(phenylcarbonyl)benzyl]butanedioate.

Suitable photoinitiator monomers of formula (I) and formula (Ia) include:
4-[2,2-bis(hydroxymethyl)butan-1-yloxy]benzophenone;
4-[2,2-bis(hydroxymethyl)butan-1-yloxymethyl]benzophenone;
4-[5,5-bis(hydroxymethyl)-1,3-dioxan-2-yl]benzophenone;
1-benzoyl-3-[2,2-bis(hydroxymethyl)butan-1-yloxymethyl]-2,4,6-trimethylbenzene;
4-[1,3-dihydroxypropan-2-yloxy]benzophenone;
4-[2,2-bis(hydroxymethyl)butan-1-yloxyethoxy]benzophenone;
2,2-bis(4-benzoylphenoxymethyl)propane-1,3-diol;
2,2-bis(1-chloro-9-oxo-9H-thioxanthen-4-yloxymethyl)propane-1,3-diol;
2,2-bis(4-benzoylphenoxymethyl)propane-1,3-diamine;
[4-(phenylcarbonyl)benzyl]propanedioic acid;
[4-(phenylcarbonyl)benzyl]propanedioyl dichloride;
dimethyl [4-(phenylcarbonyl)benzyl]propanedioate;
4-[3-hydroxy-2-(hydroxymethyl)propan-1-yloxy]benzophenone;
4-[4-hydroxy-3-(hydroxymethyl)butyl]benzophenone;
4-[3-hydroxy-2-(hydroxymethyl)-2-methylpropan-1-yloxy]benzophenone;
4-[4-hydroxy-3-(hydroxymethyl)-3-methylbutyl]benzophenone; or
dimethyl 2-[4-(phenylcarbonyl)benzyl]butanedioate.

Preferred photoinitiator monomers of formula (I) include:
4-[2,2-bis(hydroxymethyl)butan-1-yloxy]benzophenone;
4-[1,3-dihydroxypropan-2-yloxy]benzophenone;
2,2-bis(4-benzoylphenoxymethyl)propane-1,3-diol;
2,2-bis(1-chloro-9-oxo-9H-thioxanthen-4-yloxymethyl)propane-1,3-diol;
[4-(phenylcarbonyl)benzyl]propanedioic acid;
[4-(phenylcarbonyl)benzyl]propanedioyl dichloride;
dimethyl [4-(phenylcarbonyl)benzyl]propanedioate;
4-[3-hydroxy-2-(hydroxymethyl)propan-1-yloxy]benzophenone;
dimethyl 2-[4-(phenylcarbonyl)benzyl]butanedioate;
3-(4-benzoylphenoxyl)propane-1,2-diol;
diethyl [4-(phenylcarbonyl)benzyl]propanedioate;
diethyl 2-[3-(4-benzoylphenoxyl)propyl]propanedioate; or
2,2-bis(4-benzoylphenoxymethyl)propane-1,3-diol.

In one embodiment preferred photoinitiator monomers of formula (I) include:
4-[2,2-bis(hydroxymethyl)butan-1-yloxy]benzophenone;
4-[1,3-dihydroxypropan-2-yloxy]benzophenone;
2,2-bis(4-benzoylphenoxymethyl)propane-1,3-diol;
2,2-bis(1-choro-9-oxo-9H-thioxanthen-4-yloxymethyl)propane-1,3-diol;
[4-(phenylcarbonyl)benzyl]propanedioic acid;
[4-(phenylcarbonyl)benzyl]propanedioyl dichloride;
dimethyl [4-(phenylcarbonyl)benzyl]propanedioate;
4-[3-hydroxy-2-(hydroxymethyl)propan-1-yloxy]benzophenone; or
dimethyl 2-[4-(phenylcarbonyl)benzyl]butanedioate.

In one embodiment preferred photoinitiator monomers of formula (I) or subformula (Ia) include:
4-[2,2-bis(hydroxymethyl)butan-1-yloxy]benzophenone;
4-[1,3-dihydroxypropan-2-yloxy]benzophenone;
2,2-bis(4-benzoylphenoxymethyl)propane-1,3-diol;
2,2-bis(1-choro-9-oxo-9H-thioxanthen-4-yloxymethyl)propane-1,3-diol;
[4-(phenylcarbonyl)benzyl]propanedioic acid;
[4-(phenylcarbonyl)benzyl]propanedioyl dichloride;
dimethyl [4-(phenylcarbonyl)benzyl]propanedioate;

4-[3-hydroxy-2-(hydroxymethyl)propan-1-yloxy]benzophenone;
diethyl [4-(phenylcarbonyl)benzyl]propanedioate;
diethyl 2-[3-(4-benzoylphenoxyl)propyl]propanedioate; or
2,2-bis(4-benzoylphenoxymethyl)propane-1,3-diol.

Polymeric Photoinitiators

The first aspect of the invention relates to a polymeric photoinitiators, being a co-polymer of at least one monomer (A) with at least one monomer (B), wherein:

monomer (A) is a photoinitiator monomer (A) of the general formula (I):

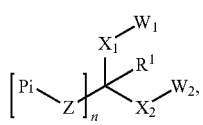

(I)

wherein general formula (I), or subformulas (Ia), (II), (III), (IIIa), (IIIb), (IIIc), (IV), (IVa), or (IVb), including preferred options of these, is as defined herein above or below;

monomer (B) comprises at least two functional groups $W_3$ and $W_4$, said $W_3$ and $W_4$ being independently selected from —F, —Cl, —Br, —I, —OSO$_2$R$^4$, —OSO$_2$—Ar$^3$, —OH (i.e. forming a secondary alcohol), —CH$_2$OH, —COOH, —COOR$^4$, —COO-aryl, —SH, —CH$_2$SH, —NH$_2$, —NHR$^4$, —NCO, —NCS, —C(=O)—Cl, and —O—C(=O)—Cl, wherein R$^4$ is selected from optionally substituted C$_1$-C$_{12}$ alkyl; wherein R$^4$ is selected from optionally substituted C$_1$-C$_{12}$ alkyl and Ar$^a$ is selected from optionally substituted aryl; or $W_3$ and $W_4$ are linked to each other forming a cyclic lactone or thiolactone;

wherein $W_1$, $W_2$, $W_3$ and $W_4$ are selected such that—in the co-polymerization of monomers (A) and (B)—$W_1$ reacts with $W_3$ to form a urethane, urea, amide, thiourethane, thiourea, dithiourethane, ester, ether, carbonate, phosphonite, phosphonate, phosphate, allophanate or biuret moiety, and $W_2$ reacts with $W_4$ to form a urethane, urea, amide, thiourethane, thiourea, dithiourethane, ester, ether, carbonate, phosphonite, phosphonate, phosphate, allophanate or biuret moiety.

Accordingly, the definitions of Pi, Z, n, $X_1$, $X_2$, $W_1$, $W_2$, $R^1$, $R^2$, and $R^3$, as described herein in connection with the photoinitiator monomers of formula (I), applies for the first aspect of the invention as well. Polymerization of the polymeric photoinitiator is achieved by step-growth co-polymerization of monomers (A) and (B). The physical, chemical and photocatalytic properties of the polymeric photoinitiator can be varied depending on the nature and relative amounts of the monomers (A) and (B).

In a preferred embodiment of the first aspect of the invention, the photoinitiator monomers are of formula (Ia) as described for the second aspect of the invention.

In the above definition of $W_3$ and $W_4$ further details about the moieties —OH (forming a secondary alcohol), —CH$_2$OH, —NH$_2$, and —NHR$^4$ may be found in relation to $W_1$ and $W_2$, mutatis mutandis. The definitions and details are analogous.

$R^4$ may preferably be optionally substituted C$_1$-C$_6$ alkyl, such as e.g. methyl, ethyl, propyl, butyl, pentyl or hexyl.

Monomer (B) may have a structure of formula (V):

$$W_3\text{-}Q\text{-}W_4 \qquad (V)$$

wherein $W_3$ and $W_4$ are defined above and wherein Q is selected from the group consisting of optionally substituted C$_1$-C$_{12}$ alkylene, optionally substituted C$_2$-C$_{12}$ alkenylene, optionally substituted C$_3$-C$_8$ cycloalkyl, optionally substituted C$_3$-C$_{12}$ heterocyclyl, optionally substituted aryl, optionally substituted biaryl, —[O—(C$_1$-C$_{12}$ alkylene)]$_q$-, —[S—(C$_1$-C$_{12}$ alkylene)]$_q$-, where q is an integer from 1-1000, and combinations thereof. Q could also comprise one of the photoinitiator moieties (Pi) set out above.

As an example, Q may for instance be a dicyclohexylmethylene and would then, in the above definition, correspond to a (C$_3$-C$_8$ cycloalkyl)-(C$_1$-C$_{12}$ alkylene)-(C$_3$-C$_8$ cycloalkyl) moiety.

Q may be selected from the group consisting of optionally substituted C$_1$-C$_{12}$ alkylene, optionally substituted C$_2$-C$_{12}$ alkenylene, optionally substituted C$_3$-C$_8$ cycloalkyl, optionally substituted C$_3$-C$_{12}$ heterocyclyl, optionally substituted aryl, optionally substituted biaryl and combinations thereof.

Q may be selected from the group consisting of optionally substituted C$_1$-C$_{12}$ alkylene, optionally substituted C$_1$-C$_{12}$ alkenylene, optionally substituted C$_3$-C$_8$ cycloalkyl, optionally substituted C$_3$-C$_{12}$ heterocyclyl, optionally substituted aryl and optionally substituted biaryl. Q may be selected from the group consisting of optionally substituted aryl and optionally substituted biaryl.

Preferably $W_3$ and $W_4$ may each independently selected from —F, —Cl, —Br, —I, —OSO$_2$R$^4$, —OSO$_2$—Ar$^3$, —OH, —CH$_2$OH, —COOH, —COOR$^4$, —SH, —NCO, —NCS, and —C(=O)—Cl. In one preferred embodiment of the invention, one of $W_3$ and $W_4$ is —CH$_2$OH and the other is —COOH. In an alternatively preferred embodiment of the invention, $W_3$ and $W_4$ are the same functional groups.

Alternatively, $W_3$ and $W_4$ may each independently selected from —F, —Cl, —Br, —I, —OSO$_2$R$^4$, —OSO$_2$—Ar$^3$, —OH, —CH$_2$OH, —COOH, —COOR$^4$, —NCO, —NCS, and —C(=O)—Cl.

Suitable compounds falling within the above definitions of monomer (B) includes, but are not limited to, aliphatic hydroxyacids, including glycolic acid, lactic acid, 4-hydroxybutyric acid and 6-hydroxyhexanoic acid, and diacids, including malonic, succinic, glutaric, adipic, phthalic and terephthalic acid.

In one embodiment of the invention, $W_3$ and $W_4$ are linked to each other forming a cyclic lactone or thiolactone. These forms of cyclic monomer (B) are also included within the scope of the invention. Suitable examples of such lactones include beta-propiolactone, gamma-butyrolactone, delta-valerolactone and epsilon-caprolactone.

In one embodiment of the invention, $W_3$ and $W_4$ are each independently selected from isocyanate and thioisocyanate groups (i.e. —NCO and —NCS). This embodiment is especially relevant in the preparation of polyurethane, polythiourethane, polydithiourethane, and polyurea polymers.

In particular embodiments, monomer (B) is a polyisocyanate, preferably a diisocyanate. Suitable polyisocyanates have an average of about two or more isocyanate groups, preferably an average of about two to about four isocyanate groups and include aliphatic, cycloaliphatic, aralkyl and aromatic polyisocyanates, used alone or in mixtures of two or more. Of these are diisocyanates are preferred, this is for example the case where the polymeric photoinitiator is a polyurethane.

Specific examples of suitable aliphatic polyisocyanates include alpha, omega-alkylene diisocyanates having from 5 to 20 carbon atoms, such as hexamethylene-1,6-diisocyanate, 1,12-dodecane diisocyanate, 2,2,4-trimethyl-hexamethylene diisocyanate, 2,4,4-trimethyl-hexamethylene diisocyanate, 2-methyl-1,5-pentamethylene diisocyanate and the like. Polyisocyanates having fewer than 5 carbon atoms can be used but are less preferred because of their high volatility and toxicity. Preferred aliphatic polyisocyanates include hexamethylene-1,6-diisocyanate, 2,2,4-trimethyl-hexamethylene-diisocyanate and 2,4,4-trimethyl-hexamethylene diisocyanate.

Specific examples of suitable cycloaliphatic polyisocyanates include dicyclohexylmethane diisocyanate, isophorone diisocyanate, 1,4-cyclohexane diisocyanate, 1,3-bis-(isocyanatomethyl)cyclohexane and the like. Preferred cycloaliphatic polyisocyanates include dicyclohexylmethane diisocyanate and isophorone diisocyanate. Specific examples of suitable aralkyl polyisocyanates include m-tetramethyl xylylene diisocyanate, p-tetramethyl xylylene diisocyanate, 1,4-xylylene diisocyanate, 1,3-xylylene diisocyanate, and the like. A preferred araliphatic polyisocyanate is tetramethyl xylylene diisocyanate. Examples of suitable aromatic polyisocyanates include 4,4'-diphenylmethylene diisocyanate, toluene diisocyanate, their isomers, naphthalene diisocyanate and the like. A preferred aromatic polyisocyanate is toluene diisocyanate.

Monomer (B) may be selected from the group consisting of: 1,4-phenylene diisocyanate (PPDI), toluene diisocyanate (TDI) as both its 2,4 and 2,6 isomers, methylene diphenyl diisocyanate (MDI) as both its 4,4' and 2,4' isomers, 1,5-naphthalene diisocyanate (NDI), 3,3'-bitolylene-4,4'-diisocyanate (TODI), 1,3-xylylenediisocyanate (XDI), tetramethyl-m-xylidene diisocyanate (TMXDI), 1,6-hexamethylene diisocyanate (HDI), isophorone diisocyanate (IPDI), bis(4-isocyanatocyclohexyl)methane (HMDI), 2,2,5-trimethylhexane diisocyanate (TMHDI), 1,4-cyclohexane diisocyanate (CHDI) and 1,3-bis(isocyanato-methyl)cyclohexane (HXDI).

Importantly, $W_1$, $W_2$, $W_3$ and $W_4$ are selected such that—in the co-polymerization of monomers (A) and (B)—$W_1$ reacts with $W_3$ to form a urethane, urea, amide, thiourethane, thiourea, dithiourethane, ester, ether, carbonate, phosphonite, phosphonate, phosphate, allophanate or biuret moiety, and $W_2$ reacts with $W_4$ to form a urethane, urea, amide, thiourethane, thiourea, dithiourethane, ester, ether, carbonate, phosphonite, phosphonate, phosphate, allophanate or biuret moiety. In one preferred embodiment of the second aspect of the invention $W_1$ reacts with $W_3$ to form a urethane, thiourethane, urea, thiourea, ester, amide or ether moiety, and $W_2$ reacts with $W_4$ to form urethane, thiourethane, urea, thiourea, ester, amide or ether moiety. In another preferred embodiment of the second aspect of the invention, $W_1$ and $W_2$ reacts with $W_3$ and $W_4$ to form an ether or ester moiety.

Given a particular $W_1$ or $W_2$, the skilled person will be able to select the appropriate $W_3$ or $W_4$ to provide the polymeric photoinitiators of the invention.

In a preferred embodiment of the invention, the polymeric photoinitiator is a polyester or a polyether photoinitiator. In this specific embodiment both $W_1$ and $W_2$ are alcohol functional groups, and $W_3$ and $W_4$—COOH, —COOR$^4$, or —COO-aryl.

In an alternatively preferred embodiment of the invention, the polymeric photoinitiator is a polyurethane photoinitiator. In this case, $W_1$ and $W_2$ are selected to be alcohol functional groups, and $W_3$ and $W_4$ are selected as isocyanate groups to provide urethane moieties when monomer (A) reacts with monomer (B). A polyurethane photoinitiator will thus be formed. The reverse arrangement ($W_1$ and $W_2$ are isocyanate functional groups, while $W_3$ and $W_4$ are alcohol groups) will also provide a polyurethane. In this case in a preferred embodiment of monomer (A) $W_1$ and $W_2$ are selected so as both the alcohol functional groups are either primary (—CH$_2$OH) or secondary alcohol (i.e. —OH in the definition of $W_1$ and $W_2$) groups.

Similarly, if $W_1$ and $W_2$ are thiol functional groups, selection of $W_3$ and $W_4$ as isocyanate groups will provide thiourethane moieties when monomer (A) reacts with monomer (B). The reverse arrangement is also possible.

To form urea moieties from $W_1$-$W_4$, it is possible to select $W_1$ and $W_2$ as amine functional groups and $W_3$ and $W_4$ as isocyanate functional groups. Polyurea photoinitiators will thus be formed. The reverse situation is also possible ($W_1$ and $W_2$ are isocyanate functional groups, while $W_3$ and $W_4$ are amine functional groups). In this case in a preferred embodiment of monomer (A), $W_1$ and $W_2$ are selected so as both the amine functional groups are either primary or secondary amine groups.

Suitably, $W_3$ and $W_4$ are the same functional groups, as are $W_1$ and $W_2$. However, it is possible that $W_1$ and $W_2$ are different, as long as $W_3$ and $W_4$ are selected such that a polymer may be formed.

More than one type of monomer (A) and more than one type of monomer (B) may be used in the polymeric photoinitiators of the invention. As well as the regular structure . . . ABABABAB . . . , the polymeric photoinitiators may therefore also have a structure which incorporates variations of monomers A and B, e.g. . . . A'BABA'B'A'B'A'BABA'B' . . . .

One or more additional monomers (C) may also be present in the polymeric photoinitiators of the invention. Each of said one or more additional monomers (C) comprises at least two functional groups $W_5$ and $W_6$, said $W_5$ and $W_6$ being independently selected from —F, —Cl, —Br, —I, —OSO$_2$R$^5$, —OSO$_2$—Ar$^4$, —OH (forming a secondary alcohol), —CH$_2$OH, —COOH, —COOR$^5$, —COO-aryl, —SH, —CH$_2$SH, —NH$_2$, —NHR$^5$, —NCO, —NCS, —C(=O)—Cl, and —O—C(=O)—Cl, wherein R$^5$ is selected from optionally substituted $C_1$-$C_{12}$ alkyl and Ar$^4$ is selected from optionally substituted aryl;

wherein $W_5$ and $W_6$ are selected such that—in the co-polymerization of monomers (A), (B) and (C)—$W_5$ reacts with $W_1$ or $W_3$ to form a urethane, thiourethane, urea, thiourea, ester, ether, amide, carbonate, allophanate or biuret moiety, and $W_6$ reacts with $W_2$ or $W_4$ to form a urethane, thiourethane, urea, thiourea, ester, ether, amide, carbonate, allophanate or biuret moiety. Suitably, $W_5$ reacts with $W_1$ or $W_3$ to form a urethane, thiourethane, urea, thiourea, ester, amide or ether moiety, and $W_6$ reacts with $W_2$ or $W_4$ to form a urethane, thiourethane, urea, thiourea, ester, amide or ether moiety.

In a preferred embodiment of the invention $W_5$ and $W_6$ are independently selected from —F, —Cl, —Br, —I, —OH (i.e. forming a secondary alcohol), —CH$_2$OH, —COOH, —COOR⁵, —COO-aryl, —NH₂, —NHR⁵, —NCO, —NCS, —C(=O)—Cl, and —O—C(=O)—Cl, wherein R⁵ is $C_1$-$C_6$ alkyl.

In a preferred embodiment of the second aspect of the invention, $W_1$ reacts with $W_3$ to form an ether or ester moiety. Preferred options of $R^5$ are as described herein for $R^4$, mutatis mutandis.

In one embodiment of the invention, where one or more additional monomers (C) are present, these may be a macromonomer selected from polyether, polyester, polycarbonate, polyamine, and polydisulfide having the herein above or below described two functional groups $W_5$ and $W_6$. Suitably, polyether macromonomer (C) may be of a molecular weight between 200 and 20,000, more suitably between 200 and 15,000, even more suitably between 200 and 10,000, yet even more suitable between 1000 and 8,000, such as e.g. a polyethylene glycol (PEG), polypropylene glycol (PPG), random or block poly(ethylene glycol)-poly(propylene glycol) copolymer or poly(tetramethylene glycol) (PTMG). Suitably, polyester macromonomer (C) may be of a molecular weight between 200 and 10,000, such as e.g. 200 and 8,000, these being e.g. diol end-capped poly(1,4-butanediol adipate), poly(ethanediol 1,4-butanediol adipate), poly(caprolacton) diol or poly(ethylene terephthalate) diol. Suitably, polycarbonate macromonomer (C) may be of a molecular weight between 500 and 10,000, such as e.g. poly(hexamethylene carbonate) diol. Suitably, polyamine macromonomer (C) may be of a molecular weight between 500 and 10,000, such as e.g. a hydroxyl end-functionalised poly(2-methyl-2-oxazoline). Suitably, polydisulfide macromonomer (C) may be of a molecular weight between 1000 and 10,000, such as e.g. Thiokol® LP thiol end-capped polymer (e.g. Thiokol® LP-32 or Thiokol® LP-33).

Depending on the choice of $W_5$ and $W_6$, and the relative amounts of monomers (A), (B) and (C), the polymeric photoinitiator may have a variety of repeating structures such as e.g.:

...ABABABABCBABABCBAB... (if $W_5$ and $W_6$ react with $W_3$ and $W_4$)

...ABABACACABABABACAC... (if $W_5$ and $W_6$ react with $W_1$ and $W_2$)

Monomer (C) may have a structure of formula (VI):

$$W_5\text{-T-}W_5 \quad\quad (VI)$$

wherein $W_5$ and $W_6$ are defined above, and wherein T is selected from the group consisting of optionally substituted $C_1$-$C_{12}$ alkylene, optionally substituted $C_1$-$C_{12}$ alkenylene, optionally substituted $C_3$-$C_{12}$ heterocyclyl, optionally substituted aryl, optionally substituted biaryl, —[O—($C_1$-$C_{12}$ alkylene)]-, —[S—($C_1$-$C_{12}$ alkylene)]$_n$-, where n is an integer from 1-1000, and combinations thereof. T may be selected from the group consisting of —[O—($C_1$-$C_{12}$ alkylene)]$_m$-, —[S—($C_1$-$C_{12}$ alkylene)]$_m$-, where m is an integer from 1-1000.

Suitably, $W_5$ and $W_6$ are independently selected from —OH, —CH₂OH, —COOH and —COOR⁵; preferably —CH₂OH and —COOH groups. Typically, $W_5$ and $W_6$ are the same functional groups. In one embodiment of the invention where monomer C is a polyether macromonomer, one of $W_5$ and $W_6$ are —OH (forming a secondary alcohol), and the other is —CH₂OH.

Monomer (C) may be used to determine the physical properties of the polymeric photoinitiator. Monomer (C) may e.g. promote water solubility. Suitably, monomer (C) may be a macromonomer, i.e. a polymer or oligomer that has a functional group that can take part in further polymerization. As such, monomer (C) may be selected from the group consisting of: polyethylene glycol (PEG), polypropylene glycol (PPG), random and block poly(ethylene glycol)-poly(propylene glycol) copolymers, poly(tetramethylene glycol) (PTMG), poly(1,4-butanediol adipate), poly(ethanediol 1,4-butanediol adipate), poly(caprolacton) diol, poly(1,6-hexanediol carbonate) and poly(ethylene terephthalate) diol. Monomer (C) may also comprise diols of other poly(C1-C6) alkylene oxides.

Monomer (C) could also be a low molecular weight monomer, such as a $C_1$-$C_{10}$ diol, e.g. 1,2-ethanediol, 1,3-propanediol or 1,4-butanediol.

The weight ratio of monomers (A):(B) is suitably 1:99-99:1, preferably 1:99-50:50. The weight ratio of monomers (A):(C) is suitably 1:99-99:1, preferably 1:99-50:50. The weight of the photoinitiator monomer (A) used to prepare polymeric photoinitiators may be between 0.1% and 99% of the total mass of other monomers, suitably between 0.2% and 10%, most suitably 0.5% to 5%.

One or more additional monomers (D) may also be present in the polymeric photoinitiators of the invention. Monomer (D) may be selected from R⁶—PCl₂, Ar⁵—PCl₂, R⁶—P(=O)Cl₂, Ar⁵—P(=O)Cl₂, R⁶—O—P(=O)Cl₂, Ar⁵—O—P(=O)Cl₂, wherein R⁶ is optionally substituted $C_1$-$C_{12}$ alkyl and Ar⁵ is optionally substituted aryl. Examples of such monomers include, but are not limited to, phenyldichlorophosphine (C₆H₅—PCl₂), methylphosphonic dichloride (CH₃—P(=O)Cl₂) and methyl dichlorophosphate (CH₃—O—P(=O)Cl₂). These monomers (D) may be used in preparing polymeric photoinitiators of the invention by co-polymerization with monomer (A) alone or together with other monomers (B) or (C), such as are described herein in relation to the first aspect of the invention. Monomers (D) may furthermore be used in polymeric photoinitiators of the invention incorporated into a polyacrylate according to the third aspect of the invention. Monomers (D) are suitable for making polyphosphonites, polyphosphonates and polyphosphates.

Suitably, the polymeric photoinitiator has a molecular weight of more than 1 kDa, suitably between 10 kDa and 1000 kDa, most suitably between 20 kDa and 100 kDa.

In the polymeric photoinitiator, the photoinitiator moiety Pi is pendant from the polymer backbone. As such, it is not able to leach from the polymer matrix. In addition, radical bond-forming reactions between the photoinitiator moiety and other components of the polymerization mixture will cause cross-linking, rather than forming undesirable low molecular weight compounds.

Further Aspects of the Invention Relating to Polymeric Photoinitiators

The invention further relates to a method for producing a polymeric photoinitiator, said method comprising step-growth co-polymerization of at least one monomer (A) with at least one monomer (B), wherein (A) and (B) have the structures described above. Preferably the polymeric photoinitiator may be a polyether-, polyester-, or polyurethane photoinitiator. More preferably the polymeric photoinitiator may be a polyether- or polyester photoinitiator. The co-polymerization reaction may additionally comprise one or more additional monomers (C), having the structure described above. Co-polymerization of monomers (A) and (B) may take place using any suitable reaction conditions, catalysts or reagents known to the skilled person. For instance, amines such as DABCO are known to catalyse polyurethane formation.

The polymeric photoinitiators (e.g. polyurethane photoinitiators) of the present invention form radical species upon exposure to radiation and/or heat. Application of radiation (as described in the section above entitled "Curing") excites the photoinitiator moiety, Pi, which then extracts protons from neighbouring functionalities, forming reactive radicals.

If the polymeric photoinitiator is the only component when irradiated, it will cross-link with itself, providing a cured polymer. The invention thus provides a method of cross-linking the polymeric photoinitiator of the invention, said method comprising exposing the polymeric photoinitiator as described herein to UV radiation and/or heat.

If the polymeric photoinitiator of the invention is mixed with monomers which can undergo radical polymerization (e.g. alkene monomers or acrylate monomers), rapid curing (=polymerization and cross-linking) of such monomers can occur. The present invention thus provides the use of a polymeric photoinitiator as described herein as a photoinitiator of radical polymerization.

It has been found that the polymeric photoinitiators of the present invention act to cure polymer matrices, at least as effectively, if not more effectively than known photoinitiators.

Additionally, the present invention relates to use of a photoinitiator monomers according to the first aspect of the invention of formula (I), or subformulas thereof, e.g. formula (Ia), in preparation of a polymeric photoinitiator. When used in this manner the photoinitiator monomers of formula (I) or (Ia) becomes incorporated by covalent bonds as monomers into the polymer via the two functional groups ($W_1$ and $W_2$). Accordingly, the present invention provides the use of photoinitiator monomers of formula (I) or (Ia) for incorporation as monomers into a polymer backbone via the functional groups $W_1$ and $W_2$. Preferably, said polymer may be a polyurethane, such as e.g. a polyalkyletherurethane, a polyurea, a polythiourethane, a polythiourea, a polydithiourethane, a polyester, a polycarbonate, a polyphosphonite, a polyphosphonate, or a polyphosphate; more preferably said polymer may be a polyurethane, a polyether, or a polyester; even more preferably a polyurethane or a polyether; or alternatively a polyurethane, such as e.g. a polyalkyletherurethane.

In an alternative embodiment of the above use, the polymer is a polyurethane or a polyesters. It has been found that the Polyesters obtained in this manner may be obtained quite pure without e.g. solvent contaminations of final products as the polymerization with the photoinitiator monomers can be made solvent free and any by-product may be removed easily.

Further details about the different types of polymers, or suitable $W_1$ and $W_2$ groups for such types of polymers, are described herein elsewhere and applies in full for this aspect of the invention.

Polyacrylate Polymers

The third aspect of the present invention provides a polyacrylate. A polyacrylate is a polymer based on acrylate monomers (Ac) comprising the moiety C=C—C(=O)—O—, or the corresponding N derivative C=C—C(=O)—N—, which polymerize at the alkene functional group.

The polyacrylate is obtained by radical polymerization of at least one acrylate monomer (Ac) in the presence of a polymeric photoinitiator as defined for the first aspect of the invention. The polymeric photoinitiator is a co-polymer of at least one monomer (A) with at least one monomer (B), the monomer (A) is a photoinitiator monomer of the general formula (I):

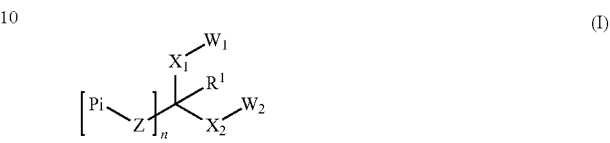

wherein general formula (I), or subformulas (Ia), (II), (III), (IIIa), (IIIb), (IIIc), (IV), (IVa), or (IVb), including preferred options of these, is as defined herein above or below; and monomer (B) is as defined herein for the first aspect of the invention;

wherein—in the co-polymerization of monomers (A) and (B) in the polymeric photoinitiator—$W_1$ reacts with $W_3$ to form a urethane, urea, amide, thiourethane, thiourea, dithiourethane, ester, ether, carbonate, phosphonite, phosphonate, phosphate, allophanate or biuret moiety, and $W_2$ reacts with $W_4$ to form a urethane, urea, amide, thiourethane, thiourea, dithiourethane, ester, ether, carbonate, phosphonite, phosphonate, phosphate, allophanate or biuret moiety.

Accordingly, the definitions of Pi, Z, $X_1$, $X_2$, $W_1$, $W_2$ $R^1$, $R^2$, and $R^3$, as described herein in connection with the photoinitiator monomers of formulas (I) and (Ia), applies for the third aspect of the invention as well. Polymerization is achieved by step-growth co-polymerization of monomers (A) and (B), and optionally also monomers (C) and/or (D). Monomer (B) is as described herein for the first aspect of the invention. The physical, chemical and photocatalytic properties of the polymeric photoinitiator can be varied depending on the nature and relative amounts of the monomers (A) and (B), and optionally also monomers (C) and/or (D).

In the polymeric photoinitiator, the photoinitiator moiety Pi is pendant from the polymer backbone. As such, it is not able to leach from the polymer matrix or the polyacrylate. In addition, radical bond-forming reactions between the photoinitiator moiety and the acrylate monomer (Ac) will cause cross-linking between these components, rather than forming undesirable low molecular weight compounds.

The polymeric photoinitiators (e.g. polyester, polyether, or polyurethane photoinitiators) form radical species upon exposure to radiation and/or heat. Application of radiation (as described in the section above entitled "Curing") excites the photoinitiator moiety, Pi, which then extracts hydrogen atoms from neighbouring functionalities, forming reactive radicals.

When the polymeric photoinitiator of the invention is mixed with acrylate monomers (Ac), these reactive radicals undergo chain propagation with the acrylate monomers (Ac), and rapid curing of such monomers can occur. As growth is initiated from the polymeric photoinitiator, the polymeric photoinitiator will itself be incorporated by means of covalent bonds into the growing polyacrylate. Scheme 3 gives an example of how the polymeric photoinitiator of the invention may be used in preparing a polyacrylate and especially how the polymeric photoinitiator itself becomes an integral part of the thereby formed polyacrylate.

Scheme 3

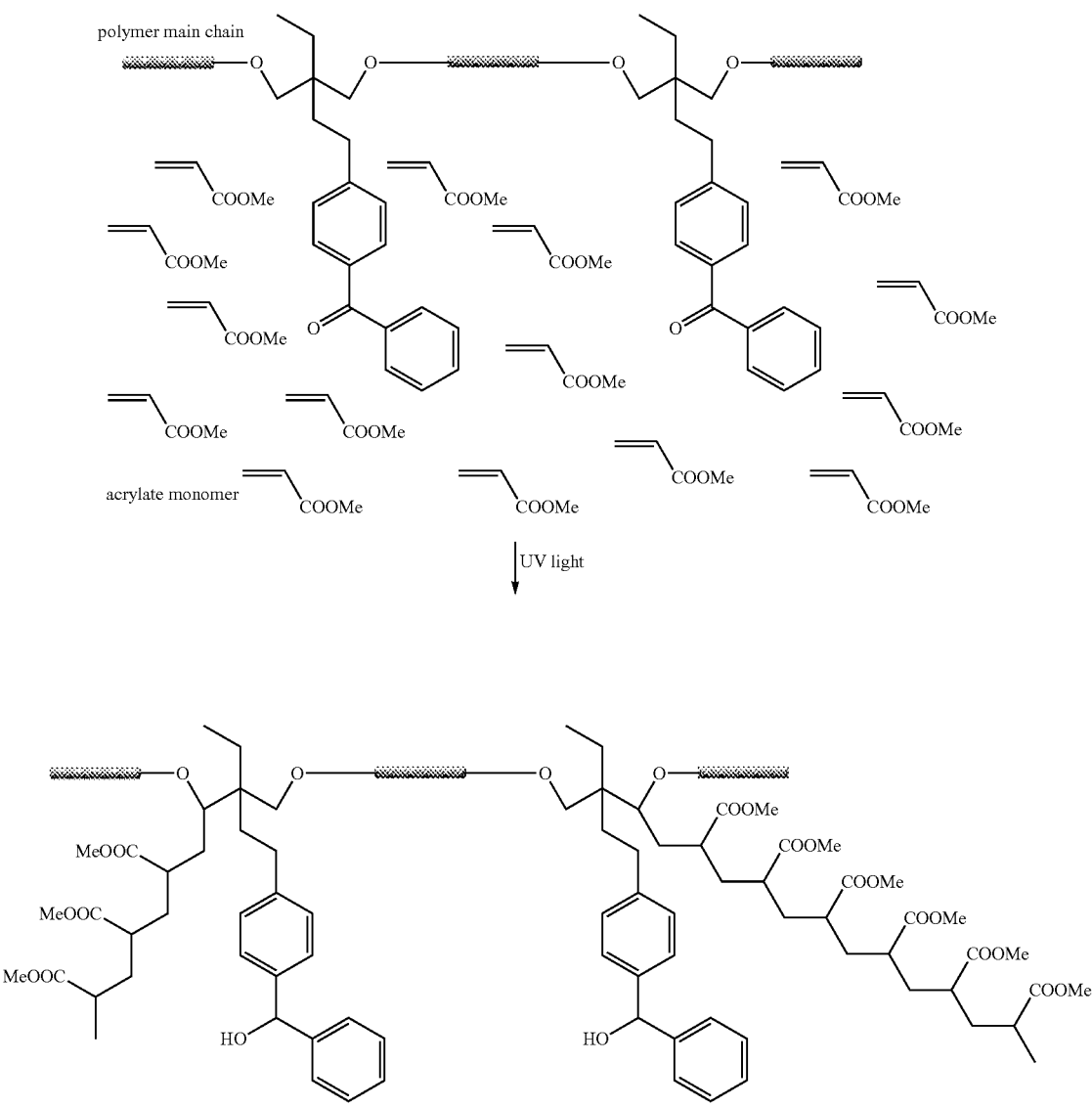

The acrylate monomer (Ac) used in the invention may be a mono-, di- or tri-acrylate (i.e. comprising one, two or three C=C—C(=O)—O— moieties, respectively, or the corresponding N derivative C=C—C(=O)—N—). Preferably, the acrylate monomer is a mono-acrylate.

Examples of acrylate monomers (Ac) useful in the present invention include ethylenically unsaturated monocarboxylic and dicarboxylic acids, such as acrylic acid, methacrylic acid, itaconic acid, maleic acid and fumaric acid, and monoalkyl esters of dicarboxylic acids of the type mentioned above with alkanols, preferably alkanols having from 1 to 4 carbon atoms and their N-substituted derivatives (amides), amides of unsaturated carboxylic acids, such as acrylamide, methacrylamide, N-methoxyacrylamide or methacrylamide, and N— alkylacrylamides, ethylenic monomers containing a sulphonic acid group and ammonium or alkali metal salts thereof, for example vinylsulphonic acid, vinylbenzenesulphonic acid, alpha-acrylamidomethylpropanesulphonic acid and 2-sulphoethylene methacrylate, amides of vinylamine, especially vinylformamide or vinylacetamide, and unsaturated ethylenic monomers containing a secondary, tertiary or quaternary amino group, or a heterocyclic group containing nitrogen, such as, for example, vinylpyridines, vinylimidazole, aminoalkyl (meth)acrylates and aminoalkyl (meth)acrylamides such as dimethylaminoethyl acrylate or methacrylate, di-tert-butylaminoethyl acrylate or methacrylate, dimethylaminoacrylamide or dimethylaminomethacrylamide, and 2-{[2-(acryloyloxy)ethyl](dimethyl)ammonio}-ethanesulfonate.

In addition to the above (meth)acrylates with a hydrophilic pendant chain such as poly(ethylene glycol) methyl ether acrylate may be useful.

Examples of difunctional acrylate monomers useful in the present invention include oligomers having two acrylate, methacrylate, acrylamide, or methacrylamide groups. Each of these monomers may comprise the same two functional groups or different functional groups. The difunctional acrylate monomers may preferably be selected from bisphenol A dimethacrylate, ethoxylated bisphenol A diacrylates (e.g., ethoxylated bisphenol A diacrylate with EO/phenol 1.0, 1.5, 2, 4, 10 or 15), ethoxylated bisphenol A dimethacrylates (e.g., ethoxylated bisphenol A dimethacrylate with EO/phenol 2 or 15), bisphenol A glycerolate dimethacrylate (e.g., bisphenol A glycerolate dimethacrylate with glycerol/phenol 1), polyethylene glycol diacrylates (e.g., polyethylene glycol diacrylate with average $M_n$, of 250, 575, 700, 1000, 2000, 6000 and 10000), ethylene glycol dimethacrylate, diethylene glycol dimethacrylate, triethylene glycol dimethacrylate, tetraethylene glycol dimethacrylate, polyethylene glycol dimethacrylates (e.g., polyethylene glycol dimethacrylate with average $M_n$, of 330, 550, 750, 2000, 6000 and 10000), dipropyleneglycol diacrylate, tripropyleneglycol diacrylate, polypropylene glycol diacrylates (e.g., polypropylene glycol diacrylate with $M_n$, of 800), dipropylene glycol dimethacrylate, tripropyleneglycol dimethacrylate and polypropylene glycol dimethacrylates (e.g., polypropylene glycol dimethacrylate with $M_n$, of 560), tetramethylene dimethacrylate, methylenebisacrylamide, methacryloxyethyl vinyl carbonate, methacryloxyethyl vinyl urea, divinyl benzene, diallyl itaconate, allyl methacrylate, diallyl phtalate, and polysiloxanylbisalkyl methacrylate. $M_n$, is number average molecular weight value. It is defined as arithmetic mean of the molecular weights of the individual macromolecules.

It may also be important to include zwitterionic monomers such as, for example, sulphopropyl(dimethyl)-aminopropyl acrylate.

Suitable di- or multifunctional cross-linking agents may be, but not being limited to, ethylene glycol dimethacrylate, triethylene glycol dimethacrylate, tetraethylene glycol dimethacrylate, trimethylopropane trimethacrylate, bisphenol A dimethacrylate, ethoxylate bisphenol A dimethacrylate, pentaerythritol tri- and tetrametacrylate, tetramethylene dimethacrylate, methylenebisacrylamide, methacryloxyethyl vinyl carbonate, triallylcyanurate, methacryloxyethyl vinyl urea, divinyl benzene, diallyl itaconate, allyl methacrylate, diallyl phtalate, polysiloxanylbisalkyl methacrylate and polyethylene glycol dimethacrylate.

Examples of multifunctional acrylate monomers useful in the present invention include oligomers having three or more acrylate, methacrylate, acrylamide, or methacrylamide groups. Each of these monomers may comprise the same two functional groups or different functional groups. The multifunctional acrylate monomers may preferably be selected from trimethylolpropane triacrylate, trimethylolpropane ethoxylate triacrylate (e.g., trimethylolpropane ethoxylate triacrylate with average $M_n$ of 400, 700 or 900), trimethylolpropane propoxylate triacrylate, trimethylopropane trimethacrylate, pentaerythritol triacrylate, pentaerythritol propoxylate triacrylate, glycerol propoxylate triacrylate, triallylcyanurate, pentaerythritol tetraacrylate, pentaerythritol tetramethacrylate, di(trimethylolpropane) tetraacrylate, dipentaerythritol pentaacrylate and dipentaerythritol hexaacrylate.

Oligo- or macromeric structures of a non-toxic nature are preferred. Of these, PEG containing di- or multifunctional oligo- or macromers may be of special interest. In the present invention, polyethylene glycol dimethacrylate of an approximately molecular weight of 400 (PEG-DMA 400) and an approximately molecular weight of 1000 (PEG-DMA 1000) may be preferred as cross-linking agent. In one embodiment the acrylate monomer (Ac) comprises a polyurethane oligomer having terminal acrylate groups.

Suitably, the acrylate monomer (Ac) is an acrylate ester of the formula (VII):

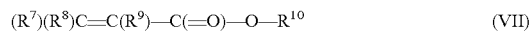

$$(R^7)(R^8)C=C(R^9)-C(=O)-O-R^{10} \qquad (VII)$$

wherein $R^7$-$R^9$ are independently selected from the group consisting of H, optionally substituted $C_1$-$C_{12}$ alkyl, optionally substituted $C_1$-$C_{12}$ alkenyl, optionally substituted $C_3$-$C_{12}$ heterocyclyl and optionally substituted aryl;

and $R^{10}$ is selected from the group consisting of optionally substituted $C_1$-$C_{12}$ alkyl, optionally substituted $C_1$-$C_{12}$ alkenyl, optionally substituted $C_3$-$C_{12}$ heterocyclyl and optionally substituted aryl.

Suitably, $R^7$ and $R^8$ are independently selected from H, methyl or ethyl.

Alternatively, the acrylate monomer (Ac) may comprise a polyurethane, a polyester or a polyether oligomer having terminal acrylate groups.

The polyacrylate of the invention may comprise two or more different acrylate monomers (Ac). Different acrylate monomers (Ac) can be mixed in various ratios, depending on the desired properties of the resulting polyacrylate.

The polyacrylate of the invention may comprise additional monomers. In this way, a copolymer of the acrylate monomer(s) (Ac) with other monomers may be obtained. For example, the polymeric photoinitiator of the invention may be used to initiate the copolymerization between acrylate monomers (Ac) and monomers such as vinylethers, vinylpyrrollidone and vinyllactams, vinyl acetates and vinylalcohol, vinylamines or mixtures of these. The additional monomers should be compatible with the acrylate monomers and the polymeric photoinitiator, and should polymerize via a radical mechanism, so that they can be incorporated with the acrylate monomer (Ac). Such additional monomers provide the skilled person with further opportunities to vary the physical and chemical properties of the resulting polyacrylate.

The polymeric photoinitiators of the invention with the photoinitiator moieties incorporated as pendant groups on the polymeric backbone are capable of self-cross linking under UV light. In the presence of acrylate monomers (Ac), self-cross linking of original polymer chains and radical chain propagation of the acrylate monomers (Ac) take place. Particularly, when suitable di- and/or multifunctional acrylate monomers are used, a densely cross-linked material is obtained that shows increased hardness.

Further Aspects of the Invention Relating to Polacrylates

The present invention further provides a method for producing a polyacrylate, said method comprising the steps of:

a. combining one or more acrylate monomers with a polymeric photoinitiator, said polymeric photoinitiator being as defined herein;

b. subjecting the mixture from step a. to UV radiation and/or heat.

The present invention also provides the use of a polymeric photoinitiator as described herein as a photoinitiator of radical polymerization of acrylate monomers (Ac).

Synthesis of Photoinitiator Monomers

Photoinitiator monomers according to the present invention may for example be synthesized via the synthetic routes described in Scheme 4:

Scheme 4:

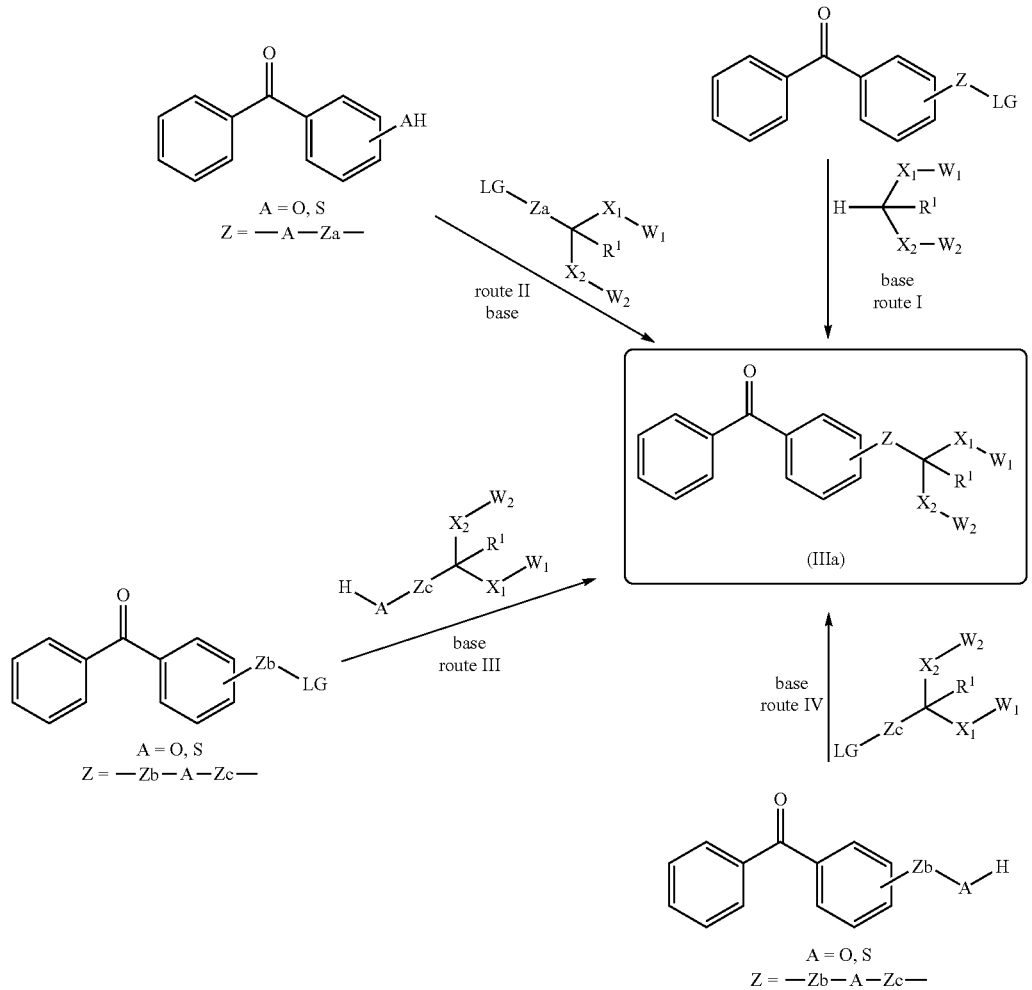

Route I is nucleophilic displacement of a leaving group LG (connected to a photoinitiator moiety via linker —Z—) by a carbanion nucleophile thus forming a new carbon-carbon bond. LG denotes a leaving group for example selected from —Cl, —Br, —I, —$OSO_2CH_3$, —$OSO_2$-(p-$C_6H_4$)—$CH_3$ or —$OSO_2CF_3$. The base may typically be e.g. tertiary amine, alkali metal alkoxide, hydroxide, carbonate or alkali metal salt of a secondary amine, such as lithium diisopropylamide. These reactions are typically carried out in polar solvents such as tetrahydrofuran, acetone, 2-butanone, dimethylformamide or dimethylsulfoxide at temperatures typically ranging from 0° C. to 80° C. Reactions of active methylene compounds with substrates bearing a leaving group are discussed, for example, in M. B. Smith, J. March; *March's Advanced Organic Chemistry: Reactions, Mechanisms, and Structure*, Sixth Edition, John Wiley & Sons 2007, ISBN 10: 0-471-72091-7, Chapter 10, Section 10-67.

Reactions II, III and IV are nucleophilic displacements of a leaving group LG by an alcoholate or thiolate anion. LG denotes a leaving group preferably selected from —Cl, —Br, —I, —$OSO_2CH_3$, —$OSO_2$-(p-$C_6H_4$)—$CH_3$ or —$OSO_2CF_3$. The base may typically be e.g. tertiary amine, alkali metal alkoxide, hydroxide and carbonate. These reactions are typically carried out in polar solvents such as tetrahydrofuran, acetone, 2-butanone, dimethylformamide or dimethylsulfoxide at temperatures typically ranging from 0° C. to 80° C. Such reactions are discussed, for example, in M. B. Smith, J. March; *March's Advanced Organic Chemistry: Reactions, Mechanisms, and Structure*, Sixth Edition, John Wiley & Sons 2007, ISBN 10: 0-471-72091-7, Chapter 10, Section 10-08.

Polymerization with Photoinitiator Monomers

The photoinitiator monomers of the present invention may be used as co-monomers in e.g. polyester, polyether or polyurethane polymers. Scheme 5 depicts a synthetic route for polymeric photoinitiators of the present invention. To carry this out, the photoinitiator monomers are mixed with suitable other monomers, optionally with further catalyst, and heated in a solvent or in bulk.

Scheme 5:

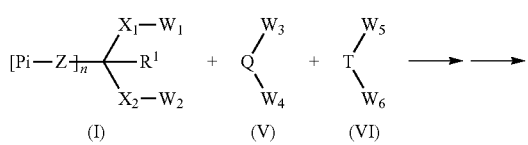

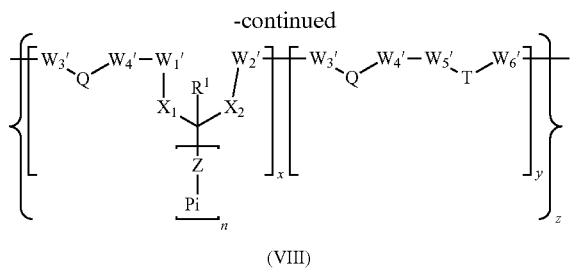

(VIII)

In Scheme 5, formulas (I), (V), and (VI), and the preferred embodiment thereof are as described herein above. Formula (VIII) is an example of a polymeric photoinitiator of the invention formed by co-polymerization of photoinitiator monomers of formula (I), for formation of for example a polyurethane. End groups $W_3$, $W_4$, $W_5$, $W_6$ are independently selected from the same end groups as $W_1$ and $W_2$. $W_3$ and $W_4$ are selected so as to be complementary to $W_1$, $W_2$, $W_5$ and $W_6$, so that urethane and urethane-like chains are formed. For instance, if the end groups $W_1$, $W_2$, $W_5$ and $W_6$ comprise alcohol, amine or thiol groups, suitable $W_3$ and $W_4$ will comprise isocyanate or isothiocyanate groups, and vice-versa.

Additional monomers may be introduced into the polyurethane according to the above scheme, as desired by the person skilled in the art. The additional monomers may for instance be other photoinitiator monomers of Formula (I) or other monomers of Formula (V) or Formula (VI).

The weight of the photoinitiator monomer (I) used to prepare e.g. a polyurethane polymer (VIII) may be between 0.1% and 99% of the total mass of other monomers, suitably between 0.2% and 10%, most suitably 0.5% to 5%.

Suitably, the polymer, e.g. a polyurethane polymer, (VIII) has a molecular weight of more than 1 kDa, suitably between 10 kDa and 1000 kDa, most suitably between 20 kDa and 100 kDa.

As set out above, the photoinitiator monomers of the present invention are incorporated into the polymer chain, as the end groups $W_1$, $W_2$, $W_5$ and $W_6$ react with the end groups $W_3$, $W_4$ of other monomers. The nomenclature $W_1'$, $W_2'$, $W_3'$, $W_4'$, $W_5'$ and $W_6'$ depict the corresponding end groups $W_1$-$W_6$ after being reacted.

The photoinitiator moiety therefore becomes pendant from the polymer backbone. As such, it is not able to leach from the polymer matrix. In addition, radical bond-forming reactions between the photoinitiator moiety and other components of the polymer itself or the polymerization mixture will cause cross-linking, rather than forming undesirable low molecular weight compounds.

It has been found that the polymeric photoinitiators of the present invention act to undergo UV self-crosslinking, at least as effectively, if not more effectively than known photoinitiators. There may be differences in the UV photo-crosslinking efficiency between the polymers prepared. The key factors that influence the physical characteristics of the crosslinked polymer film are photoinitiator type and incorporation level, initial polymer molecular weight, and availability of —CH$_2$—O— or —CH$_2$—N— groups in the polymer main chain. Groups such as —CH$_2$—N— and —CH$_2$—O— are efficient hydrogen donors that can react with the excited state of a proximal pendant photoinitiator like a benzophenone moiety. The resulting reactive —CH—O— radicals then readily undergo intermolecular recombination to form a covalent crosslink between two polymer chains.

The examples herein represent different variation of the above factors, and show the versatility e.g. by how it is possible to minimize the available —CH$_2$—O— groups and still obtain a crosslinkable polymeric photoinitiator. Table 1 gives a generalized overview of the prepared polymer types.

In case of the polyurethanes prepared in the examples, both molecular weight and relative content of —CH$_2$—O— groups in the polymer chain are high. Consequently, the polyurethane polymers require a low dose of radiation to crosslink efficiently. This among other show that there are a large margin wherein it is possible to vary such factors. The percentage of photoinitiator could be lowered and/or one could reduce the amount of PEG if different properties of the polymer are desired.

The polyether polymer prepared in the examples has a high photoinitiator content and a high —CH$_2$—O— group content, but its molecular weight is much lower. With a low molecular weight there are few photoinitiator sites on each polymer strand giving few sites for cross-linking. This is then outweighed by giving a moderate dose of radiation to obtain the desired crosslinking, and hence the desired change in physical properties and solubility. To reduce the radiation needed, a higher percentage of photoinitiators could be added, or the polymerization adapted to give a higher molecular weight.

To show the versatility of the polymeric photoinitiators of the invention, the polyester polymer prepared in the examples has an intermediate molecular weight between that of the prepared polyurethanes and polyethers. Furthermore, as this specific type of polyester is prepared from diethyl adipate and a photoinitiator monomer of the invention there are only very few —CH$_2$—O— groups available in the polymer chain. There are many fewer crosslinking sites available and a relatively high radiation dose is needed to create an insoluble polymer network (i.e. a higher number of passes under the UV lamp). Thus, even when taken to what could be considered an extreme it is possible to obtain an insoluble crosslinked polymer. However, it should be noted that polyesters may be prepared from any suitable components, such as for example including PEG macromonomers in order to both vary the properties of the polymer as such, but also to increase the available —CH$_2$O— groups for crosslinking.

TABLE 1

Relative comparison of properties and crosslinking efficiencies of polymers prepared

| Type of polymer | Relative molecular weight | Photoinitiator content | —CH$_2$—O— content | UV dose required for photo-crosslinking |
|---|---|---|---|---|
| Polyurethane | High | 5 wt % | 85 wt % | Low |
| Polyester | Intermediate | 5 wt % | 17 wt % | High |
| Polyether | Low | 12 wt % | 88 wt % | Moderate |

Polyurethane films comprising the polymeric photoinitiators of the present invention exhibit good adhesion in film form to hydrophobic surfaces, such as polypropylene, or other polyurethane containing materials. Accordingly, the polymeric photoinitiators of the present invention may preferably be polyurethanes Description of Polymerization Conditions Polyurethanes, polythiourethanes and polydithiourethanes are typically prepared from their respective monomers in solvents or in bulk. For solvent-based procedures, the typical solvents include tetrahydrofuran, toluene and chlorobenzene at temperatures ranging from 20° C. to 100° C. Catalysts such as dibutyltin dilaurate (DBTDL) or 1,4-diazabicyclo[2.2.2]

octane (DABCO) may be used to accelerate the reactions. Under bulk conditions, all components are reacted without solvent as a homogeneous reaction melt at temperatures typically between 50° C. to 120° C. Polyureas and polythioureas are typically prepared by analogous solvent-based or bulk procedures, but no catalyst is required since the polymerisation is typically very rapid at temperatures ranging from 20° C. to 100° C.

Polyurethane formation in the absence of a transition metal compound or a tertiary amine can be 10-500 times slower compared to the same reaction in the presence of a catalyst. The reaction times/reaction temperature can be increased accordingly to achieve the same degree of polymerisation. For general reference to polyurethane formation, see, for example, Encyclopedia of Polymer Science and Technology, John Wiley & Sons, Volume 4, p. 26.

Polyesters are typically prepared from their respective monomers in solvents such as toluene or xylenes in the presence of strong acid catalysts and with azeotropic removal of water or low molecular weight aliphatic alcohol by-product. Typical temperatures range from 80° C. to 150° C. Suitable protocols can be found, for example, in D. Braun, H. Cherdron, M. Rehahn, H. Ritter, B. Voit; Polymer Synthesis: Theory and Practice—Fundamentals, Methods, Experiments, Fourth Edition, Section 4.1.1.3. Applications of a mild and effective transesterification catalyst—titanium(IV) tetraisopropoxide—can be found, for example, in brochure *Johnson Matthey Catalysts, VERTEC™—Trans Esterification Technology*, © 2003 Johnson Matthey Group.

Polycarbonates are typically prepared in a solvent such as dichloromethane using a tertiary amine catalyst, while maintaining pH via the addition of NaOH. A melt transesterification process can also be used, which involves base-catalyzed reaction of a diol with diphenyl carbonate. Such reactions are discussed, for example, in Encyclopedia of Polymer Science and Technology, John Wiley & Sons, Volume 7, page 397.

Polyphosphonites, polyphosphonates and polyphosphates are typically prepared from the appropriate phosophorus-based reagents bearing —PCl$_2$, —P(═O)Cl$_2$ or —O—P(═O)Cl$_2$ function group, respectively, and a diol. The reactions can be conveniently carried out in aromatic solvents such as toluene at temperatures ranging from 0° C. to 80° C. in the presence of tertiary amines.

Experimental Section

Example 1

Synthesis of {4-[3-hydroxy-2(hydroxymethyl)propoxy]phenyl}(phenyl)methanone

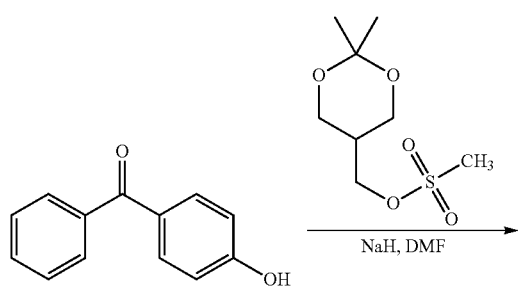

-continued

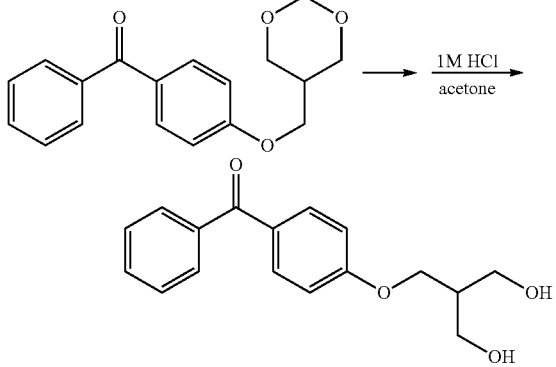

4-Hydroxybenzophenone is treated with equimolar quantity of sodium hydride in dry dimethylformamide at 0° C. under an inert atmosphere. After stirring at ambient temperature for 2 hours, a bright yellow clear solution is obtained. To this solution is added equimolar quantity of (2,2-dimethyl-1,3-dioxan-5-yl)methyl methanesulfonate (its synthesis in two steps from commercially available 2-hydroxymethyl-1,3-propanediol is described in European Patent EP2103611). After stirring at ambient temperature for 16 hours, the reaction mixture is diluted with water and extracted with dichloromethane. The organic phase is evaporated to dryness and the crude product is purified by column chromatography. This provide the intermediate {4-[(2,2-dimethyl-1,3-dioxan-5-yl)methoxy]phenyl}(phenyl)methanone. This intermediate is then dissolved in acetone, excess of 1M hydrochloric acid is added and the reaction mixture is stirred for 2 hours at room temperature. The reaction mixture is evaporated to dryness under reduced pressure, and the residue is purified by column chromatography to provide the desired {4-[3-hydroxy-2-(hydroxymethyl)propoxy]phenyl}(phenyl)methanone.

Example 2

General Procedure for the Preparation of Polyurethanes in Solvent

A glass vial is charged with {4-[3-hydroxy-2-(hydroxymethyl)propoxy]phenyl}(phenyl)-methanone and polyethylene glycol. The reaction vessel is heated to 120-130° C. under vacuum for 1 h to remove all moisture. The reaction vessel is then allowed to cool under vacuum, fitted with a reflux condenser and flushed with nitrogen. Dry chlorobenzene is added and the reaction is stirred at 60° C. to obtain a homogeneous clear solution with 30 wt % of solids. 0.2 wt % of dibutyltin dilaurate is added. Appropriate equimolar amount of diisocyanate is added via syringe and the reaction mixture is heated to 70° C. for 10 h. The viscous pale yellow mixture is evaporated in vacuo, residual chlorobenzene is removed by co-evaporation with MeOH-water. The resulting gummy solid is dried in vacuo for 4-6 h at 75° C. This provides the appropriate polyurethane polymer as a gummy solid.

Example 3

Procedure for the Preparation of a UV Photocrosslinkable Polyester in Solvent

A circulation apparatus for preparation of polyesters is set up as described in *Polymer Synthesis: Theory and Practice*;

Fourth Edition; D. Braun et al.; Springer. The reaction flask is charged with 0.20 mol 1,6-hexanediol (purified by vacuum distillation), 0.25 mol of recrystallized succinic acid, 0.05 mol {4-[3-hydroxy-2-(hydroxymethyl)propoxy]phenyl}(phenyl)methanone, dry toluene, and catalytic amount of pure p-toluenesulfonic acid; at the same time, the siphon is also filled with toluene so that the circulation of the solvent can begin immediately. The solution is heated on an oil to boiling; the toluene should flow quickly through the drying tube filled with soda-lime back into the flask. After some hours, when about three-quarters of the theoretical amount of water has collected in the separator, the soda-lime is renewed for the first time; it is renewed again after another 10 h. The viscosity of the solution gradually increases and so does the temperature in the flask. In order to maintain a quick rate of distillation (and therefore polycondensation), each time the internal temperature reaches 130° C. more pure toluene is added. After about 25 h the flask is cooled to room temperature and the solution is added dropwise to a tenfold amount of methanol; the polymer is filtered off and dried to constant weight in vacuum at 40° C. This provides the desired UV photocrosslinkable polyester.

Example 4

Procedure for the Preparation of a UV Photocrosslinkable Polyether in Solvent (adapted from S. Chatti et al., Eur. Polym. J. 40 (2004) 561-577)

Equimolar quantities of {4-[3-hydroxy-2-(hydroxymethyl)propoxy]phenyl}(phenyl)methanone and 1,8-dibromooctane are mixed with catalytic amount of tetrabutylammonium bromide and slight excess of powdered potassium hydroxide (containing approximately 15 wt % water) and minimum amount of toluene. The mixture is then homogenised and submitted to microwave irradiation under mechanical stirring. Temperature of 110° C. is maintained for 1 hour. The resulting mixture is cooled down to room temperature and diluted with 5 mL of chloroform. The solution is precipitated in methanol to obtain the polymer. The precipitate is dried overnight under vacuum to give the desired UV photocrosslinkable polyether.

Example 5

UV Curing of Polyurethanes

A polyurethane prepared in Example 2 is processed to a plate using a heat press. A disc is cut from this plate (⌀25 mm) and placed in a plate-plate rheometer, where the bottom plate consists of a quartz window. Rheological properties is measured at 1 Hz at 120° C., where a UV-light source irradiating the polyurethane sample through the quartz plate is turned on at t=0 s. After approximately 60 s the sample may a transition from a liquid state to a solid state, i.e. a gel-point, which demonstrates that the photoinitiator moieties within the polyurethane are actually responsible for curing the sample when exposed to UV light.

Example 6

UV Curing of Acrylics—Route to Polymerized N-Butyl Acrylate

A solution of 500 mg of a copolymer prepared in Example 2 in 10 mL THF is prepared. This solution is added to 10 mL of N-butylacrylate and mixed thoroughly. A film of this solution is spread out on a flat substrate and is subjected to UV irradiation and cured to provide a sticky solid.

Example 7

Synthesis of 3-(4-benzoylphenoxyl)propane-1,2-diol

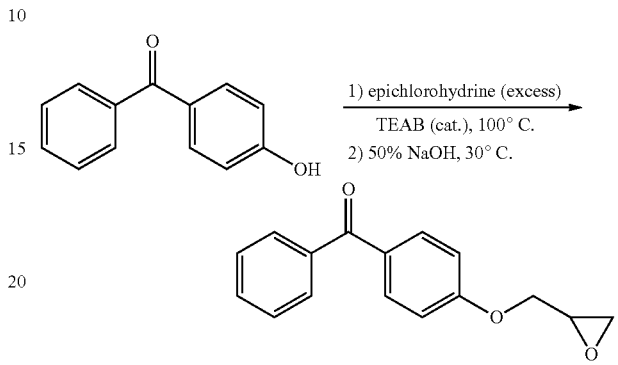

4-Hydroxybenzophenone (10.0 g; 50.5 mmol) was dissolved in epichlorohydrine (50 mL). Tetraethylammonium bromide (0.1 g; 0.48 mmol) was added and the reaction mixture was heated to 100° C. for 30 h under reflux. Near quantitative conversion of the starting material was confirmed by TLC. The reaction mixture was cooled to 30° C. and 50% aqueous NaOH (6.06 g, 75.7 mmol) was added dropwise to the vigorously stirred solution. The stirring was continued for a further 3 h at this temperature. The reaction mixture was then poured into methylene chloride (200 mL) and washed with water (3×50 mL). The organic layer was separated, dried over magnesium sulfate, filtered and evaporated to dryness. The crude product was recrystallised from methyl tert-butyl ether to yield 2-(4-benzoylphenoxymethyl)oxirane (10.66 g; 83% yield) as a white crystalline solid.

$^1$H NMR (400 MHz, CDCl$_3$): 7.82 (d, J=8.7 Hz, 2H), 7.75 (m, 2H), 7.57 (tt, J=7.4, 1.4 Hz, 1H), 7.47 (t, J=7.5 Hz, 2H), 6.98 (d, J=8.7 Hz, 2H), 4.33 (dd, J=11.0, 3.1 Hz, 1H), 4.02 (dd, J=11.1, 5.8 Hz, 1H), 3.39 (m, 1H), 2.94 (dd, J=4.7, 4.1 Hz, 1H), 2.79 (dd, J=4.9, 2.6 Hz, 1H).

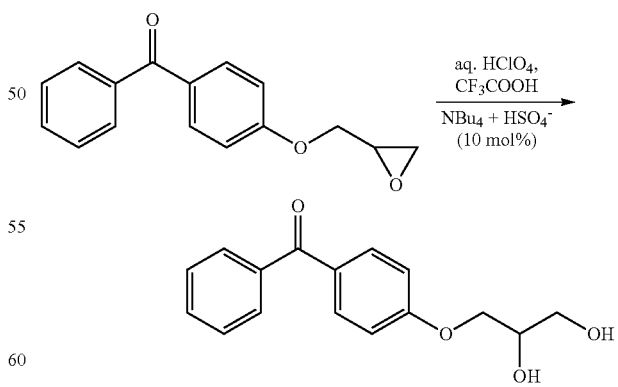

2-(4-benzoylphenoxymethyl)oxirane (10.0 g; 39.3 mmol) was dissolved in 1,2-dichloroethane (100 mL). To the solution was charged water (100 mL), 1 M aqueous perchloric acid (25 mL), trifluoroacetic acid (5 mL) and tetrabutylammonium hydrogensulfate (1.336 g; 3.93 mmol). The biphasic reaction mixture was stirred vigorously and heated to 70° C. for 6 h. The reaction was cooled to ambient temperature, diluted with dichloromethane (100 mL) and the organic phase was separated. The aqueous phase was further extracted with dichloromethane (50 mL). The solvent were evaporated to give a white solid. Recrystallisation from 1,2-dimethoxyethane/isopropylalcohol provided the desired 3-(4-benzoylphenoxyl)propane-1,2-diol as a white solid (7.05 g; 66% yield).

$^1$H NMR (400 MHz, CDCl$_3$): 7.70 (d, J=8.8 Hz, 2H), 7.65 (d, J=8.1 Hz, 2H), 7.51 (t, J=7.3 Hz, 1H), 7.40 (t, J=7.5 Hz, 2H), 6.89 (d, J=8.8 Hz, 2H), 4.47 (s, 2H), 4.12 (apparent quintet, J=5.0 Hz, 1H), 4.05 (s, 1H), 4.03 (s, 1H), 3.82 (dd, J=11.6, 3.7 Hz, 1H), 3.73 (dd, J=11.5, 5.9 Hz, 1H).

$^{13}$C NMR (100 MHz, CDCl$_3$): 195.9, 162.1, 137.7, 132.4, 132.0, 130.0, 129.5, 128.1, 113.9, 70.2, 68.9, 63.3.

UV: $\lambda_{max}$=290 nm (methanol), see FIG. 2 (bold black line).

Example 8

Synthesis of 1,3-diethyl 2-[(4-benzoylphenyl)methyl]propanedioate

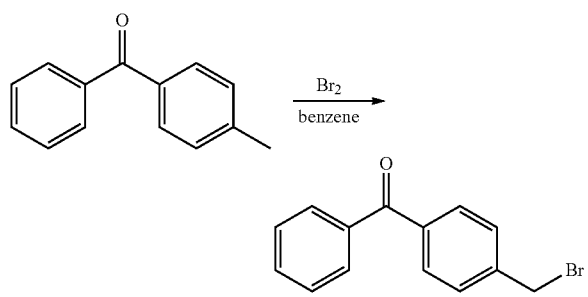

4-methylbenzophenone (10.0 g; 51.0 mmol) was dissolved in benzene (60 mL) and the solution was warmed to reflux. Solution of bromine (8.39 g; 52.5 mmol) in benzene (15 mL) was added to the reaction mixture over 10 h. The reaction was refluxed for a further 6 h until a light orange solution in obtained and all bromine is consumed. The benzene solvent was evaporated and crude product was obtained as an off-white solid. Recrystallisation from methanol (130 mL) provided 4-(bromomethyl)benzophenone (14.5 g; 69% yield) as a white crystalline solid.

$^1$H NMR (400 MHz, CDCl$_3$): 7.80-7.76 (m, 4H), 7.59 (tt, J=7.4, 1.3 Hz, 1H), 7.51-7.46 (m, 4H), 4.52 (s, 2H).

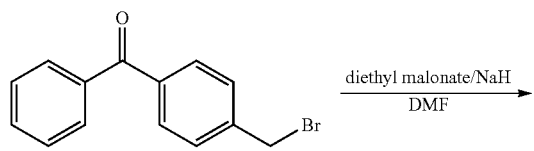

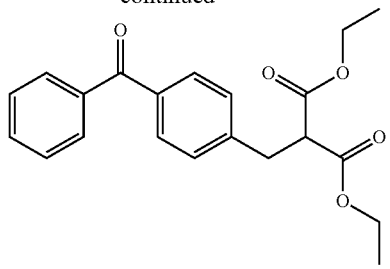

+

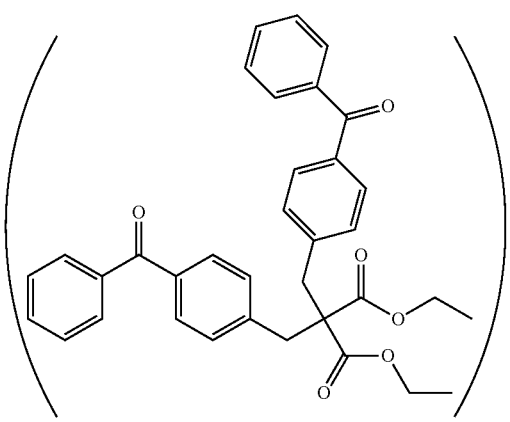

60% mineral oil suspension of sodium hydride (1.454 g; 36.3 mmol) was added into anhydrous DMF (50 mL) under nitrogen at 0° C. Diethyl malonate (5.82 g; 36.3 mmol) was added to the stirred suspension over 10 min and the mixture was then stirred rapidly at 0° C. until a clear pale yellow solution was obtained. 4-(bromomethyl)benzophenone (5.00 g; 18.2 mmol) in DMF (15 mL) was added dropwise over 5 min and the reaction mixture was stirred for 16 h at ambient temperature. Complete conversion of the starting bromide was confirmed by TLC. The reaction was diluted with water (400 mL) and extracted with dichloromethane (3×50 mL). The organic phase was separated, dried and evaporated to an oily residue. Chromatography on silicagel (eluent hexane/2-butanone 10:1→5:1) provided the desired 1,3-diethyl 2-[(4-benzoylphenyl)methyl]propanedioate (5.47 g; 86%) as a colourless oil.

$^1$H NMR (400 MHz, CDCl$_3$): 7.74-7.71 (m, 2H), 7.69 (d, J=8.2 Hz, 2H), 7.53 (tt, J=7.5, 1.4 Hz, 1H), 7.42 (t, J=7.6 Hz, 2H), 7.29 (d, J=8.2 Hz, 2H), 4.13 (m, 4H), 3.66 (t, J=7.9 Hz, 1H), 3.26 (d, J=7.9 Hz, 2H), 1.18 (t, J=7.2 Hz, 6H).

$^{13}$C NMR (100 MHz, CDCl$_3$): 196.07, 168.39, 142.74, 137.45, 135.91, 132.19, 130.22, 129.76, 128.67, 128.10, 61.45, 53.19, 34.39, 13.86.

UV: $\lambda_{max}$=257 nm (methanol), see FIG. 2 (dashed line).

The minor dialkylation product, 1,3-diethyl 2,2-bis[(4-benzoylphenyl)methyl]propanedioate (1.30 g; 13%), was isolated from the latter fractions as a white solid.

$^1$H NMR (400 MHz, CDCl$_3$): 7.77-7.75 (m, 4H), 7.72 (d, J=8.2 Hz, 4H), 7.55 (tt, J=7.3, 1.4 Hz, 2H), 7.45 (t, J=7.6 Hz, 4H), 7.28 (d, J=8.2 Hz, 4H), 4.13 (q, J=7.2 Hz, 4H), 3.32 (s, 4H), 1.16 (t, J=7.2 Hz, 6H).

$^{13}$C NMR (100 MHz, CDCl$_3$): 196.08, 170.32, 141.07, 137.44, 136.12, 132.26, 129.99, 129.95, 129.79, 128.16, 61.45, 59.80, 39.36, 13.79.

UV: $\lambda_{max}$=260 nm (methanol).

Example 9

Synthesis of 2-(4-benzoylphenoxymethyl)-2-ethylpropane-1,3-diol

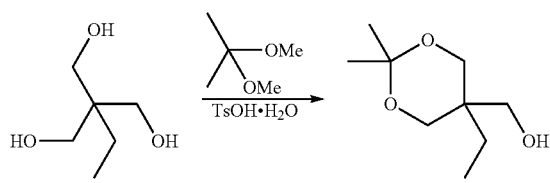

Trimethylolpropane (10.0 g; 74.6 mmol), 2,2-dimethoxyethane (9.01 g; 86.5 mmol) and p-toluenesulfonic acid monohydrate (0.369 g; 1.94 mmol) were dissolved in tetrahydrofuran (125 mL). The clear solution was stirred at ambient temperature for 24 h. TLC (stained with ammonium molybdate) confirmed near quantitative conversion of the starting triol. The reaction was neutralised with triethylamine (10 mL) and all volatiles were removed in vacuo. Colourless oily residue was passed through a silicagel column (eluent ethyl acetate/cyclohexane 1:1). The eluent was evaporated to provide (5-ethyl-2,2-dimethyl-1,3-dioxan-5-yl)methanol (12.34 g; 95% yield) as a colourless oil.

$^1$H NMR (400 MHz, CDCl$_3$): 3.70 (d, J=5.4 Hz, 2H), 3.65 (d, J=11.6 Hz, 2H), 3.61 (d, J=11.6 Hz, 2H), 2.41 (t, J=5.5 Hz, 1H), 1.40 (s, 3H), 1.37 (s, 3H), 1.28 (q, J=7.7 Hz, 2H), 0.82 (t, J=7.7 Hz, 3H).

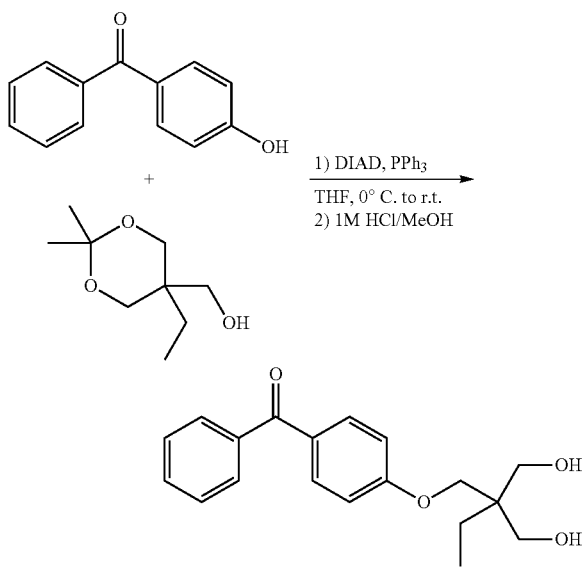

To a solution of 4-hydroxybenzophenone (2.00 g; 10.1 mmol), triphenylphosphine (4.234 g; 16.1 mmol) and (5-ethyl-2,2-dimethyl-1,3-dioxan-5-yl)methanol (2.813 g; 16.14 mmol) in anhydrous tetrahydrofuran (50 mL) at 0° C. was added diisopropyl azodicarboxylate (3.264 g; 16.14 mmol) dropwise over 10 min. The reaction mixture was stirred for 16 h at ambient temperature. TLC (eluent dichloromethane/acetone 10:1) confirmed ca 50% A) conversion. The reaction was warmed to 35-40° C. for 12 h and the conversion was monitored until ca 95% A) of 4-hydroxybenzophenone had reacted. The bright orange reaction mixture was evaporated to dryness, dissolved in dichloromethane and passed through a plug of silica. The eluent was again evaporated to dryness, redissolved in methanol (80 mL) and 1M HCl (22 mL) was added. The colourless reaction mixture was stirred for 1 h at ambient temperature, complete ketal cleavage was confirmed by TLC (eluent hexane/2-butanone 1:1). The methanol was evaporated to leave an aqueous residue. Water (150 mL) was added and the mixture was extracted with ethyl acetate (2×100 mL). The organic phase was separated, dried, evaporated and the oily crude product was purified by chromatography (eluent hexane/2-butanone 2:1→1:1). This provided the desired 2-(4-benzoylphenoxymethyl)-2-ethylpropane-1,3-diol (2.11 g; 66%) as a viscous colourless oil.

$^1$H NMR (400 MHz, CDCl$_3$): 7.70 (d, J=8.9 Hz, 2H), 7.65-7.63 (m, 2H), 7.47 (m, 1H), 7.38 (t, J=7.9 Hz, 2H), 6.89 (d, J=8.9 Hz, 2H), 4.15 (bs, 2H), 3.95 (s, 2H), 3.68-3.58 (m, 4H), 1.38 (q, J=7.5 Hz, 2H), 0.79 (t, J=7.6 Hz, 3H).

UV: $\lambda_{max}$=292 nm (methanol).

Example 10

Synthesis of Photocrosslinkable Polyurethanes—General Procedure

A glass vial was charged with polyethylene glycol 2000. The reaction vessel was heated to 120-130° C. under vacuum for 1 h to remove all moisture. The reaction vessel was then allowed to cool under vacuum and the appropriate diol photoinitiator was charged. The reaction mixture was warmed to 70° C. and fully homogenised. Hexamethylene diisocyanate was added with rapid stirring, followed by 0.5 wt % N-methylpiperidine and 0.5 wt % dibutytin dilaurate. The homogeneous clear reaction mixture was heated to 70° C. for 2 h and then cooled to ambient temperature. This provided the desired polyurethane polymer as a tough elastic solid.

Example 11

Synthesis of Photocrosslinkable Polyesters—General Procedure

A glass vial was charged with diethyl adipate, 1,6-hexanediol and the appropriate diol or diester photoinitiator. The mixture was homogenised and dried by stirring at 80-90° C. under oil pump vacuum for 1 h. Titanium(IV) tetraisopropoxide (1 wt %) transesterification catalyst was added, membrane vacuum pump was attached to the vials and the polymerisation mixture was warmed gradually to 160° C. At this temperature, rapid evolution of ethanol was seen while the liquid reaction mixture grew more viscous. The reaction was allowed to proceed at 160° C. under membrane pump vacuum for 2 hours. Then the reaction mixture was placed under oil pump vacuum and the reaction proceeded at 160° C. for another hour. The reaction mixture was cooled to ambient temperature to provide the desired polyester polymer as a white solid.

Example 12

Synthesis of Photocrosslinkable Polyethers—General Procedure

PEG 2000 dimesylate was prepared according to a procedure reported in patent EP 1028991. PEG 2000 (30.0 g; 15 mmol) was melted and dried in high vacuum for 1 h. The flask was cooled, and dichloromethane (100 mL) was added. The mixture was stirred until the PEG was completely dissolved, then the flask was placed in an ice-water bath. Triethylamine (8.35 mL; 60 mmol) was added followed by dropwise addition of mesyl chloride (6.97 mL; 90 mmol) over 10 minutes. The reaction was stirred at ambient temperature for 16 h, the precipitated ammonium salt was filtered off and the filtrate was evaporated to dryness. The product was recrystallized twice from boiling isopropylalcohol, filtered, washed with hexane (3×25 mL) and dried in vacuo. This provided the desired α,ω-dimesylate-PEG-2000 as an off-white soft solid.

A glass vial was charged with two molar equivalents of sodium hydride (60 wt ° A) dispersion in mineral oil) under nitrogen and anhydrous DMF was added. To the stirred suspension was added the appropriate diol photoinitiator (one molar equivalent) in DMF. The mixture was stirred at ambient temperature until the evolution of hydrogen had ceased. α,ω-dimesylate-PEG-2000 was added and the reaction mixture was stirred at ambient temperature for 16 h and then at 80° C. for 3 h. The viscous reaction mixture was cooled to ambient temperature and the DMF solvent was removed under vacuum. This provided the desired polyether polymer as a highly viscous semisolid.

Example 13

UV Photocrosslinking of Polyurethane Polymers—General Procedure

Two polyurethane polymers prepared according to the general procedure of Example 10 were each dissolved in methanol to give a viscous 15 wt ° A) solution. The solutions were spread onto a glass substrate using a 200 μm K-bar. Solvent was removed from the polymer films by heating to 80° C. for 5 minutes. Rub test prior to UV irradiation indicated that the films are well soluble in water. The coated substrate was passed under 900 W high pressure mercury lamp (Dymax UV-5 conveyor curing system, UV light intensity 7.5 W/cm², conveyor belt speed 16.5 m/s). As shown in Table 2, both polymer films become essentially water resistant after UV cross-linking.

TABLE 2

Composition of polyurethanes prepared and effects of UV curing

| Monomer (A) | Monomer (B) | Monomer (C) | Before irradiation | After 3 passes under UV lamp |
|---|---|---|---|---|
| 5 wt % diol from Example 7 | 10 wt % HDI | 85 wt % PEG 2000 | Fully soluble in water | Insoluble in water |
| 5 wt % diol from Example 9 | 10 wt % HDI | 85 wt % PEG 2000 | Fully soluble in water | Insoluble in water |

Example 14

UV Photocrosslinking of Polyester Polymers—General Procedure

Three polyester polymers prepared according to the general procedure in Example 11 were each melted at 80° C. and the resulting viscous liquids were spread onto a metal substrate using a 50 Jim K-bar. Rub test prior to UV irradiation indicated that the films can be easily removed from the metal substrate with methanol, but were insoluble in water. The coated substrate was passed under 900 W high pressure mercury lamp (same setting as in Example 13) while keeping the temperature of the metal substrate above 50° C., in order to subdue potential crystallisation. The cured polymers were allowed to cool to ambient temperature prior to testing the crosslinking by its resistance to solvent. As shown in Table 3, all polymer films develop significant resistance to rubbing with methanol and tetrahydrofuran.

TABLE 3

Composition of polyesters prepared and effects of UV curing

| Monomer (A) | Monomer (B) | Monomer (C) | Before irradiation | After 12 passes under UV lamp |
|---|---|---|---|---|
| 5 wt % diol from Example 7 | 61 wt % diethyl adipate | 34 wt % 1,6-hexanediol | Disintegrates in methanol | Resistant to methanol |
| 5 wt % diol from Example 9 | 61 wt % diethyl adipate | 34 wt % 1,6-hexanediol | Disintegrates in methanol | Resistant to methanol |
| 5 wt % diester from Example 8 | 59 wt % diethyl adipate | 36 wt % 1,6-hexanediol | Disintegrates in methanol | Resistant to methanol |

Example 15

UV Photocrosslinking of Polyether Polymers—General Procedure

A polyether polymer prepared according to the general procedure in Example 12 was melted at 60° C. and the resulting viscous liquid was spread onto a metal substrate using a 50 μm K-bar. Rub test prior to UV irradiation indicated that the film can be easily removed from the metal substrate with water. The coated substrate was passed under 900 W high pressure mercury lamp (same setting as in Example 13) while keeping the temperature of the metal substrate above 50° C., in order to subdue potential crystallisation. The cured polymers were allowed to cool to ambient temperature prior to testing the crosslinking by its resistance to water. As shown in Table 4, the polymer film develops significant resistance to water.

TABLE 4

Composition of polyether prepared and effects of UV curing

| Monomer (A) | Monomer (B) | Before irradiation | After 10 passes under UV lamp |
|---|---|---|---|
| 12 wt % diol from Example 7 | 88 wt % PEG-2000 dimesylate | Fully soluble in water | Insoluble in water |

Although the invention has been described with reference to a number of examples and reaction schemes, it should not be considered as limited by the above description. The full scope of the invention is defined by the appended claims.

The invention claimed is:

1. A polymeric photoinitiator, being a co-polymer of at least one monomer (A) with at least one monomer (B), wherein:

the at least one monomer (A) comprises formula (II):

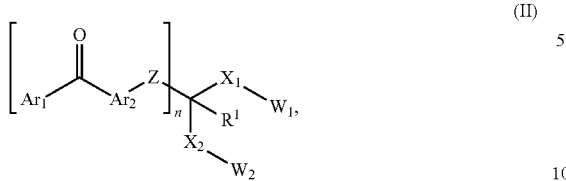

(II)

wherein $Ar_1$ and $Ar_2$ are each independently selected from the same or different aryl, where Z may be present at any position on $Ar_2$, where each aromatic ring is independently optionally substituted with one or more substituents;

Z is a linker moiety selected from a single bond, a $C_1$-$C_{12}$ alkylene, a $C_2$-$C_{12}$ alkenylene, a $C_3$-$C_8$ cycloalkyl, an aryl, a heterocyclyl, a —($C_1$-$C_{12}$ alkylene)-aryl-, an -aryl-($C_1$-$C_{12}$ alkylene)-, a —($C_1$-$C_{12}$ alkylene)-heterocyclyl-, a -heterocyclyl-($C_1$-$C_{12}$ alkylene)-, a —[O—($C_1$-$C_{12}$ alkylene)]$_m$-, a —[S—($C_1$-$C_{12}$ alkylene)]$_m$-, a —[($C_1$-$C_{12}$ alkylene)-O]$_m$—, a —[($C_1$-$C_{12}$ alkylene)-S-]$_m$-, a —[O—($C_1$-$C_{12}$ alkylene)]$_m$-O—, a —[S—($C_1$-$C_{12}$ alkylene)]$_m$-S—, a —[O—($C_1$-$C_{12}$ alkylene)]$_m$-S—, a —[S—($C_1$-$C_{12}$ alkylene)]$_m$-O—; a —C(=O)—, a —[C(=O)—($C_1$-$C_{12}$ alkylene)]$_m$-, a —[C(=O)-aryl]$_m$-, and a —[C(=O)-heterocyclyl]$_m$-;

$R^1$ is selected from H, a $C_1$-$C_{12}$ alkyl, a $C_2$-$C_{12}$ alkenyl, a $C_3$-$C_8$ cycloalkyl, an aryl, a heterocyclyl, a —[O—($C_1$-$C_{12}$ alkylene)]$_m$-H, a —[S—($C_1$-$C_{12}$ alkylene)]$_m$-H, a —C(=O)—H, a —[C(=O)—($C_1$-$C_{12}$ alkylene)]$_m$-H, a —[C(=O)-aryl]$_m$-H and a —[C(=O)-heterocyclyl]$_m$-H;

$X_1$ and $X_2$ are each independently selected from a single bond, a $C_1$-$C_{12}$ alkylene, a $C_2$-$C_{12}$ alkenylene, a $C_3$-$C_8$ cycloalkyl, an aryl, a heterocyclyl, a —[O—($C_1$-$C_{12}$ alkylene)]$_p$, and a —[S—($C_1$-$C_{12}$ alkylene)]$_p$;

wherein $X_1$, $X_2$, $R^1$ or Z each independently may be linked to one another to form one or more ring structures;

$W_1$ and $W_2$ are each independently selected from —OH, —$CH_2OH$, —COOH, —$COOR^2$, —COO-aryl, —SH, —$CH_2SH$, —$NH_2$, —$NHR^2$, —NCO, —NCS, —C(=O)—Cl, and —O—C(=O)—Cl;

$R^2$ is selected from an optionally substituted $C_1$-$C_{12}$ alkyl and aryl;

m is an integer from 1-10;

n is an integer of 1 or 2, with the proviso that when n is 2, $R^1$ is absent;

p is an integer from 1-10; and wherein any alkyl, alkenyl, alkylene, alkenylene, cycloalkyl, aryl, or heterocyclyl moiety each independently is an optionally substituted with one or more substituents selected from —F, —Cl, —Br, —I, —CN, —$NO_2$, —$C_1$-$C_6$ alkyl, aryl, —O—($C_1$-$C_6$ alkyl), —S—($C_1$-$C_6$ alkyl), —S(O)—($C_1$-$C_6$ alkyl), and —$SO_2$—($C_1$-$C_6$ alkyl);

wherein the at least one monomer (B) has the structure of formula (V):

$W_3$-Q-$W_4$ (V)

Q is selected from the group consisting of optionally substituted $C_1$-$C_{12}$ alkylene, optionally substituted $C_1$-$C_{12}$ alkenylene, optionally substituted $C_3$-$C_8$ cycloalkyl, optionally substituted $C_3$-$C_{12}$ heterocyclyl, optionally substituted aryl and optionally substituted biaryl;

$W_3$ and $W_4$ are each independently selected from —F, —Cl, —Br, —I, —$OSO_2R^4$, —$OSO_2$—$Ar^3$, —OH, —$CH_2OH$, —COOH, —$COOR^4$, —COO-aryl, —SH, —$CH_2SH$, —$NH_2$, —$NHR^4$, —NCO, —NCS, —C(=O)—Cl, and —O—C(=O)—Cl, wherein $R^4$ is selected from an optionally substituted $C_1$-$C_{12}$ alkyl; or $W_3$ and $W_4$ are linked to each other forming a cyclic lactone or thiolactone; and wherein $W_1$, $W_2$, $W_3$ and $W_4$ are selected such that $W_1$ reacts with $W_3$ to form a urethane, urea, amide, thiourethane, thiourea, dithiourethane, ester, ether, carbonate, phosphonite, phosphonate, phosphate, allophanate or biuret moiety, and $W_2$ reacts with $W_4$ to form a urethane, urea, amide, thiourethane, thiourea, dithiourethane, ester, ether, carbonate, phosphonite, phosphonate, phosphate, allophanate or biuret moiety.

2. The polymeric photoinitiator according to claim 1, wherein Z is selected from a $C_1$-$C_{12}$ alkylene, a $C_2$-$C_{12}$ alkenylene, a $C_3$-$C_8$ cycloalkyl, an aryl, a heterocyclyl, a —[O—($C_1$-$C_{12}$ alkylene)]$_m$-, a —[S—($C_1$-$C_{12}$ alkylene)]$_m$-, a —[($C_1$-$C_{12}$ alkylene)-O]$_m$—, a —[($C_1$-$C_{12}$ alkylene)-S-]$_m$-, a —[O—($C_1$-$C_{12}$ alkylene)]$_m$-O—, a —[S—($C_1$-$C_{12}$ alkylene)]$_m$-S—, a —C(=O)—, a —[C(=O)—($C_1$-$C_{12}$ alkylene)]$_m$-, a —[C(=O)-aryl]$_m$-, and a —[C(=O)-heterocyclyl]$_m$-, where any of these moieties independently is optionally substituted with one or more substituents.

3. The polymeric photoinitiator according to claim 1, wherein n is 1.

4. The polymeric photoinitiator according to claim 1, wherein n is 2.

5. The polymeric photoinitiator according to claim 1, wherein $R^1$ is selected from H, a $C_1$-$C_{12}$ alkyl, a $C_2$-$C_{12}$ alkenyl, a —[O—($C_1$-$C_{12}$ alkylene)]$_m$-H, a —[S—($C_1$-$C_{12}$ alkylene)]$_m$-H, a —C(=O)—H, and a —[C(=O)—($C_1$-$C_{12}$ alkylene)]$_m$-H, where any alkyl, alkylene, or alkenyl moiety independently is optionally substituted with one or more substituents.

6. The polymeric photoinitiator according to claim 1, wherein $X_1$ and $X_2$ each independently are selected from a $C_1$-$C_{12}$ alkylene, a $C_2$-$C_{12}$ alkenylene, a —[O—($C_1$-$C_{12}$ alkylene)]$_m$, and a —[S—($C_1$-$C_{12}$ alkylene)]$_m$, where any alkylene or alkenylene moiety independently is optionally substituted with one or more substituents.

7. The polymeric photoinitiator according to claim 1, wherein m is an integer from 1-5.

8. The polymeric photoinitiator according to claim 1, wherein $W_1$ and $W_2$ each independently are selected from —OH, —$CH_2OH$, —COOH, —$COOR^2$, —COO-aryl, —SH, —$CH_2SH$, —C(=O)—Cl, and —O—C(=O)—Cl.

9. The polymeric photoinitiator according to claim 1, wherein $W_1$ and $W_2$ each independently are selected from —$CH_2OH$, —COOH, —$COOR^2$ and —$CH_2SH$.

10. The polymeric photoinitiator according to claim 1, wherein $X_1$ and $X_2$ both are an optionally substituted $C_1$-$C_{12}$ alkylene, being the same or different, and $W_1$ and $W_2$ both are —$CH_2OH$.

11. The polymeric photoinitiator according to claim 1, wherein $Ar_1$ and $Ar_2$ each independently are optionally a substituted phenyl; where Z may be attached at any position on $Ar_2$.

12. The polymeric photoinitiator according to claim 1, wherein Z is present at the para-position on $Ar_2$.

13. The polymeric photoinitiator according to claim 1, wherein formula (II) comprises formula (III):

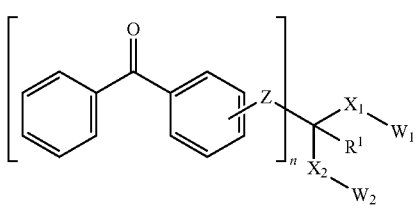
(III)

wherein Z may be attached at any position on the phenyl rings and the phenyl rings are each independently optionally substituted.

14. The polymeric photoinitiator according to claim 1, wherein formula (II) comprises formula (IIIa):

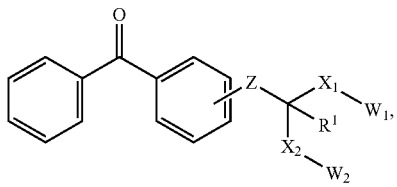
(IIIa)

wherein Z may be attached at any position on the phenyl ring and the phenyl rings are each independently optionally substituted.

15. The polymeric photoinitiator according to claim 1, wherein formula (II) comprises formula (IV):

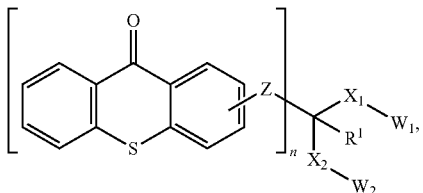
(IV)

wherein Z may be attached at any position on the aryl ring and the aryl rings are each independently optionally substituted.

16. The polymeric photoinitiator according to claim 1, wherein formula (II) comprises formula (IVa):

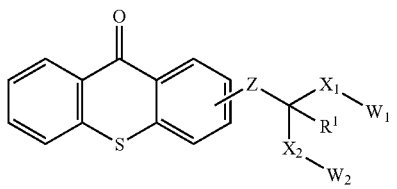
(IVa)

wherein Z may be attached at any position on the aryl ring and the aryl rings are each independently optionally substituted.

17. The polymeric photoinitiator according to claim 1, wherein formula (I) comprises formula (IIIb):

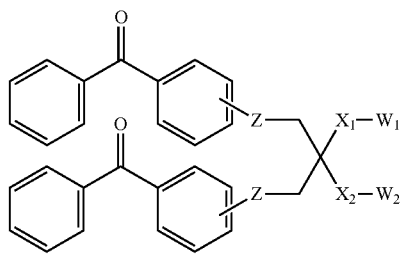
(IIIb)

wherein Z may be attached at any position on the phenyl ring and the phenyl rings are each independently optionally substituted.

18. The polymeric photoinitiator according to claim 1, wherein formula (II) comprises formula (IVb):

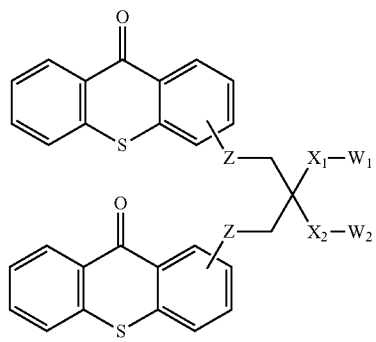
(IVb)

wherein Z may be attached at any position on the aryl ring and the aryl rings are each independently optionally substituted.

19. The polymeric photoinitiator according to claim 1, wherein the polymeric photoinitiator moiety is:
   4-[2,2-bis(hydroxymethyl)butan-1-yloxy]benzophenone;
   4-[2,2-bis(hydroxymethyl)butan-1-yloxymethyl]benzophenone;
   4-[5,5-bis(hydroxymethyl)-1,3-dioxan-2-yl]benzophenone;
   1-benzoyl-3-[2,2-bis(hydroxymethyl)butan-1-yloxymethyl]-2,4,6-trimethylbenzene;
   4-[1,3-dihydroxypropan-2-yloxy]benzophenone;
   4-[2,2-bis(hydroxymethyl)butan-1-yloxyethoxy]benzophenone;
   2,2-bis(4-benzoylphenoxymethyl)propane-1,3-diol;
   2,2-bis(1-chloro-9-oxo-9H-thioxanthen-4-yloxymethyl)propane-1,3-diol;
   2,2-bis(4-benzoylphenoxymethyl)propane-1,3-diamine;
   2,2-bis(4-benzoylphenoxymethyl)propane-1,3-dithiol;
   [4-(phenylcarbonyl)benzyl]propanedioic acid;
   [4-(phenylcarbonyl)benzyl]propanedioyl dichloride;
   dimethyl [4-(phenylcarbonyl)benzyl]propanedioate;
   4-[3-hydroxy-2-(hydroxymethyl)propan-1-yloxy]benzophenone;
   4-[4-hydroxy-3-(hydroxymethyl)butyl]benzophenone;
   4-3-hydroxy-2-(hydroxymethyl)-2-methylpropan-1-yloxy]benzophenone;
   4-[4-hydroxy-3-(hydroxymethyl)-3-methylbutyl]benzophenone; or
   dimethyl 2-[4-(phenylcarbonyl)benzyl]butanedioate.

20. The polymeric photoinitiator according to claim 1, wherein Q is selected from the group consisting of an optionally substituted aryl and an optionally substituted biaryl.

21. The polymeric photoinitiator according to claim 1, wherein $W_3$ and $W_4$ are independently selected from —F, —Cl, —Br, —I, —OSO$_2$R$^4$, —OSO$_2$—Ar$^3$, —OH, —CH$_2$OH, —COOH, —COOR$^4$, —SH, —NCO, —NCS, and —C(=O)—Cl.

22. The polymeric photoinitiator according to claim 1, wherein one of $W_3$ and $W_4$ is —CH$_2$OH and the other is —COOH.

23. The polymeric photoinitiator according to claim 1, wherein $W_3$ and $W_4$ are the same functional groups.

24. The polymeric photoinitiator according to claim 1, wherein the at least one monomer (B) is selected from the group consisting of: glycolic acid, lactic acid, 4-hydroxybutyric acid, 6-hydroxyhexanoic acid, malonic, succinic, glutaric, adipic, phthalic, and terephthalic acid.

25. The polymeric photoinitiator according to claim 1, wherein in the co-polymerization of the at least one monomer (A) and the at least one monomer (B), $W_1$ reacts with $W_3$ to form a urethane, thiourethane, urea, thiourea, ester, amide or ether moiety, and $W_2$ reacts with $W_4$ to form urethane, thiourethane, urea, thiourea, ester, amide or ether moiety.

26. The polymeric photoinitiator according to claim 1, wherein—in the co-polymerization of the at least one monomer (A) and the at least one monomer (B)—$W_1$ reacts with $W_3$ to form an ether or ester moiety, and $W_2$ reacts with $W_4$ to form an ether or ester moiety.

27. The polymeric photoinitiator according to claim 1, wherein both $W_1$ and $W_2$ are alcohol functional groups and both $W_3$ and $W_4$ are —COOH, —COOR$^2$, or —COO-aryl.

28. The polymeric photoinitiator according to claim 1, further comprising one or more additional monomers (C) comprising formula (VI):

$$W_5\text{-}T\text{-}W_6 \qquad (VI)$$

wherein T is selected from the group consisting of optionally substituted C$_1$-C$_{12}$ alkylene, optionally substituted C$_1$-C$_{12}$ alkenylene, optionally substituted C$_3$-C$_{12}$ heterocyclyl, optionally substituted aryl, optionally substituted biaryl, —[O—(C$_1$-C$_{12}$ alkylene)]$_q$-, —[S—(C$_1$-C$_{12}$ alkylene)]$_q$-, where q is an integer from 1-1000, and combinations thereof;

$W_5$ and $W_6$ each independently selected from —F, —Cl, —Br, —I, —OSO$_2$R$^5$, —OSO$_2$—Ar$^4$, —OH, —CH$_2$OH, —COOH, —COOR$^5$, —COO-aryl, —SH, —CH$_2$SH, —NH$_2$, —NHR$^5$, —NCO, —NCS, —C(=O)—Cl, and —O—C(=O)—Cl, wherein R$^5$ is selected from an optionally substituted C$_1$-C$_{12}$ alkyl and Ar$^4$ is selected from an optionally substituted aryl; and wherein $W_5$ and $W_6$ are selected such that $W_5$ reacts with $W_1$ or $W_3$ to form a urethane, thiourethane, urea, thiourea, ester, ether, amide, carbonate, allophanate or biuret moiety, and $W_6$ reacts with $W_2$ or $W_4$ to form a urethane, thiourethane, urea, thiourea, ester, ether, amide, carbonate, allophanate or biuret moiety.

29. The polymeric photoinitiator according to claim 28, wherein T is selected from the group consisting of —[O—(C$_1$-C$_{12}$ alkylene)]$_q$-, —[S—(C$_1$-C$_{12}$ alkylene)]$_q$-, where q is an integer from 1-1000.

30. The polymeric photoinitiator according to claim 28, wherein $W_5$ and $W_6$ are each independently selected from —OH, —CH$_2$OH, —COOH and —COOR$^5$.

31. The polymeric photoinitiator according to claim 28, wherein $W_5$ and $W_6$ are the same functional groups.

32. The polymeric photoinitiator according to claim 28, wherein the one or more monomer (C) is selected from the group consisting of: polyethylene glycol (PEG), polypropylene glycol (PPG), random and block poly(ethylene glycol)-poly(propylene glycol) copolymers, poly(tetramethylene glycol) (PTMG), poly(1,4-butanediol adipate), poly (ethanediol 1,4-butanediol adipate), poly(caprolacton) diol, poly(1,6-hexanediol carbonate) and poly(ethylene terephthalate) diol.

33. The polymeric photoinitiator according to claim 1, wherein the weight ratio of monomers (A):(B) is 1:99-99:1.

34. The polymeric photoinitiator according to claim 28, wherein the weight ratio of monomers (A):(C) is 1:99-99:1.

35. A polyacrylate obtained by radical polymerization of at least one acrylate monomer (Ac) in the presence of a polymeric photoinitiator, said polymeric photoinitiator being a co-polymer of at least one monomer (A) with at least one monomer (B), wherein:

the at least one monomer (A) is a photoinitiator monomer (A) of the formula (II):

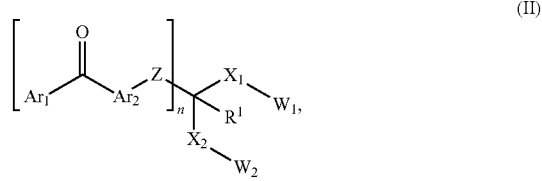

as defined in claim 1; and the at least one monomer (B) is as defined in claim 1;

wherein $W_1$ reacts with $W_3$ to form a urethane, urea, amide, thiourethane, thiourea, dithiourethane, ester, ether, carbonate, phosphonite, phosphonate, phosphate, allophanate or biuret moiety, and $W_2$ reacts with $W_4$ to form a urethane, urea, amide, thiourethane, thiourea, dithiourethane, ester, ether, carbonate, phosphonite, phosphonate, phosphate, allophanate or biuret moiety.

36. The polyacrylate according to claim 35, wherein the polymeric photoinitiator is as defined in claim 28.

37. The polyacrylate according to claim 35, wherein the at least one acrylate monomer (Ac) is a mono-, di- or tri-acrylate.

38. The polyacrylate according to claim 35, wherein the at least one acrylate monomer (Ac) is an acrylate ester comprising formula (VII):

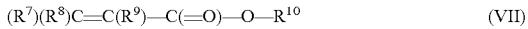

$$(R^7)(R^8)C=C(R^9)-C(=O)-O-R^{10} \qquad (VII)$$

wherein R$^7$-R$^9$ are independently selected from the group consisting of H, an optionally substituted C$_1$-C$_{12}$ alkyl, an optionally substituted C$_1$-C$_{12}$ alkenyl, an optionally substituted C$_3$-C$_{12}$ heterocyclyl, and an optionally substituted aryl, and R$^{10}$ is selected from the group consisting of an optionally substituted C$_1$-C$_{12}$ alkyl, an optionally substituted C$_1$-C$_{12}$ alkenyl, an optionally substituted C$_3$-C$_{12}$ heterocyclyl, and an optionally substituted aryl.

39. A method for producing a polymeric photoinitiator, said method comprising step-growth co-polymerization of at least one monomer (A) with at least one monomer (B), wherein (A) and (B) have the structures as defined in claim 1.

40. The method according to claim 39, wherein the co-polymerization reaction additionally comprises one or more additional monomers (C), having the structure as defined in claim 28.

41. A method of cross-linking the polymeric photoinitiator as defined in claim 1, said method comprising exposing the polymeric photoinitiator to UV radiation and/or heat.

42. A method for producing a polyacrylate, said method comprising the steps of:
 a) combining one or more acrylate monomers with a polymeric photoinitiator, said polymeric photoinitiator according to claim 1,
 b) subjecting the mixture from step a) to UV radiation and/or heat.

* * * * *